US012558334B2

(12) United States Patent
Thakor et al.

(10) Patent No.: US 12,558,334 B2
(45) Date of Patent: Feb. 24, 2026

(54) CONTROLLED NUTRIENT DELIVERY TO PANCREATIC ISLETS USING A NOVEL MESOPOROUS SILICA-BASED NANOPARTICLE PLATFORM

(71) Applicant: The Board of Trustees of the Leland Stanford Junior University, Stanford, CA (US)

(72) Inventors: Avnesh S. Thakor, Los Altos, CA (US); Mehdi Razavi, Palo Alto, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 952 days.

(21) Appl. No.: 17/760,714

(22) PCT Filed: Sep. 17, 2020

(86) PCT No.: PCT/US2020/051231
§ 371 (c)(1),
(2) Date: Mar. 15, 2022

(87) PCT Pub. No.: WO2021/055575
PCT Pub. Date: Mar. 25, 2021

(65) Prior Publication Data

US 2022/0401397 A1 Dec. 22, 2022

Related U.S. Application Data

(60) Provisional application No. 62/902,264, filed on Sep. 18, 2019.

(51) Int. Cl.
*A61K 31/198* (2006.01)
*A61K 9/51* (2006.01)
*A61K 35/55* (2015.01)
*B82Y 30/00* (2011.01)

(52) U.S. Cl.
CPC .......... *A61K 31/198* (2013.01); *A61K 9/5115* (2013.01); *A61K 9/513* (2013.01); *A61K 35/55* (2013.01); *B82Y 30/00* (2013.01)

(58) Field of Classification Search
CPC .................................................... A61K 31/198
See application file for complete search history.

(56) References Cited

U.S. PATENT DOCUMENTS

| | | | | |
|---|---|---|---|---|
| 6,046,046 | A | 4/2000 | Hassanein | |
| 10,273,453 | B2 * | 4/2019 | Garcia-Bennett | A61K 31/00 |
| 2005/0054102 | A1 * | 3/2005 | Wobus | C12N 5/0676 435/366 |
| 2018/0117171 | A1 | 5/2018 | Mooney et al. | |

FOREIGN PATENT DOCUMENTS

CN 109674763 A 3/2002

OTHER PUBLICATIONS

Hong et al. CAS: 145:331235, 2006.*
Ariga et al. Transaction of Materials Research Society of Japan, 2004, 29(7): 3179-3182.*
Sokolova et al., The efficacy of mesenchymal stem cells for the improvement of cerebral microcirculation in spontaneously hypertensive rats. Cell Tiss. Biol. 2017, 11, 343-348.
Paris et al. Polymer-Grafted Mesoporous Silica Nanoparticles as Ultrasound-Responsive Drug Carriers. ACS Nano 2015, 9 (11), 11023-11033.
Razavi et al. Collagen Based Cryogel Bioscaffold Coated with Nanostructured Polydopamine as a Platform for Mesenchymal Stem Cell Therapy. J. Biomed. Mater. Res.—Part A 2018, 106 (8), 2213-2228.
Ren et al. Adipose Tissue-Derived Mesenchymal Stem Cells Rescue the Function of Islets Transplanted in Sub-Therapeutic Numbers via Their Angiogenic Properties. Cell Tissue Res. 2019, 376(3),353-364.
Coronel et al. Mitigating Hypoxic Stress on Pancreatic Islets via in Situ Oxygen Generating Biomaterial. Biomaterials 2017, 129, 139-151.
Pedraza et al. Preventing Hypoxia-Induced Cell Death in Beta Cells and Islets via Hydrolytically Activated, Oxygen-Generating Biomaterials. Proc. Natl. Acad. Sci. 2012, 109 (11), 4245-4250.
Razavi et al. A Collagen Based Cryogel Bioscaffold That Generates Oxygen for Islet Transplantation. Adv Funct Mater. 2020, 30(15):1902463.
Faleo et al. Mitigating Ischemic Injury of Stem Cell-Derived Insulin-Producing Cells after Transplant. Stem Cell Reports 2017, 9 (3), 807-819.
Liu et al. Dose- and Glucose-Dependent Effects of Amino Acids on Insulin Secretion from Isolated Mouse Islets and Clonal INS-1E Beta-Cells. Rev. Diabet. Stud. 2008, 5 (4), 232-244.
Jang et al. Glutamine Induces Heat-Shock Protein-70 and Glutathione Expression and Attenuates Ischemic Damage in Rat Islets. Transplant. Proc. 2008, 40 (8), 2581-2584.
Lindstrom et al. Aromatic Amino Acids and Pancreatic Islet Function: A Comparison of I-Tryptophan and I-5-Hydroxytryptophan. Mol. Cell. Endocrinol. 1986, 48 (2-3), 121-126.
Mullooly et al. Elevated Levels of Branched-Chain Amino Acids Have Little Effect on Pancreatic Islet Cells, but I-Arginine Impairs Function through Activation of the Endoplasmic Reticulum Stress Response. Exp Physiol. 2014, 99(3):538-51.
Wang et al. Scaffold-Supported Transplantation of Islets in the (Continued)

*Primary Examiner* — Rei Tsang Shiao
(74) *Attorney, Agent, or Firm* — MARSHALL, GERSTEIN & BORUN LLP

(57) ABSTRACT

Nanoparticles, methods, and kits are provided for supplying nutrients and other therapeutic agents to transplanted cells. Nutrient deprivation is a significant factor which contributes to poor outcome of many cell transplants because cells receive insufficient nutrients until they are able to establish a functional microcirculation to support their metabolic and physiological needs after transplantation. Nanoparticles are provided for use in supplying nutrients and other therapeutic agents to transplanted cells to improve cell survival. Such nanoparticles can be used to supply nutrients and other factors to transplanted cells until the transplanted cells are able to develop a new microcirculation.

33 Claims, 44 Drawing Sheets

(56) References Cited

OTHER PUBLICATIONS pididymal Fat Pad of Diabetic Mice. J Vis Exp 2017, (125):54995.
Gibly et al. Porous Scaffolds Support Extrahepatic Human Islet Transplantation, Engraftment, and Function in Mice. Cell Transplant. 2013, 22 (5), 811-819.
Smink et al. Stimulation of Vascularization of a Subcutaneous Scaffold Applicable for Pancreatic Islet-Transplantation Enhances Immediate Post-Transplant Islet Graft Function but Not Long-Term Normoglycemia. J. Biomed. Mater. Res.—Part A 2017, 105 (9), 2533-2542.

* cited by examiner

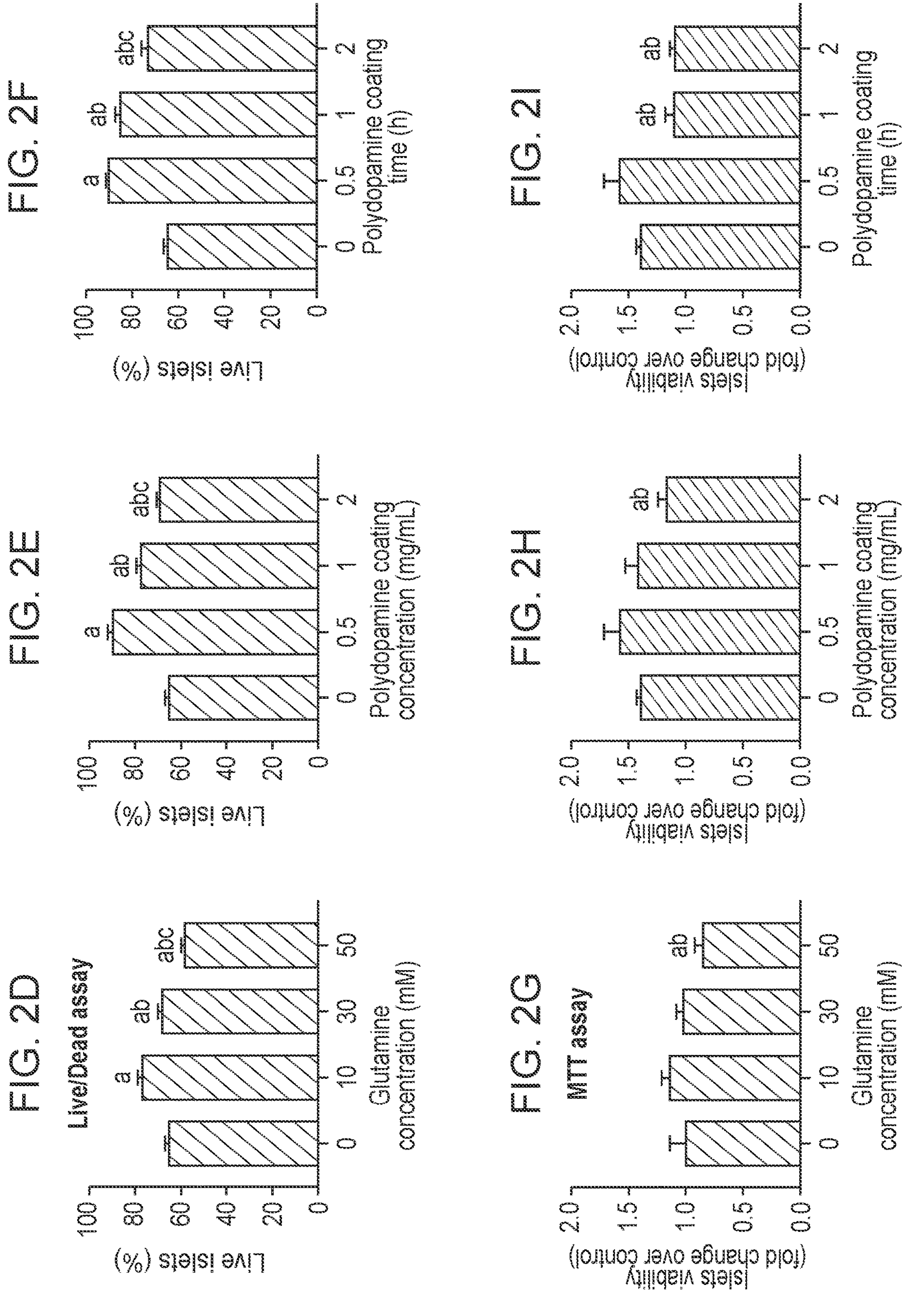
FIG. 2D
Live/Dead assay
Live islets (%)
100
80
60
40
20
0
a
ab
abc
0
10
30
50
Glutamine concentration (mM)
FIG. 2E
Live islets (%)
a
ab
abc
0
0.5
1
2
Polydopamine coating concentration (mg/mL)
FIG. 2F
Live islets (%)
a
ab
abc
0
0.5
1
2
Polydopamine coating time (h)
FIG. 2G
MTT assay
Islets viability (fold change over control)
2.0
1.5
1.0
0.5
0.0
ab
0
10
30
50
Glutamine concentration (mM)
FIG. 2H
Islets viability (fold change over control)
ab
0
0.5
1
2
Polydopamine coating concentration (mg/mL)
FIG. 2I
Islets viability (fold change over control)
ab
ab
0
0.5
1
2
Polydopamine coating time (h)

STZ Injection — Islets transplantation under the kidney capsule — Blood Glucose Measurment and Glucose Tolerance Test — Animal Sacrifice and Tissue Collection Day -5    0    30

Transplanted Kidney with islets

| | Islets only | Islets + glutamnine alone | Islets + PDG-MSNPs |
|---|---|---|---|
| Day 0 | | | |
| Day 30 | | | |

| | |
|---|---|
| IL-22 | 3.4 ± 0.5 |
| EOTAXIN | 1.7 ± 0.2 |
| GMCSF | 1.1 ± 0.09 |
| GCSF | 0.8 ± 0.1 |
| MIP-1β | 0.7 ± 0.1 |
| VEGF | 0.7 ± 0.05 |
| MCP-1 | 0.6 ± 0.04 |

Fold change vs control

Tissue Insulin (μg/mL)

Islets only     Islets with PDG-MSNPs

Schematic

No PD coating        0.5 mg/mL, 0.5 h PD coating        0.5 mg/mL, 1 h PD coating 0.5 mg/mL, 2 h PD coating        1 mg/mL, 0.5 h PD coating        2 mg/mL, 0.5 h PD coating

Surface area measurment

| | | |
|---|---|---|
| Specific surface area ($m^2/g$) | $S_{BET}$[a] | 869.3 |
| Pore volume ($cm^3/g$) | $V_T$[b] | 0.7 |
| Pore size (nm) | $D_{BET}$[c] | 3.3 |

[a]Brunauer-Emmer-Teller (BET) surface area.

[b]Single point adsorption total pore volume of pores less than 20.15 nm radius at P/P0 = 0.9500.

[c]Adsorption average pore diameter, obtained from 4 V/A by BET

CONTROLLED NUTRIENT DELIVERY TO PANCREATIC ISLETS USING A NOVEL MESOPOROUS SILICA-BASED NANOPARTICLE PLATFORM

CROSS-REFERENCE TO RELATED APPLICATIONS

This application is a U.S. National Phase of International Application No. PCT/US2020/051231, filed Sep. 17, 2020, which claims the priority benefit under 35 U.S.C. § 119(e) of U.S. Provisional Patent Application No. 62/902,264, filed Sep. 18, 2019, which are incorporated herein by reference in their entirety.

BACKGROUND OF THE INVENTION

Type 1 diabetes (T1D) is an autoimmune disease resulting in the targeted destruction of insulin-secreting β cells within pancreatic islets (Yoon et al. (2005) American Journal of Therapeutics 12:580-591). Islet transplantation is a promising clinical therapy for patients with T1 D whereby donor pancreatic islets are infused into the portal vein of the liver; here islets engraft and can then secrete insulin in response to elevated blood glucose levels thereby re-establishing autonomous glycemic control without the need for insulin injections. However, islet transplantation is yet to reach its full clinical potential which, in part, can be attributed to islets being lost either immediately following their transplantation (i.e. failure of engraftment) or later on (i.e. as a result of autoimmune mediated cellular rejection). Indeed, 60% of islets are lost within the first 2-3 weeks following transplantation, mainly from them having an underdeveloped vascular supply which, in turn, results in them suffering from hypoxia and nutrient deprivation (Biarnes et al. (2002) Diabetes 51 (1):66-72, Nilsson et al. (2011) Curr. Opin. Organ Transplant 16(6):620-626). Reasons for this include islets undergoing de-vascularization during their isolation procedure and islet transplantation not creating a surgical vascular anastomosis like most other organ transplants. Hence, for islets to survive over the long term, they need to build and secure a dedicated blood supply, which takes 2-3 weeks (Pepper et al. (2013) Clin. Dev. Immunol. 2013: 352315, Carlsson et al. (2001) Diabetes 50 (3):489-495). In the short term, islets therefore have to survive by relying on the diffusion of oxygen and nutrients from their microenvironment at the site where they are transplanted (Komatsu et al. (2017) PLoS One 12(8):e0183780); this is not ideal given the high metabolic requirements of islets, and especially those of insulin producing β cells (Komatsu et al. (2016) Biochem. Biophys. Res. Commun. 470 (3):534-538).

SUMMARY OF THE INVENTION

Compositions, methods, and kits are provided for supplying nutrients and other therapeutic agents to transplanted cells. Nutrient deprivation is a significant factor which contributes to poor outcome of many cell transplants because cells receive insufficient nutrients until they are able to establish a functional microcirculation to support their metabolic and physiological needs after transplantation. When cells do not receive sufficient nutrients, cells undergo a shift to anaerobic metabolism and energy conservation, which, if prolonged, will ultimately result in cell death. Hence, supplementation of nutrients immediately after transplant improves cell survival after transplantation by supporting cell viability and function until the transplanted cells are able to develop a new microcirculation to obtain their own nutrients.

In one aspect, a nanoparticle for supplying a therapeutic agent to transplanted cells is provided, the nanoparticle comprising: a) a mesoporous silica core comprising a plurality of pores; b) one or more therapeutic agents, wherein the plurality of pores contains the therapeutic agents; and c) a layer comprising polydopamine encapsulating the mesoporous silica core, wherein the layer comprising polydopamine has a thickness sufficient to allow sustained release of effective amounts of the one or more therapeutic agents from the nanoparticle at least until the transplanted cells develop a functional microcirculation.

In certain embodiments, the nanoparticle has a diameter ranging from about 50 nm to about 250 nm, including any diameter within this range such as 50, 55, 60, 65, 70, 75, 80, 85, 90, 95, 100, 105, 110, 115, 120, 125, 130, 140, 150, 160, 170, 180, 190, 200, 210, 220, 230, 240, or 250 nm.

In certain embodiments, the pores have a pore diameter ranging from 2 nm to 20 nm, including any diameter within this range such as 2, 3, 4, 5, 6, 7, 8, 9, 10, 11, 12, 13, 14, 15, 16, 17, 18, 19, or 20 nm. In one embodiment, the pore diameter is about 5 nm.

In certain embodiments, the thickness of the layer comprising the polydopamine is selected such that the nanoparticle sustains release of the one or more therapeutic agents for at least 14 days, wherein the thickness of the polydopamine layer determines the rate of its dissolution and hence the rate of release of the therapeutic agent from the nanoparticle. In some embodiments, the layer comprising the polydopamine has a thickness ranging from about 2 nm to about 10 nm, including any thickness within this range such as 2, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, or 10.0 nm.

Exemplary therapeutic agents that may be contained in the nanoparticle include, without limitation, small molecules, drugs, exosomes, antioxidants, and nutrients such as amino acids (e.g., glutamine, alanine, cysteine, tryptophan, leucine, methionine, isoleucine, arginine, lysine, proline, and homocysteine), proteins/peptides, carbohydrates (e.g. glucose), vitamins, and lipids, including fatty acids and sterols (e.g., cholesterol).

In certain embodiments, the nanoparticle is further loaded or conjugated with one or more imaging agents for use in medical imaging.

In another aspect, a method of supplying one or more therapeutic agents to transplanted cells in a subject is provided, the method comprising implanting a nanoparticle, described herein, in proximity to the transplanted cells, wherein the nanoparticle releases the one or more therapeutic agents from the plurality of pores to allow uptake of the one or more therapeutic agents by the transplanted cells.

In certain embodiments, the transplanted cells are insulin-secreting cells. For example, the insulin-secreting cells may be pancreatic beta cells or islets obtained from a donor. Alternatively, the insulin-secreting cells may be derived from stem cells or pancreatic progenitor cells.

Exemplary therapeutic agents that can be supplied to the transplanted cells by the nanoparticle include, without limitation, small molecules, drugs, exosomes, antioxidants, and nutrients such as amino acids (e.g., glutamine, alanine, cysteine, tryptophan, leucine, methionine, isoleucine, arginine, lysine, proline, and homocysteine), proteins/peptides, carbohydrates (e.g. glucose), vitamins, and lipids, including fatty acids and sterols (e.g., cholesterol).

In another aspect, a method of transplanting therapeutic cells into a subject is provided, the method comprising transplanting a therapeutically effective amount of the therapeutic cells in combination with administering a therapeutically effective amount of a composition comprising nanoparticles, described herein, locally at a transplantation site in the subject.

In another aspect, a composition comprising nanoparticles, described herein, for use in cellular therapy is provided. In certain embodiments, the composition further comprises a pharmaceutically acceptable excipient. In certain embodiments, the composition further comprises therapeutic cells.

In another aspect, a composition comprising nanoparticles comprising glutamine encapsulated therein for the treatment of type 1 diabetes in a subject is provided. In certain embodiments, the composition further comprises insulin-secreting cells such as, but not limited to, pancreatic beta cells or islets obtained from a donor. or insulin-secreting cells derived from stem cells or pancreatic progenitor cells In another aspect, a method of regulating blood glucose levels in a subject is provided, the method comprising transplanting a therapeutically effective amount of insulin-secreting cells at a transplantation site in the subject in combination with administering a therapeutically effective amount of a nanoparticle comprising glutamine, encapsulated therein, locally at the transplantation site.

In certain embodiments, the insulin-secreting cells are autologous, allogeneic, orxenogeneic pancreatic beta cells or islets. In other embodiments, the insulin-secreting cells are derived from stem cells or pancreatic progenitor cells.

In certain embodiments, the transplantation site is in a kidney, liver, omentum, peritoneum, abdomen, submuscular tissue, or subcutaneous tissue of the subject.

In certain embodiments, the subject has hyperglycemia or type 1 diabetes.

In another aspect, a kit comprising a composition comprising nanoparticles, described herein, and instructions for using the nanoparticles for supplying one or more therapeutic agents to transplanted cells is provided. In some embodiments, the kit further comprises means for administering the composition comprising the nanoparticles.

BRIEF DESCRIPTION OF THE DRAWINGS

FIG. 1A) Schematic representation of PDG-MSNPs: MSNPs synthesis, glutamine loading (G-MSNPs), polydopamine coating on G-MSNPs (PDG-MSNPs) and glutamine release from PDG-MSNPs. FIG. 1B) Cumulative loading profiles of glutamine into MSNPs showing that the glutamine loading efficiency is dose- and time-dependent. FIG. 1C) Polydopamine coating shows a color change from light to dark brown confirming the polydopamine coating on G-MSNPs. The brown color becomes increasingly darker as the concentration and time of polydopamine coating. FIGS. 1D, 1E) Representative TEM images of uncoated- and PDG-MSNPs. Images show a layer of dopamine on PDG-MSNPs. FIGS. 1F, 1I) DLS analysis and FIGS. 1G, 1J) XRD analysis of uncoated- and PDG-MSNPs obtained using different polydopamine coating concentrations (0, 0.5, 1, 2 mg/mL) and times (0, 0.5, 1, 2 h), respectively. FIGS. 1H, 1K) Cumulative release profiles of glutamine from PDG-MSNPs in PBS (pH=7.4) at 37° C., showing polydopamine coating resulted in a delay in the release of glutamine which, in turn, depended on the polydopamine coating concentration (FIG. 1H) and time (FIG. 1K). Results are expressed as average±SEM (n=5). Statistical analysis (Two-way ANOVA post-hoc Tuckey Test) is expressed as follows, with any differences considered statistically significant when $p<0.05$: (FIG. 1B)*$p<0.05$ incubation time 0 (baseline) vs. all other time-points, $^{a}p<0.05$ 10 mM vs. 30 and 50 mM; $^{b}p<0.05$ 30 mM vs. 50 mM; (FIG. 1F) see Table 1; (FIG. 1I) see Table 2; (FIG. 1H) *$p<0.05$ incubation time 0 (baseline) vs. all other time-points, $^{a}p<0.05$ 0 mg/mL vs. 0.5 mg/mL, 1 mg/mL and 2 mg/mL, $^{b}p<0.05$ 0.5 mg/mL vs. 1 mg/mL and 2 mg/mL, ° $p<0.05$ 1 mg/mL vs. 2 mg/mL; (FIG. 1K) *$p<0.05$ incubation time 0 (baseline) vs. all other time-points, $^{a}p<0.05$ 0 h vs. 0.5 h, 1 h and 2 h, $^{b}p<0.05$ 0.5 h vs. 1 h and 2 h, ° $p<0.05$ 1 h vs. 2 h.

FIGS. 2A-2L. In vitro Interactions of PDG-MSNPs with pancreatic islets. A) Representative Live/Dead confocal images of islets cultured with glutamine alone at different concentrations (0, 10, 30 and 50 mM), or FIGS. 2B, 2C) islets cultured with PDG-MSNPs with glutamine loading at 50 mM and different polydopamine coating concentrations (0, 0.5, 1, 2 mg/mL) (FIG. 2B) and times (0, 0.5, 1 and 2 h) (C) for 7 days after islet isolation. Red: Dead cells stained with PI. Green: Live cells stained with FDA. FIGS. 2D-21) Viability of islets performed with a Live/Dead assay (FIGS. 2D-2F) and a MTT assay (FIGS. 2G-21) of islets cultured with glutamine alone at different concentrations (0, 10, 30, and 50 mM) (FIGS. 2D, 2G) or PDG-MSNPs with different polydopamine coating concentrations (0, 0.5, 1 and 2 mg/mL) (FIGS. 2E, 2H) and times (0, 0.5, 1 and 2 h) (FIGS. 2F, 2I) after 7 days. L-N) Functionality of islets evaluated with a GSIS assay after 7 days of incubation of islets in different conditions: glutamine alone at different concentrations (0, 10, 30, and 50 mM) (FIG. 2J), PDG-MSNPs with different polydopamine coating concentrations (0, 0.5, 1 and 2 mg/mL) (FIG. 2K) and times (0, 0.5, 1 and 2 h) (FIG. 2L). Functionality has been reported as the amount of insulin secretion (ng/mL) in low (2.8 mM of glucose) and high glucose (16.7 mM of glucose) conditions. Results are expressed as average±SEM (n=5). Statistical analysis (Two-way ANOVA post-hoc Tuckey Test) is expressed as follows, with any differences considered statistically significant when $p<0.05$: (FIGS. 2D, 2G) *$p<0.05$ incubation time 0 (baseline) vs. all other time-points, $^{a}p<0.05$ 10 mM vs. 30 and 50 mM; $^{b}p<0.05$ 30 mM vs. 50 mM; (FIGS. 2E, 2H) *$p<0.05$ incubation time 0 (baseline) vs. all other time-points, $^{a}p<0.05$ 0 mg/mL vs. 0.5 mg/mL, 1 mg/mL and 2 mg/mL, $^{b}p<0.05$ 0.5 mg/mL vs. 1 mg/mL and 2 mg/mL, ° $p<0.05$ 1 mg/mL vs. 2 mg/mL; (FIGS. 2F, 2I) *$p<0.05$ incubation time 0 (baseline) vs. all other time-points, $^{a}p<0.05$ 0 h vs. 0.5 h, 1 h and 2 h, $^{b}p<0.05$ 0.5 h vs. 1 h and 2 h, ° $p<0.05$ 1 h vs. 2 h; (FIG. 2J) *$p<0.05$ Low glucose vs. High glucose, $^{a}p<0.05$ 10 mM vs. 30 and 50 mM; $^{b}p<0.05$ 30 mM vs. 50 mM; (FIG. 2K) *$p<0.05$ Low glucose vs. High glucose, $^{a}p<0.05$ 0 mg/mL vs. 0.5 mg/mL, 1 mg/mL and 2 mg/mL, $^{b}p<0.05$ 0.5 mg/mL vs. 1 mg/mL and 2 mg/mL, ° $p<0.05$ 1 mg/mL vs. 2 mg/mL; (FIG. 2L) *$p<0.05$ Low glucose vs. High glucose, $^{a}p<0.05$ 0 h vs. 0.5 h, 1 h and 2 h, $^{b}p<0.05$ 0.5 h vs. 1 h and 2 h, ° $p<0.05$ 1 h vs. 2 h.

FIG. 3A) Experimental detail for in vivo experiments. FIG. 3B) Photograph of the transplanted kidney using islets only, islets supplemented with glutamine alone and islets supplemented with PDG-MSNPs at day 0 (i.e. at the time of transplantation) and 30 (i.e. at the time of sacrifice) post-transplantation (white arrow=islets transplanted in kidney). FIG. 3C) Non-fasting Blood Glucose measurements over 30 days post-transplantation. FIG. 3D) Fasting Intraperitoneal Glucose Tolerance Test (IPGTT). FIG. 3E) Normoglycemia percentage. FIG. 3F) Area under the IPGTT curve ($AUC_{0\text{-}120\ min}$). FIG. 3G) Blood glucose clearance rates calculated from slope of IPGTT curves from 30 to 90 min. FIG. 3H) Weekly monitoring of the body weight of transplanted mice. Results are expressed as the average±SEM (n=6). Statistical analysis (Two-way ANOVA post-hoc Tuckey Test) is expressed as follows, with any differences considered statistically significant when p<0.05: *p<0.05 incubation time 0 (baseline) vs. all other time-points, $^{a}$p<0.05 islets only vs. islets supplemented with glutamine alone and islets supplemented with PDG-MSNPs; $^{b}$p<0.05 islets supplemented with glutamine alone vs. islets supplemented with PDG-MSNPs.

FIG. 4A) Representative histological (H&E staining) and immunohistochemical images (insulin and TNF-α staining) of islets transplanted under the kidney capsule (black arrow=islets). FIG. 4B) Quantification of islet surface area, positive FIG. 4C) insulin and FIG. 4D) TNF-α staining. FIG. 4E) The level of insulin within blood serum and FIG. 4F) kidney tissue. FIG. 4G) Fold change in cytokine expression within kidney tissue that contained transplanted islets supplemented with PDG-MSNPs relative to those samples of transplanted islets only (i.e. control). Results were analyzed with at least 15-20 islets from 5 different sections through the kidney of each animal. Results are expressed as average±SEM (n=6). Statistical analysis (unpaired Student's t-test) is expressed as follows, with any differences considered statistically significant when p<0.05: *p<0.05: islets only vs. islets with PDG-MSNPs.

FIG. 5A) Overview diagram showing the temporal relationship between the need for nutrients over the first 2 weeks after islet transplantation and the time taken for islets to establish their own blood supply. FIG. 5B) Schematic representation showing our nanoscale platform (PDG-MSNP), which can be used to deliver nutrients, such as glutamine, to islets and the mechanism of how glutamine regulates insulin secretion in β-cells within the pancreatic islet.

FIGS. 6A, 6B) The surface charge of uncoated- and PDG-MSNPs obtained using different polydopamine coating concentrations (0, 0.5, 1, 2 mg/mL) (FIG. 6A) and times (0, 0.5, 1, 2 h) (FIG. 6B). Results are expressed as average±SEM (n=5). Statistical analysis (Two-way ANOVA post-hoc Tuckey Test) is expressed as follows, with any differences considered statistically significant when p<0.05: (FIG. 6A)$^{a}$p<0.05 0 mg/mL vs. 0.5 mg/mL, 1 mg/mL and 2 mg/mL, $^{b}$p<0.05 0.5 mg/mL vs. 1 mg/mL and 2 mg/mL, ° p<0.05 1 mg/mL vs. 2 mg/mL; (FIG. 6B)$^{a}$p<0.05 0 h vs. 0.5 h, 1 h and 2 h, $^{b}$p<0.05 0.5 h vs. 1 h and 2 h, ° p<0.05 1 h vs. 2 h.

FIG. 7. TEM analysis of MSNPs. Representative TEM images of uncoated- and polydopamine (PD) coated-G-MSNPs obtained using different polydopamine coating concentrations (0, 0.5, 1, 2 mg/mL) and times (0, 0.5, 1, 2 h). Images show a very uneven surface for uncoated G-MSNPs, whereas a smoother surface is observed for polydopamine coated G-MSNPs.

FIG. 8. TEM analysis of MSNPs. Representative TEM images of MSNPs at high magnifications showing the MSNP's pores indicated by white arrows.

FIG. 10A) Table showing the surface area measurement of MSNPs, including specific surface area, pore volume and size of uncoated MSNPs. FIGS. 10B, 10C) Adsorption/desorption isotherm and average pore radius of MSNPs, respectively.

FIG. 11A) HADDF image (grey), FIG. 11B) corresponding element mapping images of Si, FIG. 11C) overlapped image of HAADF and Si mapping, and FIG. 11D) energy dispersive X-ray spectrum of uncoated MSNPs. Si and O peaks are related to MSNPs and Cu indicate the copper grid.

FIGS. 12A, 12B) Glutamine concentrations for two islets with diameter=120 & 150 μm cultured alone or FIGS. 12C, 12D) with PDG-MSNPs that release glutamine (0.01 $M/s/m^3$) and are assumed to be homogeneously dispersed in the media surrounding the islets. Data are shown in a system assumed to be in an aqueous media at physiological temperature (37° C.) with islets having a glutamine consumption of 5 nM/day/islet=0.033 $M/s/m^3$, extracellular glutamine concentration of 0.7 mM, and a glucose concentration of 8 mM. Top row (FIGS. 12A, 12C) shows calculations assuming simple diffusion between intra- and extracellular domains, while bottom row (FIGS. 12B, 12D) assumes a partition coefficient of 5 between islets and the surrounding media (islets are modeled as essentially a single large cell). Glutamine concentrations are color-coded from blue for high to red for low with red indicating levels that are below the critical concentration of glutamine ($c_{glutamine}<c_{critical}$) for islet survival. Assuming a glutamine consumption rate of 5 nM/day/islet,[6] this result illustrated that the core of islets cultured without glutamine demonstrated both reduced viability and functionality (FIGS. 12A-12B). On the contrary, when islets were cultured with PDG-MSNPs, our computational model showed that glutamine released from PDG-MSNPs (with a glutamine release rate of 0.01 $M/s/m^3$) improved islet viability and function (FIGS. 12C-12D).

(FIG. 13A) Results of protein array analyses show differences in the protein expression of islets cultured with PDG-MSNPs compared to islets only (control). Results are expressed as average±SEM (n=5). The statistical analysis (unpaired Student's t-test) is expressed as following, considering any differences statistically significant when p<0.05: *p<0.05: islets only vs. islets cultured with PDG-MSNPs. (FIG. 13B) The protein array assay assessed that islets supplemented with our optimized PDG-MSNPs (i.e. polydopamine coating concentration of 0.5 mg/mL and time of 0.5 h) had a significantly higher expression of growth hormone 1 (GH1; 18048±994 vs. 225±138 mean pixel density, p<0.05), glucose-regulated protein-75 (GRP-75; 27506±2774 vs. 1652±323 mean pixel density, p<0.05), heat shock protein A9 (HSPA9; 42954±2133 vs. 375±55 mean pixel density, p<0.05), and heat shock protein 32 (HSP32; 115320±15444 vs. 1523±353 mean pixel density, p<0.05). On the contrary, the expression of heat shock protein 90 (HSP90) was significantly decreased in islets cultured with PDG-MSNPs compared to islets only (1909±104 vs. 30016±2075 mean pixel density, p<0.05). This result shows that, PDG-MSNPs had cytoprotective effects on islets via the induction of growth hormones (GHs), glucose-regulated proteins (GRPs)

and heat shock proteins (HSPs) compared to islets cultured with glutamine alone. Islets cultured with PDG-MSNPs highly expressed: GH1 (a growth hormone which regulates immune function),[23] GRP-75 and HSPA9 (members of the HSP70 family which regulate cell growth and survival)[24,25] and HSP32 (a stress-related survival factor that can protect against inflammatory reactions and stress responses).[26] On the contrary, the expression of HSP90 (a molecular chaperone that promotes both folding and degradation and is associated with apoptosis)[27] was lower in islets cultured with PDG-MSNPs. Our findings are consistent with previous studies which have shown that rat islets supplemented with glutamine will increase the expression of HSP70[20] and mammalian cells supplemented with other amino acids will increase the expression of both HSPs and GRPs.[28] Recent work has also identified HSP32 (heme oxygenase-1) to possess potent proangiogenic properties in addition to well-recognized anti-inflammatory, antioxidant, and antiapoptotic effects.[29] Angiogenic factors, such as VEGF and stromal cell-derived factor-1 (SDF-1), mediate their proangiogenic effects through induction of HSP32, making it an attractive target for therapeutic intervention.[30] Hence, these results shows that PDG-MSNPs have indirect proangiogenic effects on islets via the induction of HSP32.

Figure 14:
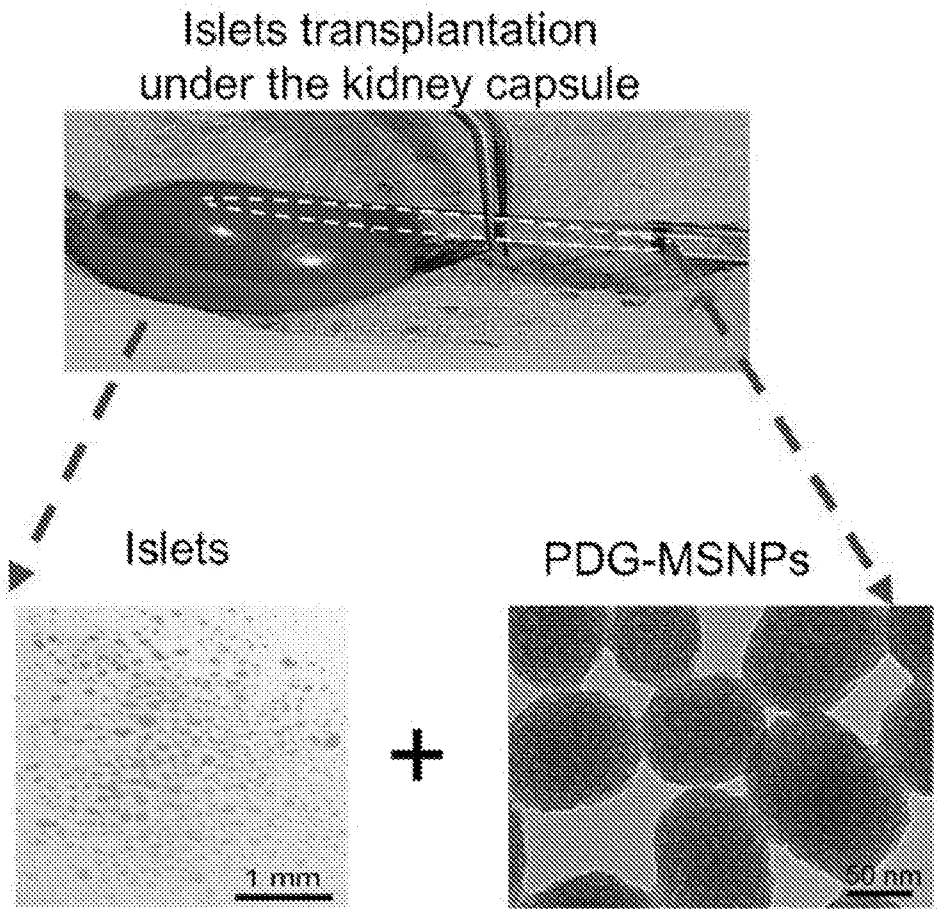

FIG. 14. Islet transplantation performed under the kidney capsule. Photographs of the transplantation procedure of islets (representative image of islets obtained with stereomicroscope after islet isolation procedure) supplemented with PDG-MSNPs (representative TEM image of PDG-MSNPs).

Figure 15:
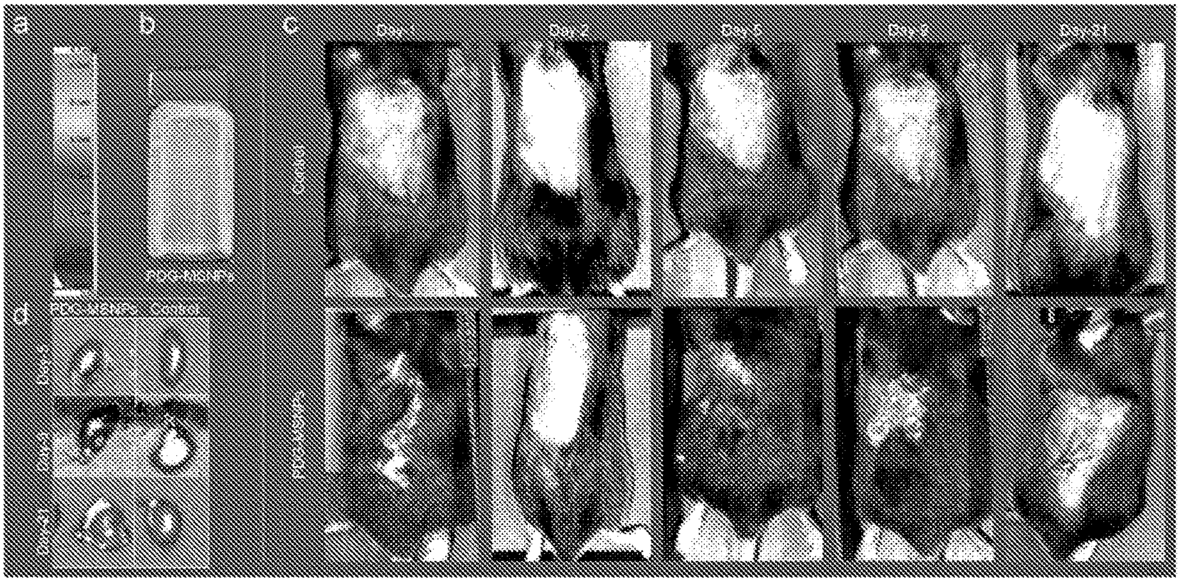

FIG. 15. IVIS imaging of our FITC-PDG-MSNPs: (a) color scale bar demonstrating fluorescent intensity, (b) optical image of the fluorescent intensity of our FITC-PDG-MSNPs, (c) in vivo imaging of C57/B6 mice implanted with our FITC-PDG-MSNPs under their kidney capsule at day 1, 2, 5, 9, and 21 post-implantation, and control non-implanted mice, (d) ex vivo imaging of harvested kidneys of mice transplanted with FITC-PDG-MSNPs at day 5, 9, and 21 post-implantation and control non-implanted mice. Following implantation of our FITC-PDG-MSNPs, a persistent fluorescent signal was observed from the kidney at day 1, 2, 5, 9 and 21 post-implantation. This fluorescent signal was observed only in the kidney in which they were implanted and not in any other organ. This result shows the stability of our PDG-MSNPs over the time period required for delivery of nutrients to islets following transplantation (i.e. 2 weeks). Furthermore, our PDG-MSNPs remain at their site of implantation with no accumulation or redistribution to any other organ.

Figure 16A:
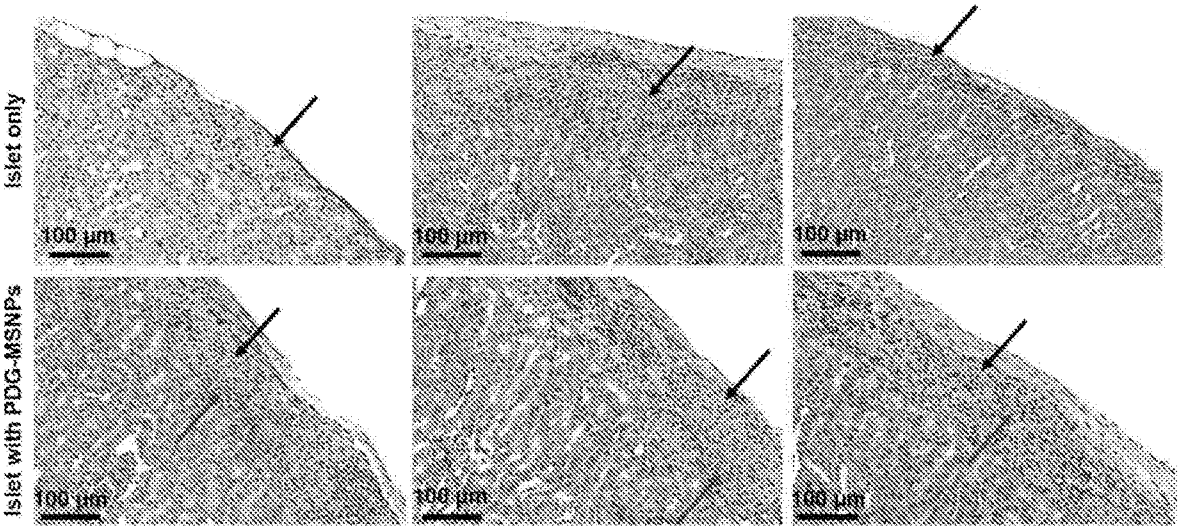
Figure 16B:
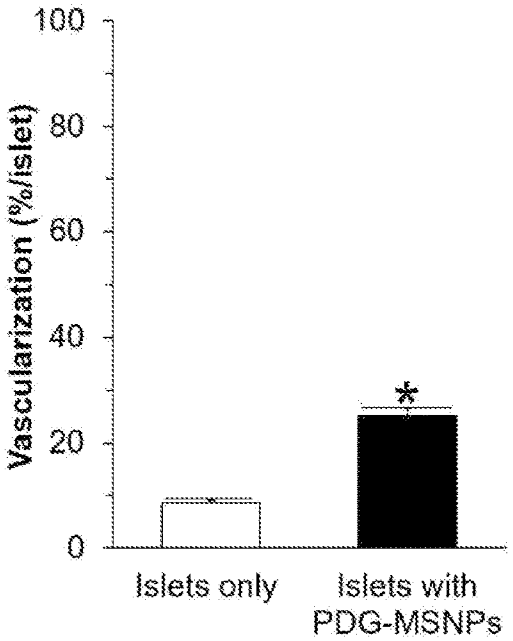

FIGS. 16A-16B. Histological analysis of kidney tissue after mice sacrifice. FIG. 16A) Representative histological images (H&E staining) of islets transplanted under the kidney capsule (black arrow=islets and red arrow=blood vessels). FIG. 16B) Quantification of blood vessels within and around islets supplemented with PDG-MSNPs relative to transplanted islets only (i.e. control). Results are expressed as average±SEM (n=6). Statistical analysis (unpaired Student's t-test) is expressed as follows, with any differences considered statistically significant when $p<0.05$: *$p<0.05$: islets only vs. islets with PDG-MSNPs. Using this histological analysis performed on tissue (i.e. kidneys) explanted 30 days post-transplantation, transplanted islets with PDG-MSNPs demonstrated a greater degree of vascularity compared to islets only (25.17±1.45 vs. 8.50±0.53%; $p<0.05$).

DETAILED DESCRIPTION OF THE INVENTION

Nanoparticles, methods, and kits are provided for supplying nutrients and other therapeutic agents to transplanted cells. Nutrient deprivation is a significant factor which contributes to poor outcome of many cell transplants because cells receive insufficient nutrients until they are able to establish a functional microcirculation to support their metabolic and physiological needs after transplantation. Compositions comprising nanoparticles are provided for use in supplying nutrients and/or other therapeutic agents to transplanted cells to improve cell survival. Such compositions can be used to supply nutrients and/or other therapeutic agents to transplanted cells until the transplanted cells are able to develop a new microcirculation.

Before the present compositions, methods, and kits are described, it is to be understood that this invention is not limited to particular methods or compositions described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the nanoparticle" includes reference to one or more nanoparticles and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "about," particularly in reference to a given quantity, is meant to encompass deviations of plus or minus five percent.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

"Biocompatible," as used herein, refers to a property of a material that allows for prolonged contact with a tissue in a subject without causing toxicity or significant damage.

"Substantially" as used herein, may be applied to modify any quantitative representation that could permissibly vary without resulting in a change in the basic function to which it is related.

"Diameter" as used in reference to a shaped structure (e.g., nanoparticle, pore, cell aggregate, etc.) refers to a length that is representative of the overall size of the structure. The length may in general be approximated by the diameter of a circle or sphere that circumscribes the structure.

A "plurality" contains at least 2 members. In certain cases, a plurality may have at least 10, at least 100, at least 1000, at least 10,000, at least 100,000, at least $10^6$, at least 107, at least $10^8$ or at least 109 or more members.

A "therapeutic agent" refers to any chemical compound or substance that can have a therapeutic and/or prophylactic effect for a disease when suitably administered to a subject. Exemplary therapeutic agents include, without limitation, small molecules, drugs, exosomes, antioxidants, and nutrients such as amino acids (e.g., glutamine, alanine, cysteine, tryptophan, leucine, methionine, isoleucine, arginine, lysine, proline, and homocysteine), proteins/peptides, carbohydrates (e.g. glucose), vitamins, and lipids, including fatty acids and sterols (e.g., cholesterol).

"Substantially purified" generally refers to isolation of a substance (e.g., compound, nanoparticle, polynucleotide, protein, peptide, antibody, aptamer) such that the substance comprises the majority percent of the sample in which it resides. Typically in a sample, a substantially purified component comprises at least 50%, preferably at least 80%-85%, and more preferably at least 90-95% of the sample. Techniques for purifying substances of interest are well-known in the art and include, for example, ion-exchange chromatography, affinity chromatography, gel filtration, and sedimentation according to density.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

"Therapeutically effective amount" refers to an amount effective, at dosages and for periods of time necessary, to achieve the desired therapeutic result.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including substituted ammonium).

As used herein, the term "cell viability" refers to a measure of the number of cells that are living or dead, based on a total cell sample. High cell viability, as defined herein, refers to a cell population in which greater than 80% of all cells are viable, preferably greater than 90-95%, and more preferably a population characterized by high cell viability containing more than 97-99% viable cells.

The terms "diabetes" and "diabetic" refer to a progressive disease of carbohydrate metabolism involving inadequate production or utilization of insulin, frequently characterized by hyperglycemia and glycosuria. The terms "pre-diabetes" and "pre-diabetic" refer to a state wherein a subject does not have the characteristics, symptoms and the like typically observed in diabetes, but does have characteristics, symptoms and the like that, if left untreated, may progress to diabetes. The presence of these conditions may be determined using, for example, either the fasting plasma glucose (FPG) test or the oral glucose tolerance test (OGTT). Both usually require a subject to fast for at least 8 hours prior to initiating the test. In the FPG test, a subject's blood glucose is measured after the conclusion of the fasting; generally, the subject fasts overnight and the blood glucose is measured in the morning before the subject eats. A healthy subject would generally have an FPG concentration between about 90 and about 100 mg/dl, a subject with "pre-diabetes" would generally have an FPG concentration between about 100 and about 125 mg/dl, and a subject with "diabetes" would generally have an FPG level above about 126 mg/dl. In the OGTT, a subject's blood glucose is measured after fasting and again two hours after drinking a glucose-rich beverage. Two hours after consumption of the glucose-rich beverage, a healthy subject generally has a blood glucose concentration below about 140 mg/dl, a pre-diabetic subject generally has a blood glucose concentration about 140 to about 199 mg/dl, and a diabetic subject generally has a blood glucose concentration about 200 mg/dl or above. The term “insulin resistance” as used herein refers to a condition where a normal amount of insulin is unable to produce a normal physiological or molecular response. In some cases, a hyper-physiological amount of insulin, either endogenously produced or exogenously administered, is able to overcome the insulin resistance, in whole or in part, and produce a biologic response.

As used herein, the terms “detectable label”, “imaging agent”, “diagnostic agent”, and “detectable moiety” are used interchangeably and refer to a molecule or substance capable of detection, including, but not limited to, fluorescers, chemiluminescers, chromophores, bioluminescent proteins, enzymes, enzyme substrates, enzyme cofactors, enzyme inhibitors, isotopic labels, semiconductor nanoparticles, dyes, metal ions, metal sols, ligands (e.g., biotin, streptavidin or haptens) and the like. The term “fluorescer” refers to a substance or a portion thereof which is capable of exhibiting fluorescence in the detectable range. Particular examples of detectable labels which may be used in the practice of the invention include isotopic labels, including radioactive and non-radioactive isotopes, such as, $^{3}$H, $^{2}$H, $^{120}$I, $^{123}$I, $^{124}$I, $^{125}$I, $^{131}$I, $^{35}$S, $^{11}$C, $^{13}$C, $^{14}$C, $^{32}$P, $^{15}$N, $^{13}$N, $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{154}$Gd, $^{155}$Gd, $^{156}$Gd, $^{157}$Gd, $^{158}$Gd, $^{15}$O, $^{186}$Re, $^{188}$Re, $^{51}$M, $^{52m}$Mn, $^{55}$Co, $^{72}$As, $^{75}$Br, $^{76}$Br, $^{82m}$Rb, and $^{83}$Sr. In particular, detectable labels may comprise positron-emitting radionuclides suitable for PET imaging such as, but not limited to, $^{64}$Cu, $^{89}$Zr, $^{68}$Ga, $^{177}$Lu, $^{82}$Rb, $^{11}$C, $^{13}$N, $^{15}$O, and $^{18}$F; or gamma-emitting radionuclides suitable for single photon emission computed tomography (SPECT) imaging such as, but not limited to, $^{67}$Ga, $^{99m}$Tc, $^{123}$I, and $^{131}$I. Detectable labels may also include non-radioactive, paramagnetic metal ions suitable for MRI imaging such as, but not limited to, $Mn^{2+}$, $Fe^{3+}$, $Fe^{2+}$, $Gd^{3+}$, $Ti^{2+}$, $Cr^{3+}$, $Co^{2+}$, $Ni^{2+}$, and $Cu^{2+}$. Detectable labels may also include fluorophores including without limitation, SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 350, Alexa Fluor 488, Alexa Fluor 546, Alexa Fluor 555, Alexa Fluor 594, Alexa Fluor 647, and Alexa Fluor 784, a cyanine dye such as Cy 3, Cy3.5, Cy5, Cy5.5, and Cy7, fluorescein, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), rhodamine, carboxy-X-rhodamine (ROX), tetramethyl rhodamine (TAMRA), FITC, dansyl, umbelliferone, dimethyl acridinium ester (DMAE), Texas red, luminol, and quantum dots, enzymes such as alkaline phosphatase (AP), beta-lactamase, chloramphenicol acetyltransferase (CAT), adenosine deaminase (ADA), aminoglycoside phosphotransferase ($neo^r$, $G418^r$) dihydrofolate reductase (DHFR), hygromycin-B-phosphotransferase (HPH), thymidine kinase (TK), β-galactosidase (lacZ), and xanthine guanine phosphoribosyltransferase (XGPRT), beta-glucuronidase (gus), placental alkaline phosphatase (PLAP), and secreted embryonic alkaline phosphatase (SEAP). Enzyme tags are used with their cognate substrate. The terms also include chemiluminescent labels such as luminol, isoluminol, acridinium esters, and peroxyoxalate and bioluminescent proteins such as firefly luciferase, bacterial luciferase, *Renilla* luciferase, and aequorin. The terms also include color-coded microspheres of known fluorescent light intensities (see e.g., microspheres with xMAP technology produced by Luminex (Austin, TX); microspheres containing quantum dot nanocrystals, for example, containing different ratios and combinations of quantum dot colors (e.g., Qdot nanocrystals produced by Life Technologies (Carlsbad, CA); glass coated metal nanoparticles (see e.g., SERS nanotags produced by Nanoplex Technologies, Inc. (Mountain View, CA); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), glass microparticles with digital holographic code images (see e.g., CyVera microbeads produced by Illumina (San Diego, CA), near infrared (NIR) probes, and nanoshells. The terms also include contrast agents such as ultrasound contrast agents (e.g. SonoVue microbubbles comprising sulfur hexafluoride, Optison microbubbles comprising an albumin shell and octafluoropropane gas core, Levovist microbubbles comprising a lipid/galactose shell and an air core, Perflexane lipid microspheres comprising perfluorocarbon microbubbles, and Perflutren lipid microspheres comprising octafluoropropane encapsulated in an outer lipid shell), magnetic resonance imaging (MRI) contrast agents (e.g., gadodiamide, gadobenic acid, gadopentetic acid, gadoteridol, gadofosveset, gadoversetamide, gadoxetic acid), and radiocontrast agents, such as for computed tomography (CT), radiography, or fluoroscopy (e.g., diatrizoic acid, metrizoic acid, iodamide, iotalamic acid, ioxitalamic acid, ioglicic acid, acetrizoic acid, iocarmic acid, methiodal, diodone, metrizamide, iohexol, ioxaglic acid, iopamidol, iopromide, iotrolan, ioversol, iopentol, iodixanol, iomeprol, iobitridol, ioxilan, iodoxamic acid, iotroxic acid, ioglycamic acid, adipiodone, iobenzamic acid, iopanoic acid, iocetamic acid, sodium iopodate, tyropanoic acid, and calcium iopodate). The detectable label, imaging agent, or contrast agent may be attached indirectly or directly to a nanoparticle or loaded into pores of the nanoparticle mesoporous core, wherein the label, imaging agent, or contrast agent facilitates the use of the nanoparticle in imaging.

It will be apparent to one of ordinary skill in the art that various changes and modifications can be made without departing from the spirit or scope of the invention.

Nanoparticles

Nanoparticles useful for supplying nutrients and other therapeutic agents to transplanted cells are provided. Such nanoparticles are useful in cellular therapy to improve the engraftment and survival of transplanted cells, particularly when cells become devascularized during isolation or transplantation resulting in nutrient deprivation. Accordingly, nanoparticles can be used to supply cells with nutrients and/or other therapeutic agents until the transplanted cells are able to develop a functional microcirculation.

The nanoparticles comprise a mesoporous silica ($SiO_2$) core comprising a plurality of pores that are sufficiently large to contain one or more therapeutic agents. In some embodiments, the pores in the mesoporous outer shell have an average diameter ranging from about 1 to 20 nanometers, including any average diameter within this range, such as 1, 2, 3, 4, 5, 6, 7, 8, 9, 10, 11, 12, 13, 14, 15, 16, 17, 18, 19, or 20 nm. In some embodiments, the pores have a diameter of about 2 nm or more, e.g., about nm or more, about 6 nm or more, about 8 nm or more, about 10 nm or more, about 15 nm or more, including about 18 nm or more, and may have a diameter of about 20 nm or less, e.g., about 15 nm or less, about 10 nm or less, about 8 nm or less, about 6 nm or less, including about 4 nm or less.

The nanoparticles have a suitable porosity for containing the therapeutic agents encapsulated therein such that the therapeutic agents are released from the nanoparticles in the vicinity of cells in effective amounts sufficient to allow cell survival. In some embodiments, a nanoparticle has a porosity of about 50% or more, e.g., about 60% or more, about 65% or more, about 70% or more, about 75% or more, about 80% or more, including about 85% or more, and in some cases, has a bulk porosity of about 95% or less, e.g., about 90% or less, about 85% or less, about 80% or less, including about 75% or less. In some embodiments, the nanoparticle has a porosity in the range of about 50% to about 95%, e.g., about 55% to about 90%, about 60% to about 85%, including about 65% to about 80%. In some cases, the nanoparticle has a porosity of about 70% to about 75%. The porosity may be measured, for example, using computed tomography (CT) scanning (see Examples).

In addition, the nanoparticles comprise a layer comprising polydopamine encapsulating the mesoporous silica core, wherein the thickness of the polydopamine layer is sufficient to allow sustained release of therapeutically effective amounts of the therapeutic agents from the nanoparticle for a period long enough to allow transplanted cells to survive until revascularization. Polydopamine coatings can be formed by self-polymerization of a dopamine monomer under alkaline pH conditions (see Example 2). The thickness of the layer comprising the polydopamine determines the rate of its dissolution and hence the release of the contents within the mesoporous silica core. Accordingly, the thickness of the polydopamine layer can be adjusted to provide temporal control over the release of nutrients and other therapeutic agents from the nanoparticle mesoporous silica core.

In some embodiments, the thickness of the polydopamine layer ranges from about 2 nm to about 30 nm, including any thickness within this range, such as 2, 3, 4, 5, 6, 7, 8, 9, 10, 11, 12, 13, 14, 15, 16, 17, 18, 19, 20, 21, 22, 23, 24, 25, 26, 27, 28, 29, or 30 nm. In some embodiments, the polydopamine layer has a thickness of about 2 nm or more, e.g., about 3 nm or more, about 4 nm or more, about 5 nm or more, about 8 nm or more, about 9 nm or more, about 10 nm or more, including about 15 nm or more, and may have a thickness of about 20 nm or less, e.g., about 15 nm or less, about 10 nm or less, about 8 nm or less, about 6 nm or less, about 4 nm or less, including about 3 nm or less.

In some embodiments, the nanoparticles have a diameter ranging from about 30 nm to 300 nm, including any diameter within this range, such as 30, 35, 40, 45, 50, 55, 60, 65, 70, 75, 80, 85, 90, 95, 100, 105, 110, 115, 120, 125, 150, 175, 200, 225, 250, 275, or 300 nm. In some embodiments, the nanoparticles have a diameter of about 50 nm or more, e.g., about 60 nm or more, about 80 nm or more, about 100 nm or more, about 110 nm or more, about 115 nm or more, including about 120 nm or more, and may have a diameter of about 200 nm or less, e.g., about 150 nm or less, about 130 nm or less, about 120 nm or less, about 110 nm or less, including about 100 nm or less.

The nanoparticles with therapeutic agents encapsulated therein may promote vascularization when implanted in proximity to transplanted cells at a physiological site (e.g., kidney, liver, omentum, peritoneum, abdomen, or submuscular or subcutaneous tissue) of an individual. The implantation site may be vascularized in 60 days or less, e.g., 40 days or less, 30 days or less, 20 days or less, 10 days or less, including 5 days or less after implantation of the nanoparticles with therapeutic agents encapsulated therein. In some cases, the implantation site is vascularized in 5 days to 60 days, e.g., 5 days to 40 days, including 10 days to 30 days after implantation of the nanoparticles with therapeutic agents encapsulated therein.

Nanoparticles of the present disclosure containing nutrients and/or other agents encapsulated therein can be implanted in proximity to transplanted cells at a physiological site (e.g., kidney, liver, omentum, peritoneum, abdomen, or submuscular or subcutaneous tissue) of an individual where the nanoparticles may maintain transplanted cells in a functional state suitable for providing a therapeutic effect (e.g., insulin secretion by beta-cells). The nanoparticles promote survival and maintain responsiveness of transplanted cells to physiological cues (e.g., blood glucose level) at the implantation site. Without wishing to be bound by theory, it is thought that the supply of nutrients by the nanoparticles prevents damage to cells caused by nutrient deprivation, promotes survival, and maintains the cells in a functional state following transplantation until vascular integration of the transplanted cells.

In some embodiments, the nanoparticle includes one or more nutrients and/or other agents adsorbed or absorbed within the nanoparticle or contained within the pores of the nanoparticle, wherein the nanoparticle is capable of delivering the one or more nutrients and/or other agents to cells at a site of implantation.

In some embodiments, the agent is a nutrient, such as amino acids including, but not limited to, glutamine, alanine, cysteine, tryptophan, leucine, methionine, isoleucine, arginine, lysine, proline, and homocysteine; proteins/peptides including, but not limited to, hormones, growth factors, transcription factors, enzymes, receptors, and antibodies; carbohydrates including but not limited to, monosaccharides (e.g. glucose), disaccharides, oligosaccharides, and polysaccharides; vitamins including, but not limited to, vitamin A (as all-trans-retinol, all-trans-retinyl-esters, as well as all-trans-beta-carotene and other provitamin A carotenoids), vitamin 1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (phylloquinone and menaquinones); and lipids including, but not limited to, fatty acids, triglycerides, phospholipids, and sterols and related compounds (e.g., steroids, cholesterol, and cholesteryl esters).

In some embodiments, the agent is an antioxidant, such as, but not limited to, thiols (e.g., glutathione, dithiothreitol, and β-mercaptoethanol), ascorbic acid, carotenes (e.g., β-carotene and retinol), tocopherols (e.g., α-tocopherol), tocotrienols, lipoic acid, uric acid, and ubiquinone.

In some embodiments, the agent is an immunosuppressant, such as, but not limited to cyclosporine and tacrolimus. In some cases, the agent is an inhibitor of the mammalian target of rapamycin (mTOR), such as, without limitation, rapamycin and analogs thereof (e.g., sirolimus, temsirolimus, everolimus, deforolimus, etc.). The mTOR inhibitor may be used as an immunosuppressant, or may be an anticancer agent.

In some embodiments, the agent is an antibody, or an antigen binding fragment thereof. For example, the antibody may be any suitable antibody that specifically binds to an antigen expressed by a therapeutic cell of interest. Suitable antigens include, without limitation, CD3, CD28, CD137, CTLA-4, TNF, IL-6, IL-12, PD-1, PD-L1, TIM3, LAG3, IL-2Ralpha, IL-23, IL-6R, CD25, IL-17, IL-1, CD4, CD8, LFA-1, IL-22, and IL-20.

Other agents may include, but are not limited to, interferon, interleukin, erythropoietin, granulocyte-colony stimulating factor (GCSF), stem cell factor (SCI:), leptin (OB protein), interferon (alpha, beta, gamma), antibiotics such as vancomycin, gentamicin ciprofloxacin, amoxycillin, lactobacillus, cefotaxime, levofloxacin, cefipime, mebendazole, ampicillin, lactobacillus, cloxacillin, norfloxacin, tinidazole, cefpodoxime, proxctil, azithromycin, gatifloxacin, roxithromycin, cephalosporin, anti-thrombogenics, aspirin, ticlopidine, sulfinpyrazone, heparin, warfarin, growth factors, differentiation factors, hepatocyte stimulating factor, plasmacytoma growth factor, glial derived neurotrophic factor (GDNF), neurotrophic factor 3 (NT3), fibroblast growth factor (FGF), transforming growth factor (TGF), platelet transforming growth factor, milk growth factor, endothelial growth factors, endothelial cell-derived growth factors (ECDGF), alpha-endothelial growth factors, beta-endothelial growth factor, neurotrophic growth factor, nerve growth factor (NGF), vascular endothelial growth factor (VEGF), 4-1 BB receptor (4-IBBR), TRAIL (TNF-related apoptosis inducing ligand), artemin (GFRalpha3-RET ligand), BCA-I (B cell-attracting chemokinel), B lymphocyte chemoattractant (BLC), B cell maturation protein (BCMA), brain-derived neurotrophic factor (BDNF), bone growth factor such as osteoprotegerin (OPG), bone-derived growth factor, thrombopoietin, megakaryocyte derived growth factor (MDGF), keratinocyte growth factor (KGF), platelet-derived growth factor (PDGF), ciliary neurotrophic factor (CNTF), neurotrophin 4 (NT4), granulocyte colony-stimulating factor (GCSF), macrophage colony-stimulating factor (mCSF), bone morphogenetic protein 2 (BMP2), BRAK, C-10, Cardiotrophin 1 (CTI), CCR8, anti-inflammatory: paracetamol, salsalate, diflunisal, mefenamic acid, diclofenac, piroxicam, ketoprofen, dipyrone, acetylsalicylic acid, anti-cancer drugs such as aliteretinoin, altertamine, anastrozole, azathioprine, bicalutarnide, busulfan, capecitabine, carboplatin, cisplatin, cyclophosphamide, cytarabine, doxorubicin, epirubicin, etoposide, exemestane, vincristine, vinorelbine, hormones, thyroid stimulating hormone (TSH), sex hormone binding globulin (SHBG), prolactin, luteotropic hormone (LTH), lactogenic hormone, parathyroid hormone (PTH), melanin concentrating hormone (MCH), luteinizing hormone (LHb), growth hormone (HGH), follicle stimulating hormone (FSHb), haloperidol, indomethacin, doxorubicin, epirubicin, amphotericin B, taxol, cyclophosphamide, cisplatin, methotrexate, pyrene, amphotericin B, anti-dyskinesia agents, Alzheimer's disease vaccine, anti-Parkinson agents, ions, edetic acid, nutrients, glucocorticoids, heparin, anticoagulation agents, antivirus agents, anti-HIV agents, polyamine, histamine and derivatives thereof, cystineamine and derivatives thereof, diphenhydramine and derivatives, orphenadrine and derivatives, muscarinic antagonist, phenoxybenzamine and derivatives thereof, protein A, streptavidin, amino acid, beta-galactosidase, methylene blue, protein kinases, beta-amyloid, lipopolysaccharides, eukaryotic initiation factor-4G, tumor necrosis factor (TNF), tumor necrosis factor-binding protein (TNF-bp), interleukins (1 to 18) receptor antagonist (IL-Ira), granulocyte macrophage colony stimulating factor (GM-CSF), novel erythropoiesis stimulating protein (NESP), thrombopoietin, tissue plasminogen activator (TPA), urokinase, streptokinase, kallikrein, insulin, steroid, acetaminophen, analgesics, antitumor preparations, anti-cancer preparations, anti-proliferative preparations or pro-apoptotic preparations, among other types of active agents.

In some embodiments, the one or more agents include a compound selected from the group consisting of chemotactic agents, cell attachment mediators, integrin binding sequences, epidermal growth factor (EGF), hepatocyte growth factor (HGF), vascular endothelial growth factors (VEGF), fibroblast growth factors, platelet derived growth factors (PDGF), insulin-like growth factor, transforming growth factors (TGF), parathyroid hormone, parathyroid hormone related peptide, bone morphogenetic proteins (BMP), BMP-2, BMP-4, BMP-6, BMP-7, BMP-12, BMP-13, BMP-14, transcription factors, growth differentiation factor (GDF), GDF5, GDF6, GDF8, recombinant human growth factors, cartilage-derived morphogenetic proteins (CDMP), CDMP-1, CDMP-2 and CDMP-3.

In some embodiments, the nanoparticle is further loaded or conjugated with one or more imaging agents for use in medical imaging. For example, the nanoparticle may comprise a positron-emitting metal radionuclide suitable for PET imaging such as $^{64}Cu$, $^{68}Ga$, $^{44}Sc$, $^{86}Y$, $^{89}Zr$, or $^{82}Rb$; a gamma-emitting metal radionuclide suitable for single photon emission computed tomography (SPECT) imaging such as $^{67}Ga$, $^{99m}Tc$, $^{111}In$, or $^{177}Lu$, or a paramagnetic metal ion suitable for MRI such as paramagnetic ions of manganese (e.g., $Mn^{2+}$), iron (e.g., $Fe^{3+}$, $Fe^{2+}$) or gadolinium (e.g., $Gd^{3+}$). Alternatively, the nanoparticle can be loaded or conjugated with suitable contrast agents for medical imaging such as magnetic resonance imaging (MRI) contrast agents (e.g., gadodiamide, gadobenic acid, gadopentetic acid, gadoteridol, gadofosveset, gadoversetamide, gadoxetic acid), and radiocontrast agents, such as for computed tomography (CT), radiography, or fluoroscopy (e.g., diatrizoic acid, metrizoic acid, iodamide, iotalamic acid, ioxitalamic acid, ioglicic acid, acetrizoic acid, iocarmic acid, methiodal, diodone, metrizamide, iohexol, ioxaglic acid, iopamidol, iopromide, iotrolan, ioversol, iopentol, iodixanol, iomeprol, iobitridol, ioxilan, iodoxamic acid, iotroxic acid, ioglycamic acid, adipiodone, iobenzamic acid, iopanoic acid, iocetamic acid, sodium iopodate, tyropanoic acid, and calcium iopodate).

Pharmaceutical Compositions

Nanoparticles can be formulated into pharmaceutical compositions optionally comprising one or more pharmaceutically acceptable excipients. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerin, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the nanoparticle or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (BASF, Mount Olive, New Jersey); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, NJ (1998), and Kibbe, A. H., Handbook of Pharmaceutical Excipients, 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral or localized delivery.

The pharmaceutical preparations herein can also be housed in a syringe, an implantation device, or the like, depending upon the intended mode of delivery and use. Preferably, the compositions comprising nanoparticles described herein are in unit dosage form, meaning an amount of nanoparticles appropriate for a single dose, in a premeasured or pre-packaged form.

The compositions herein may optionally include one or more additional agents, such as anti-inflammatory, immunosuppressive, analgesic, or chemotherapeutic drugs or other medications used to treat a subject for a condition or disease. For example, compounded preparations may include nanoparticles and one or more drugs for treating a condition or disease. Alternatively, such agents can be contained in a separate composition from the composition comprising the nanoparticles and co-administered concurrently, before, or after the composition comprising the nanoparticles.

Methods of Transplanting Cells in Combination with Nanoparticles into an Individual Also provided herein is a method of transplanting cells into an individual in combination with the nanoparticles, described herein, wherein the nanoparticles supply nutrients and/or other therapeutic agents to the transplanted cells. The method may include implanting (e.g., injecting or surgically implanting) the nanoparticles containing the nutrients and/or other therapeutic agents in proximity to the transplanted cells at a transplantation site of a host individual. The host individual may be suffering from a condition, e.g., a disease, that may be treated by providing the therapeutic cells to the individual. In some cases, the disease is diabetes (type 1 or type 2). In some cases, the individual has pre-diabetes, or hyperglycemia. In some cases, the disease is arthritis (e.g., osteoarthritis). In some cases, the disease is cancer (e.g., breast cancer, ovarian cancer, prostate cancer, brain cancer, skin cancer, lung cancer, liver cancer, colorectal cancer, etc.). The therapeutic cells may be any suitable therapeutic cells, and the type of therapeutic cells may depend on the disease to be treated.

The implantation site may be any suitable location (e.g., surgically accessible location) in the individual. For example, for treatment of diabetes, the implantation site may be in a kidney, liver, omentum, peritoneum, abdomen, or submuscular or subcutaneous tissue. For treatment of arthritis, the implantation site may be in an arthritic joint. For treatment of cancer, the implantation site may be at or in the vicinity of a tumor or cancerous cells.

The nanoparticles provide nutrients and/or other therapeutic agents at the implantation site for a sufficient period of time to allow vascularization at the implantation site to occur (i.e., until creation of a permanent blood supply carrying nutrients and other factors to the transplanted therapeutic cells). The period of time may be 50 days or less, e.g., 40 days or less, 35 days or less, 30 days or less, including 20 days or less. In some cases, the period is in the range of 14 days to 50 days, e.g., 14 days to 40 days, 14 days to 30 days, including 14 days to 20 days.

In some cases, implanting the nanoparticles may be performed concurrently with transplanting the therapeutic cells at the transplantation site (e.g., with the nanoparticles and therapeutic cells in the same composition). Alternatively, the nanoparticles may be contained in a separate composition from the therapeutic cells and implanted in proximity to the therapeutic cells shortly before or after transplanting the therapeutic cells at the transplantation site as long as the nanoparticles are implanted in time to prevent cell death from nutrient deprivation (i.e., improve survival by suppling the transplanted cells with nutrients and/or other therapeutic agents). In some cases, implanting the nanoparticles may be performed in conjunction with another therapy, such as a surgical operation and/or administration of a drug. In some cases, the nanoparticles are implanted at the transplantation site after a surgical operation, e.g., to remove a tumor or malignant tissue from the implantation site.

The therapeutic cells may be any suitable type of cell for transplanting to an individual in need. The therapeutic cells may be stem cells, progenitor cells, or mature cells. The cells may be autologous, allogeneic, xenogeneic or genetically-modified. In some embodiments, the therapeutic cells include cells that secrete a biological agent, e.g., a signaling molecule, a hormone, a growth factor, a cytokine, a chemokine, an enzyme, an antibody, etc. In some cases, the therapeutic cells include cells (e.g., immune cells, such as cytotoxic T lymphocytes) that interact with targets at or in the vicinity in the host tissue in which the cells and nanoparticles are implanted. In some cases, the therapeutic cells include cells whose activity is conditional, e.g., cells that modulate their function based on the physiological state of the host, such as glucose level in the blood and/or the environment of the host tissue. The therapeutic cell may be a type of cell that specifically possesses the functional activity by virtue of its cell type (e.g., by differentiating or having differentiated into a cell type that exhibits the functional activity), or may be genetically modified to exhibit the functional activity that was not exhibited by the cell before being genetically modified.

Exemplary therapeutic molecules that can be secreted by a therapeutic cell include, without limitation, insulin, human growth hormone, thyroxine, glucagon-like peptide-1 (GLP-1), GLP-1 (7-37), GLP-1 (7-36), and like GLP-1 receptor agonist polypeptides, GLP-2, interleukins 1 to 33 (e.g., IL-1, IL-2, IL-3, IL-4, IL-5, IL-6, IL-7, IL-8, IL-9, IL-10, IL-11, IL-12, IL-13, IL-17, IL-18, IL-21, IL-22, IL-27, IL-33), interferon (α, β, γ), GM-CSF, G-CSF, M-CSF, SCF, FAS ligands, TRAIL, leptin, adiponectin, blood coagulation factor VIII/blood coagulation factor IX, von Willebrand factor, glucocerebrosidase, lipoprotein lipase (LPL), lecithin-cholesterol acyltransferase (LCAT), erythropoietin, apoA-1, albumin, atrial natriuretic peptide (ANP), luteinizing hormone releasing hormone (LHRH), angiostatin/endostatin, endogenous opioid peptides (enkephalins, endorphins, etc.), calcitonin/bone morphogenetic protein (BMP), pancreatic secretory trypsin inhibitors, catalase, superoxide dismutase, anti-TNF-α antibody, soluble IL-6 receptor, IL-1 receptor antagonist, α2 antitrypsin, etc.

In some cases, the therapeutic cells are stem cell-derived cells. Stem cells of interest include, without limitation, hematopoietic stem cells, embryonic stem cells, adult stem cells, mesenchymal stem cells, neural stem cells, epidermal stem cells, endothelial stem cells, gastrointestinal stem cells, liver stem cells, cord blood stem cells, amniotic fluid stem cells, skeletal muscle stem cells, smooth muscle stem cells (e.g., cardiac smooth muscle stem cells), pancreatic stem cells, olfactory stem cells, induced pluripotent stem cells; and the like; as well as differentiated cells that can be cultured in vitro and used in a therapeutic regimen, where such cells include, but are not limited to, keratinocytes, adipocytes, cardiomyocytes, neurons, osteoblasts, pancreatic islet cells, retinal cells, and the like. The cell that is used will depend in part on the nature of the disorder or condition to be treated.

Suitable human embryonic stem (ES) cells include, but are not limited to, any of a variety of available human ES lines, e.g., BG01 (hESBGN-01), BGO2 (hESBGN-02), BG03 (hESBGN-03) (BresaGen, Inc.; Athens, Ga.); SA01 (Sahlgrenska 1), SA02 (Sahlgrenska 2) (Cellartis AB; Goeteborg, Sweden); ESO1 (HES-1), ESO1 (HES-2), ES03 (HES-3), ES04 (HES-4), ES05 (HES-5), ES06 (HES-6) (ES Cell International; Singapore); UC01 (HSF-1), UC06 (HSF-6) (University of California, San Francisco; San Francisco, Calif.); WA01 (H1), WA07 (H7), WA09 (H9), WA09/Oct4D10 (H9-hOct4-pGZ), WA13 (H13), WA14 (H14) (Wisconsin Alumni Research Foundation; WARF; Madison, Wis.). Cell line designations are given as the National Institutes of Health (NIll) code, followed in parentheses by the provider code.

Hematopoietic stem cells (HSCs) are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

Mesenchymal stem cells (MSCs) can be obtained from connective tissue including, without limitation, bone marrow, placenta, umbilical cord blood, adipose tissue, muscle, corneal stroma, and dental pulp of deciduous baby teeth. MSCs can differentiate to form muscle, bone, cartilage, fat, marrow stroma, and tendon. Methods of isolating MSCs are known in the art; and any known method can be used to obtain MSCs.

An induced pluripotent stem (iPS) cell is a pluripotent stem cell induced from a somatic cell, e.g., a differentiated somatic cell. iPS cells are capable of self-renewal and differentiation into cell fate-committed stem cells, including neural stem cells, as well as various types of mature cells. iPS cells can be generated from somatic cells, including skin fibroblasts, using, e.g., known methods. iPS cells can be generated from somatic cells (e.g., skin fibroblasts) by genetically modifying the somatic cells with one or more expression constructs encoding Oct-3/4 and Sox2. In some embodiments, somatic cells are genetically modified with one or more expression constructs comprising nucleotide sequences encoding Oct-3/4, Sox2, c-myc, and K1f4. In some embodiments, somatic cells are genetically modified with one or more expression constructs comprising nucleotide sequences encoding Oct-4, Sox2, Nanog, and LIN28. Methods of generating iPS are known in the art, and any such method can be used to generate iPS.

In some cases, the therapeutic cells are lymphocytes, such as CD4+ and/or CD8+T lymphocytes, or B lymphocytes. In some embodiments, the therapeutic cells are cytotoxic T lymphocytes. In some embodiments, the lymphocytes are genetically modified lymphocytes, e.g., chimeric antigen receptor (CAR) T lymphocytes. The lymphocytes, e.g., cytotoxic T lymphocytes, may specifically recognize an antigen that is associated with a disease, e.g., cancer or tumor, that is to be treated with the nanoparticles.

In some embodiments, the therapeutic cells include insulin-secreting cells. The insulin-secreting cells may be any suitable type of insulin-secreting cell. In some cases, the insulin-secreting cells are a type of cell that secretes insulin (e.g., pancreatic β islet cells, or β-like cells). In some cases, the insulin-secreting cells are primary β islet cells (e.g., mature β islet cells isolated from a pancreas). In some cases, the insulin-secreting cells are β cells, or β-like cells that are derived in vitro from immature cells, precursor cells, progenitor cells, or stem cells. The insulin-secreting cells may be derived from (i.e., obtained by differentiating) stem and/or progenitor cells such as hepatocytes (e.g., transdifferentiated hepatocytes), acinar cells, pancreatic duct cells, stem cells, embryonic stem cells (ES), partially differentiated stem cells, non-pluripotent stem cells, pluripotent stem cells, induced pluripotent stem cells (iPS cells), etc. Suitable insulin-secreting cells and methods of generating the same are described in, e.g., US20030082810; US20120141436; and Raikwar et al. (PLoS One. 2015 Jan. 28; 10(1): e0116582), each of which are incorporated herein by reference.

The insulin-secreting cells may produce (e.g., secrete) insulin at a rate independent of the ambient/extracellular glucose concentration (e.g., the concentration of glucose in the host tissue in which the nanoparticles are implanted), or may produce (e.g., secrete) insulin at a rate that depends on the ambient/extracellular glucose concentration. In some cases, the insulin-secreting cells constitutively secrete insulin. In some embodiments, the insulin-secreting cells increase insulin secretion when the ambient/extracellular glucose concentration increases, and decrease insulin secretion when the ambient/extracellular glucose concentration decreases.

Also provided herein is a method of regulating blood glucose levels in an individual using nanoparticles in combination with insulin-secreting cells. The present method may include implanting nanoparticles comprising nutrients (e.g., amino acids including at least glutamine) encapsulated therein into an implantation site (e.g., site in a kidney, liver, omentum, peritoneum, abdomen, or submuscular or subcutaneous tissue) of a host individual in proximity to transplanted insulin-secreting cells to maintain normoglycemia in the individual. The individual may be suffering from dysregulation of blood glucose, and may have, e.g., type 1 or type 2 diabetes, pre-diabetes, or hyperglycemia. The insulin-secreting cells may be any suitable insulin-secreting cells, as described above.

A medical practitioner may locate the site for implantation of nanoparticles (e.g., in proximity to transplanted therapeutic cells), for example, by medical imaging (e.g. ultrasound, radiography, or MRI). In some embodiments, a contrast agent is included in the composition comprising the nanoparticles and/or therapeutic cells to allow confirmation of the location of the nanoparticles and/or therapeutic cells by medical imaging after implantation. In some embodiments, the contrast agent is a microbubble (e.g., for use in ultrasound) or a radiopaque contrast agent (e.g., for use in radiography). The contrast agent may be contained in the same composition as the nanoparticles and/or therapeutic cells or in a different composition and used prior to or after implantation of the nanoparticles and/or therapeutic cells.

A therapeutically effective amount of a composition comprising nanoparticles is administered to a subject; that is, an amount that supplies an effective amount of the nutrients and/or other therapeutic agents encapsulated therein (e.g., contained in the pores of the nanoparticles) for a period of time sufficient to allow survival of transplanted cells until the transplanted cells develop a functional microcirculation.

A therapeutically effective amount of the nanoparticles may be administered in more than one injection if needed. The therapeutically effective amount of the nanoparticles needed for an individual may vary according to factors such as the degree of uptake of the nanoparticles into a tissue of interest (e.g., transplantation site), the particular disease for which an individual is undergoing treatment, the types of nutrients and/or other therapeutic agents encapsulated in the nanoparticles, the therapeutic cells used in combination with the nanoparticles to treat the condition, and the age, sex, and weight of the individual. Optimization of such factors is within the level of skill in the art.

The compositions comprising nanoparticles are typically, though not necessarily, administered via injection (subcutaneously, intravenously, or intramuscularly), by infusion, or locally. Additional modes of administration are also contemplated, such as oral, intra-arterial, intraperitoneal, pulmonary, nasal, topical, transdermal, intralesion, intrapleural, intraparenchymatous, rectal, transdermal, transmucosal, intrathecal, pericardial, intraocular, and so forth. When administering the nanoparticles by injection, the administration may be by continuous infusion or by single or multiple boluses.

The preparations are also suitable for local treatment. In a particular embodiment, a composition comprising nanoparticles is used for localized delivery at a transplantation site. For example, compositions comprising nanoparticles may be administered in proximity to transplanted cells to supply the cells with nutrients and/or other factors needed for survival of the transplanted cells at the transplantation site. Administration may be, for example, by surgical implantation, perfusion through a regional catheter, or direct injection.

The pharmaceutical preparation can be in the form of a liquid solution or suspension immediately prior to administration, but may also take another form such as a syrup, cream, ointment, tablet, capsule, powder, gel, matrix, suppository, or the like. The pharmaceutical compositions comprising nanoparticles may be administered in accordance with any medically acceptable method known in the art.

Kits

Kits comprising nanoparticles are also provided. In some embodiments, the kit comprises a nanoparticle encapsulating one or more therapeutic agents that can be supplied to transplanted cells at least until the cells develop a functional microcirculation. For example, the nanoparticles, included in the kit, may comprise one or more nutrients, small molecules, drugs, exosomes, antioxidants, vitamins, or other therapeutic agents encapsulated in the pores of the nanoparticles. In some embodiments, an imaging agent is encapsulated in or conjugated to the nanoparticle.

In some cases, the kit further contains cells, e.g., therapeutic cells, or a precursor thereof, suitable for transplantation in combination with the nanoparticles. In certain embodiments, the kit comprises nanoparticles in combination with insulin-secreting cells (e.g., pancreatic beta cells or islets from a donor, or insulin-secreting cells derived from stem cells or pancreatic progenitor cells), as described herein, and instructions for treating diabetes or hyperglycemia. In some embodiments, the one or more therapeutic agents, encapsulated in the nanoparticles for treating diabetes or hyperglycemia comprise at least glutamine.

The kit may also include a packaging that includes a compartment, e.g., a sterile compartment, for holding the nanoparticles or therapeutic cells. Compositions comprising nanoparticles can be suspended in a liquid or can be lyophilized. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle). The kit can further comprise a container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may also provide a delivery device pre-filled with the nanoparticles.

In addition to the above components, the subject kits may further include (in certain embodiments) instructions for practicing the subject methods (i.e., instructions for transplanting cells in combination with nanoparticles supplying nutrients and/or other therapeutic agents, as described herein). These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), DVD, Blu-ray, flash drive, and the like, on which the information has been recorded. Yet another form of these instructions that may be present is a website address which may be used via the internet to access the information at a removed site.

UTILITY

The nanoparticles find many uses where it is desirable to transplant a population of therapeutic cells into an individual to treat a condition, e.g., a disease. As described herein, a variety of types of agents such as nutrients, small molecules, drugs, exosomes, antioxidants, vitamins, and other therapeutic agents can be loaded into a nanoparticle, which is implanted in proximity to transplanted therapeutic cells to provide nutrients and/or other agents conducive for survival, growth and functional activity of the therapeutic cells in an in vivo environment of a transplant host. In some embodiments, the nanoparticle is designed with a layer comprising a biocompatible polymer (e.g., polydopamine) coating the nanoparticle that degrades at a sufficiently slow rate to retain the nutrients and/or other therapeutic agents in the nanoparticle over the desired duration of time, i.e., to allow sustained release of the nutrients and/or other therapeutic agents from the nanoparticle at least until the transplanted cells develop a functional microcirculation.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Controlled Nutrient Delivery to Pancreatic Islets Using Polydopamine Coated Mesoporous Silica Nanoparticles

Introduction

One of the main nutrients required by pancreatic islets are amino acids, including glutamine,[7-11] alanine,[7-10] cysteine,[9] tryptophan,[9,12] leucine,[9,10] methionine,[9] isoleucine,[13] arginine,[13,14] lysine,[10] proline,[10] and homocysteine[10] (Table 1). These amino acids have been shown to be essential for islet function given their role as precursors of protein synthesis, and their ability to regulate gene expression, provide energy and stimulate insulin secretion.[7,15] In the present study, we focused on glutamine ($C_5H_{10}N_2O_3$) given that, (i) it is one of the most abundant amino acids in plasma;[16] (ii) islets have a high demand and consumption rate for this amino acid;[17] and (iii) it enhances islet function through the tricarboxylic acid (TCA) cycle where it controls insulin secretion.[7] Given that islets need a continual supply of glutamine, over 2 weeks (i.e. the time it takes for islets to build a dedicated blood supply), we designed a mesoporous silica nanoparticle (MSNP) platform that can be loaded with glutamine using a simple, scalable cost-effective, and controllable procedure.[18] To avoid this burst release from MSNPs, surface coating strategies are therefore required. One approach is to apply a layer of polydopamine[19], given that studies have shown that the rate at which polydopamine degrades can be modulated by controlling the thickness of its layer. Hence, by coating MSNPs with polydopamine, and determining the correct coating concentration and time to enable it to degrade over a defined time frame, we can now control the release of glutamine loaded into MSNPs thereby preventing its immediate burst release.[20]

Figure 1A:
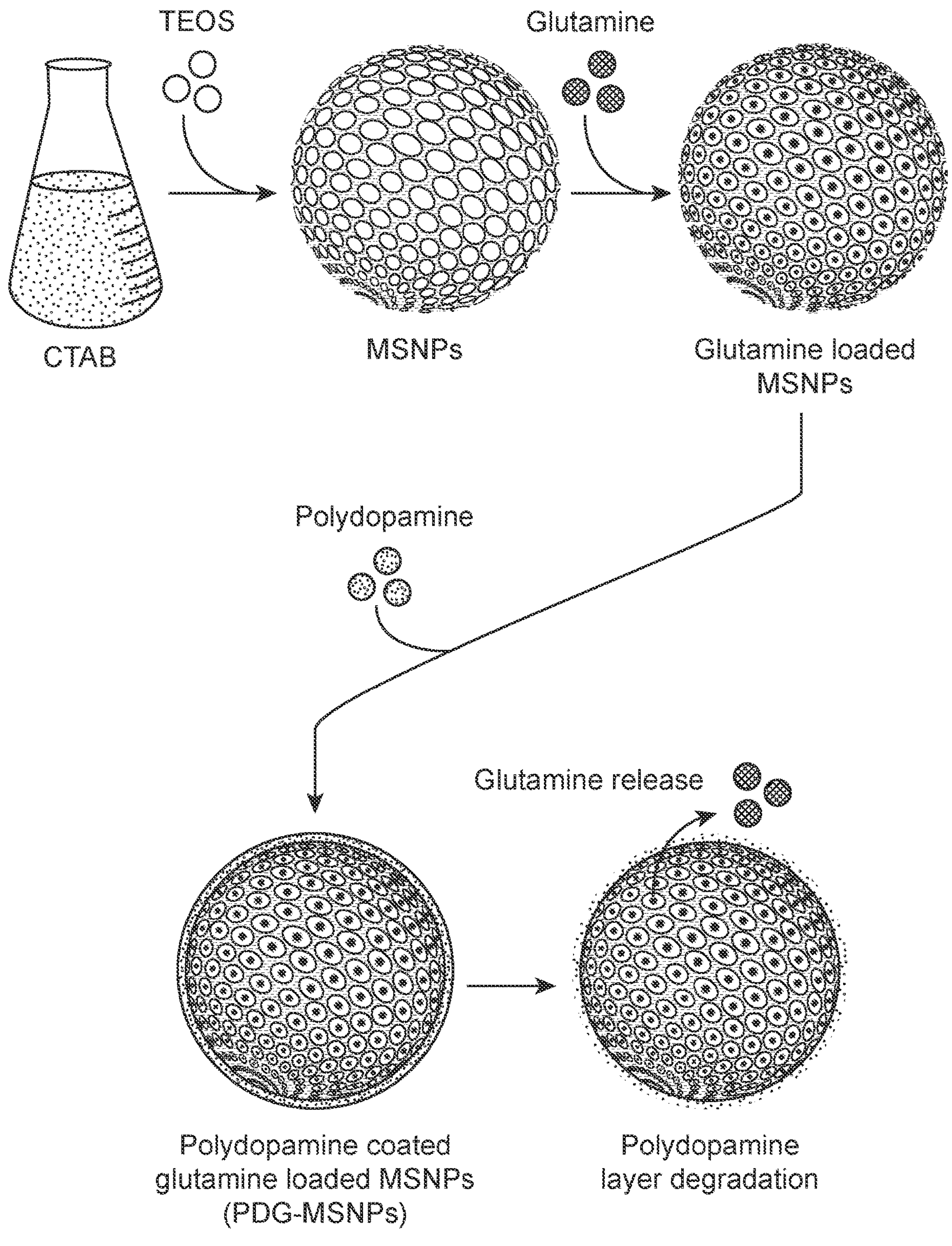
FIGS. 1A-1K. Synthesis, physical-chemical characterization and release profile of PDG-MSNPs.

Several types of nanoparticles have been used in conjunction with islet transplantation, either for in vivo imaging of islets such as poly(lactic-co-glycolic acid) nanoparticles containing iron oxide[21] and exendin-4 conjugated iron oxide[22], or for controlled immunosuppressant delivery such as poly(lactide-co-glycolide)-poly(ethylene glycol) nanoparticles[23], and amphiphilic poly(D,L-lactide-co-glycolide)-block-poly(ethylene glycol) (PLGA-b-PEG-COOH) co-polymer nanoparticles. However, to our knowledge, nanoplatforms have yet to be used for controlled nutrient delivery to islets. Hence, in the present study we synthesized a nanoparticle platform based on MSNPs that can be loaded with glutamine (G) and then coated with polydopamine (PD) to create PDG-MSNPs (FIG. 1A). Next we optimized the coating parameters to ensure a sustained release of our cargo (i.e. G) from PDG-MSNPs over 2 weeks (i.e. the required time for islets to get revascularized following their transplantation[24]) and then tested this platform on islets in vitro as well as in vivo in a diabetic animal model.

Results and Discussion

Figure 1B:
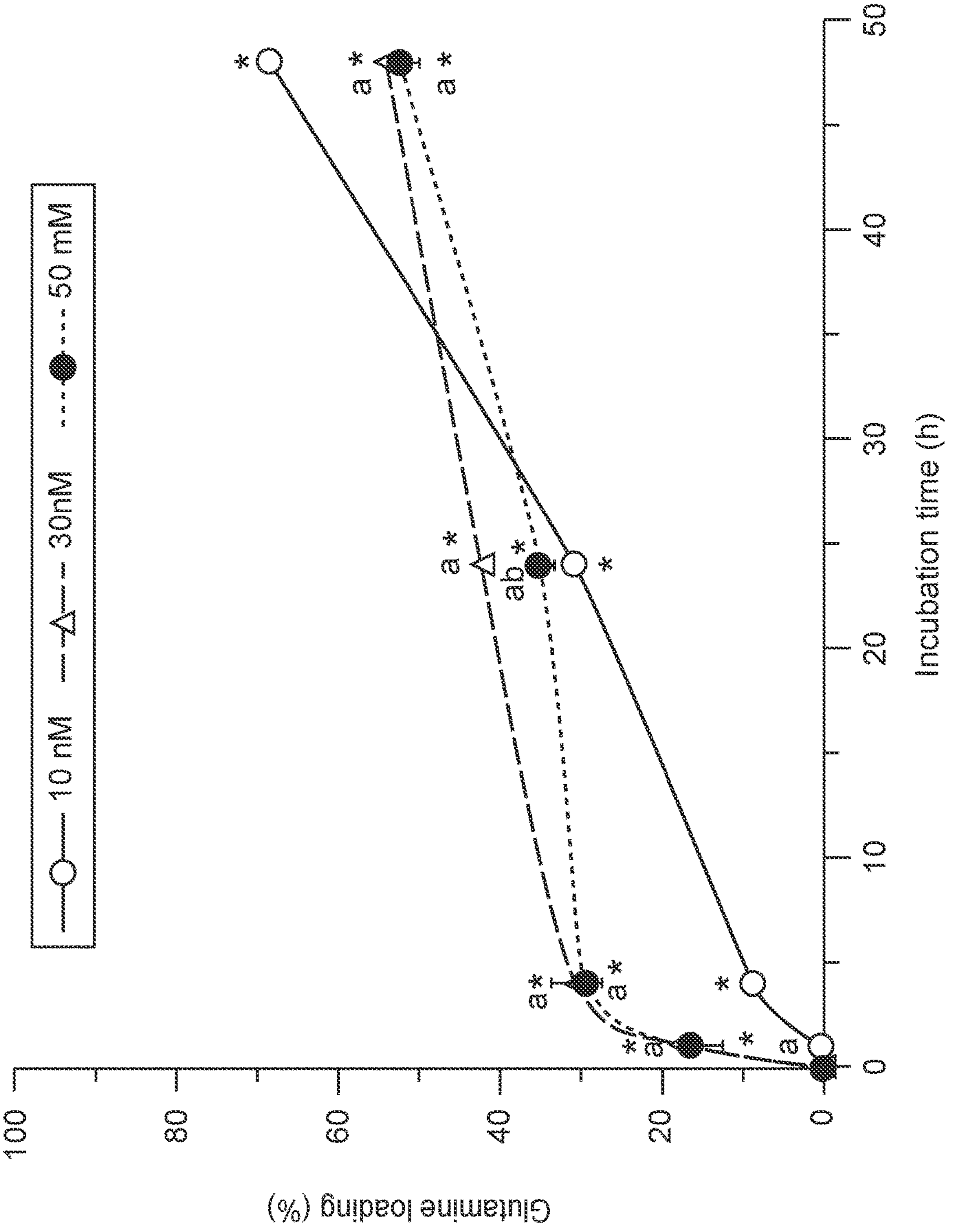

MSNPs loaded with glutamine showed a dose- and time-dependent cumulative loading profile. Incubation of MSNPs with 10 mM of glutamine, for 4 h, resulted in loading of 8.7±0.8% of glutamine into nanoparticles. By increasing the glutamine concentration from 10 to 50 mM, there was a significant increase in the amount of glutamine loaded into MSNPs in 4 h (29.4±2.0%; $p<0.05$). Furthermore, by increasing the loading time from 4 to 48 h, the cumulative amount of glutamine loaded into MSNPs significantly increased at all concentrations (FIG. 1B; $p<0.05$).

Figure 1C:
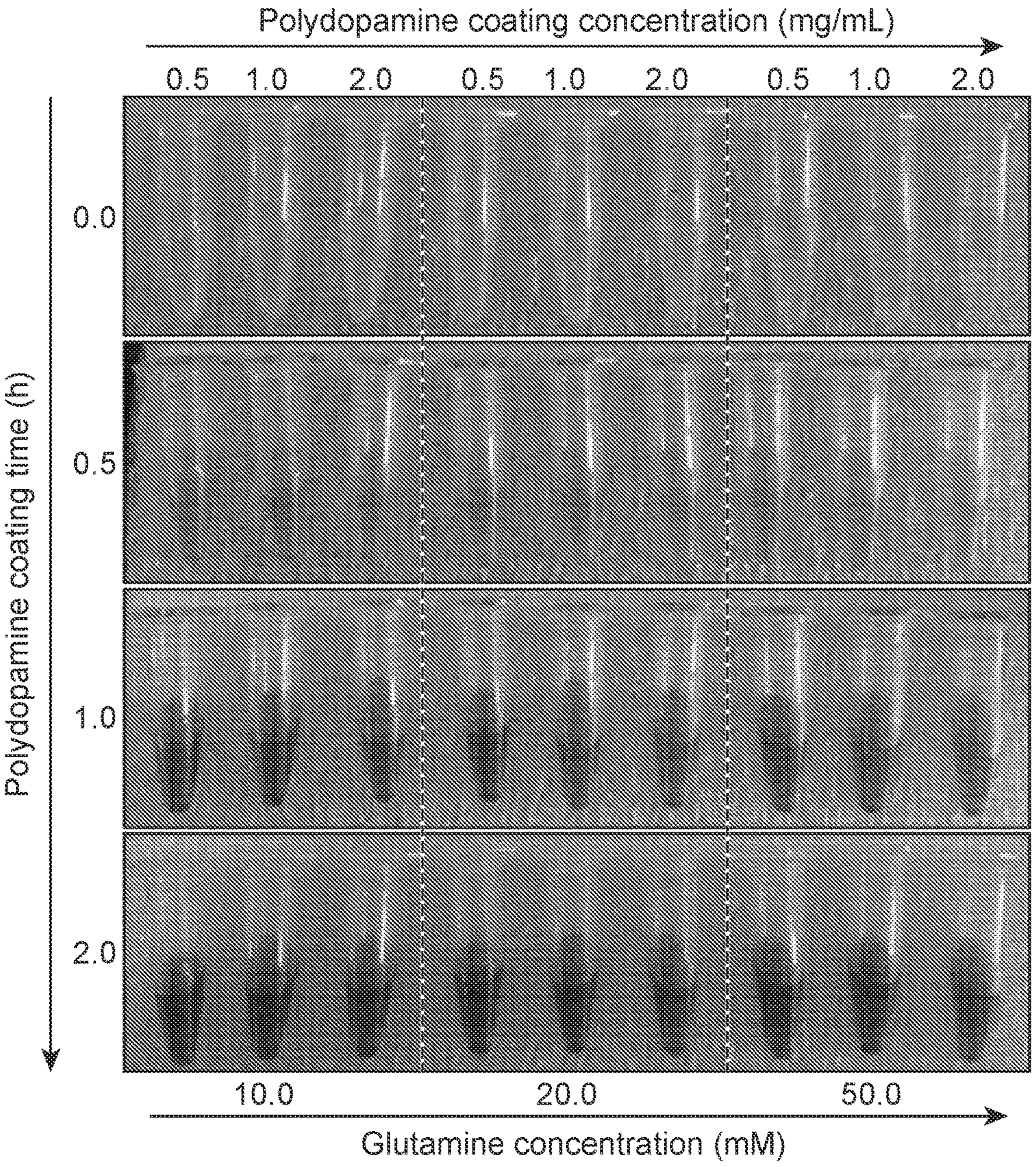
Figure 1D:
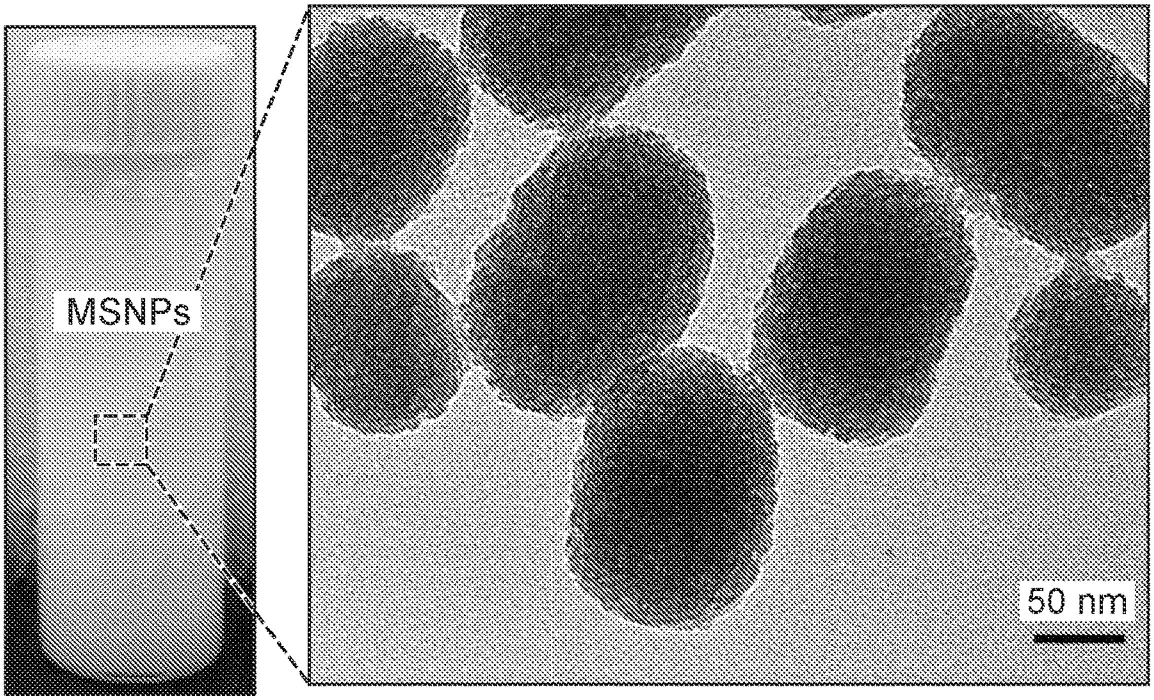
Figure 1E:
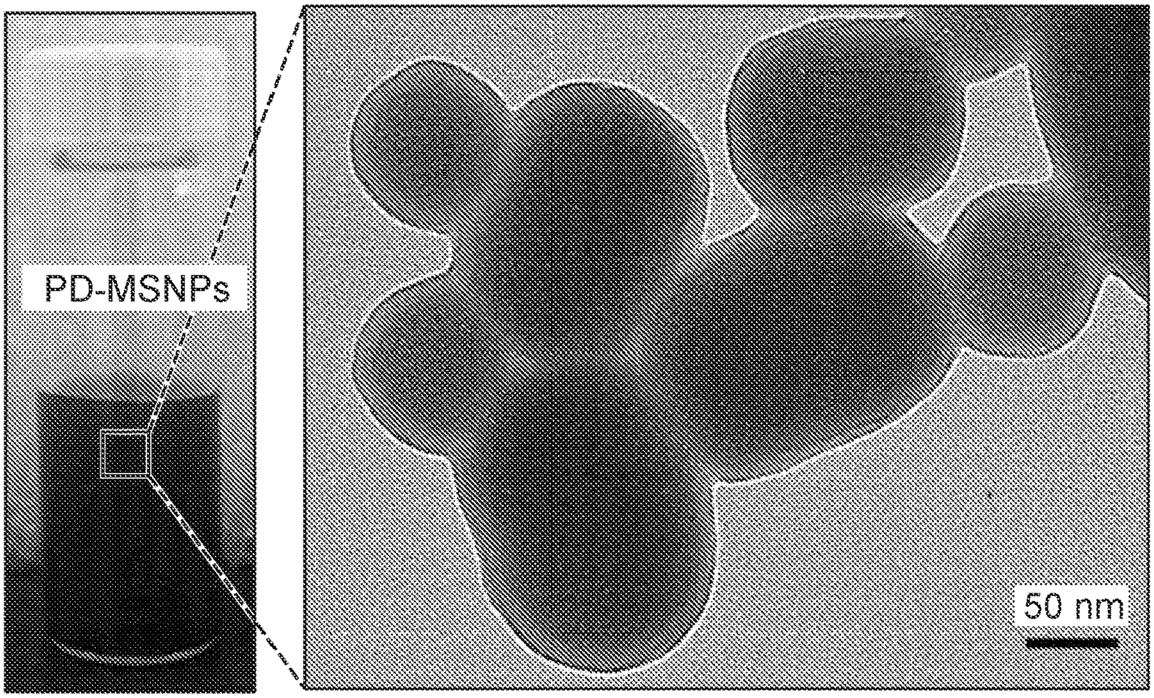
Figure 1F:
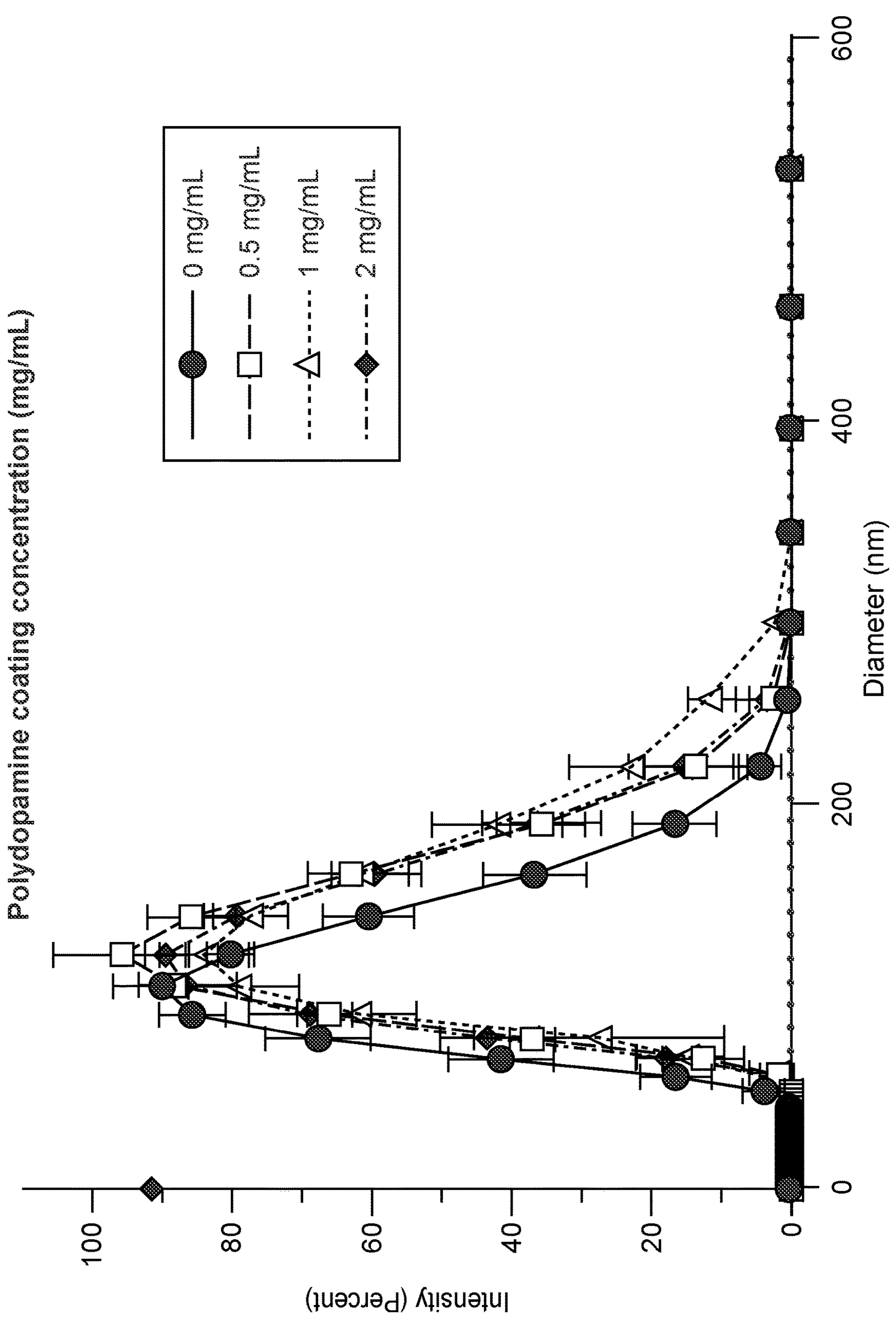
Figure 1G:
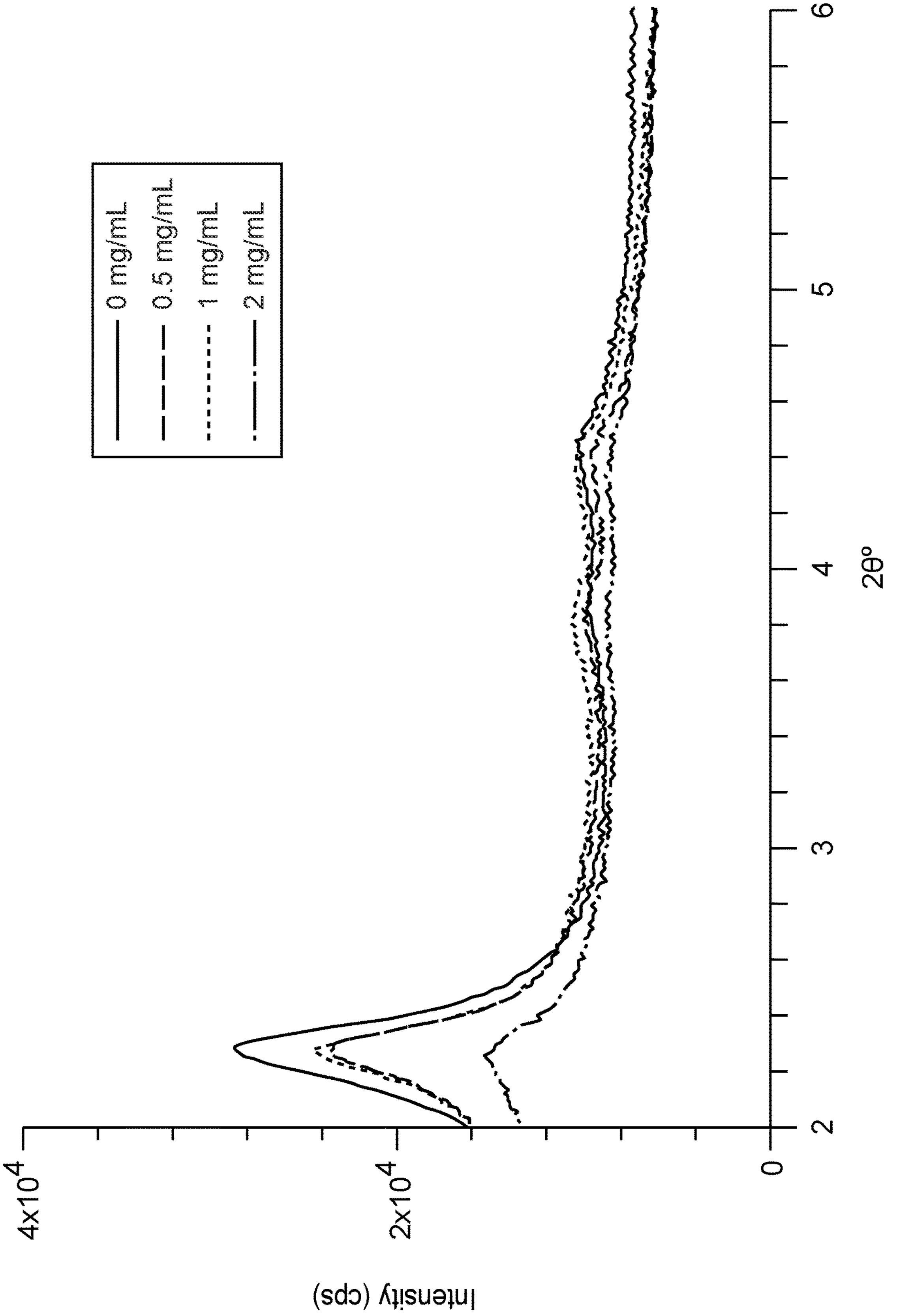
Figure 1H:
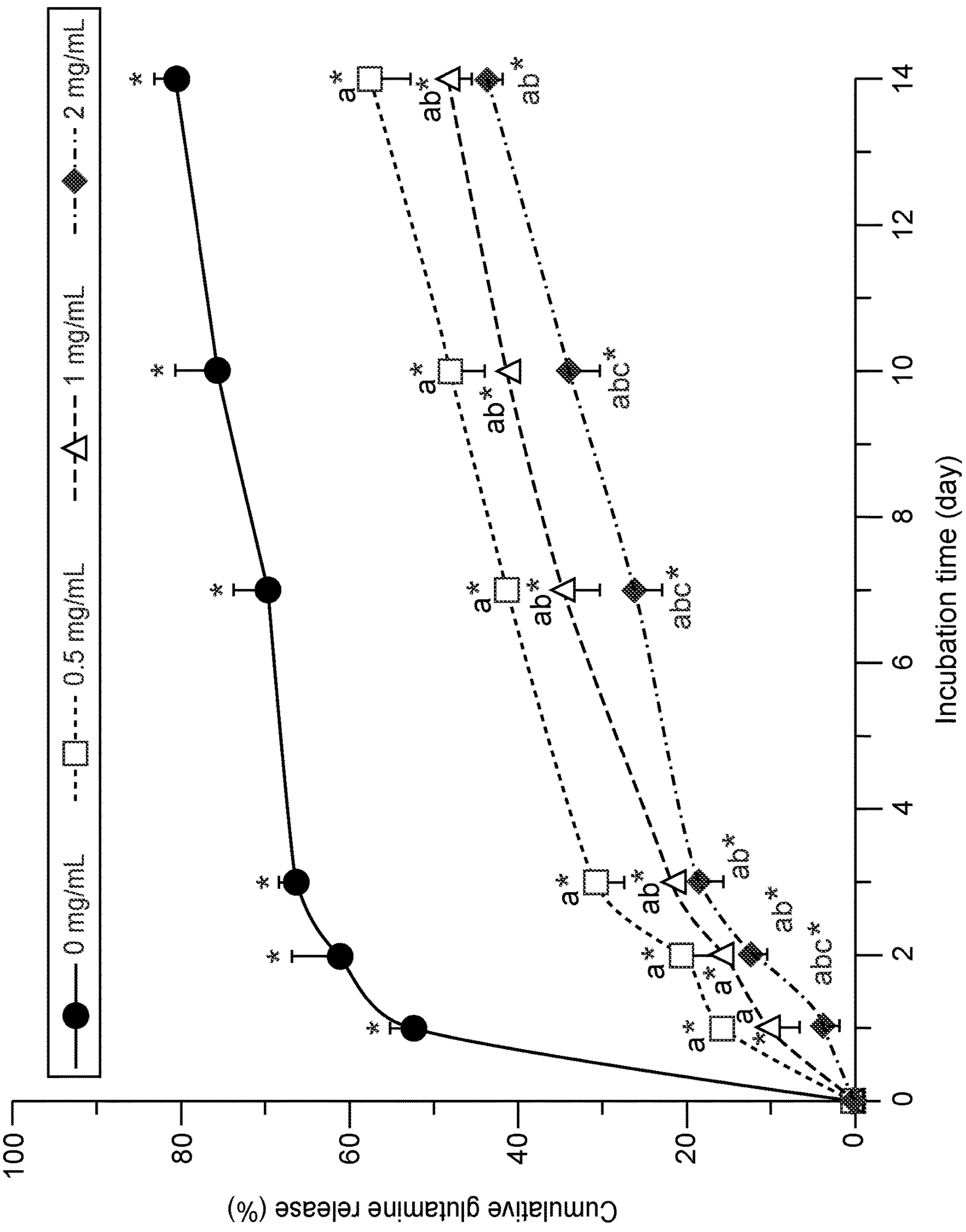
Figure 1I:
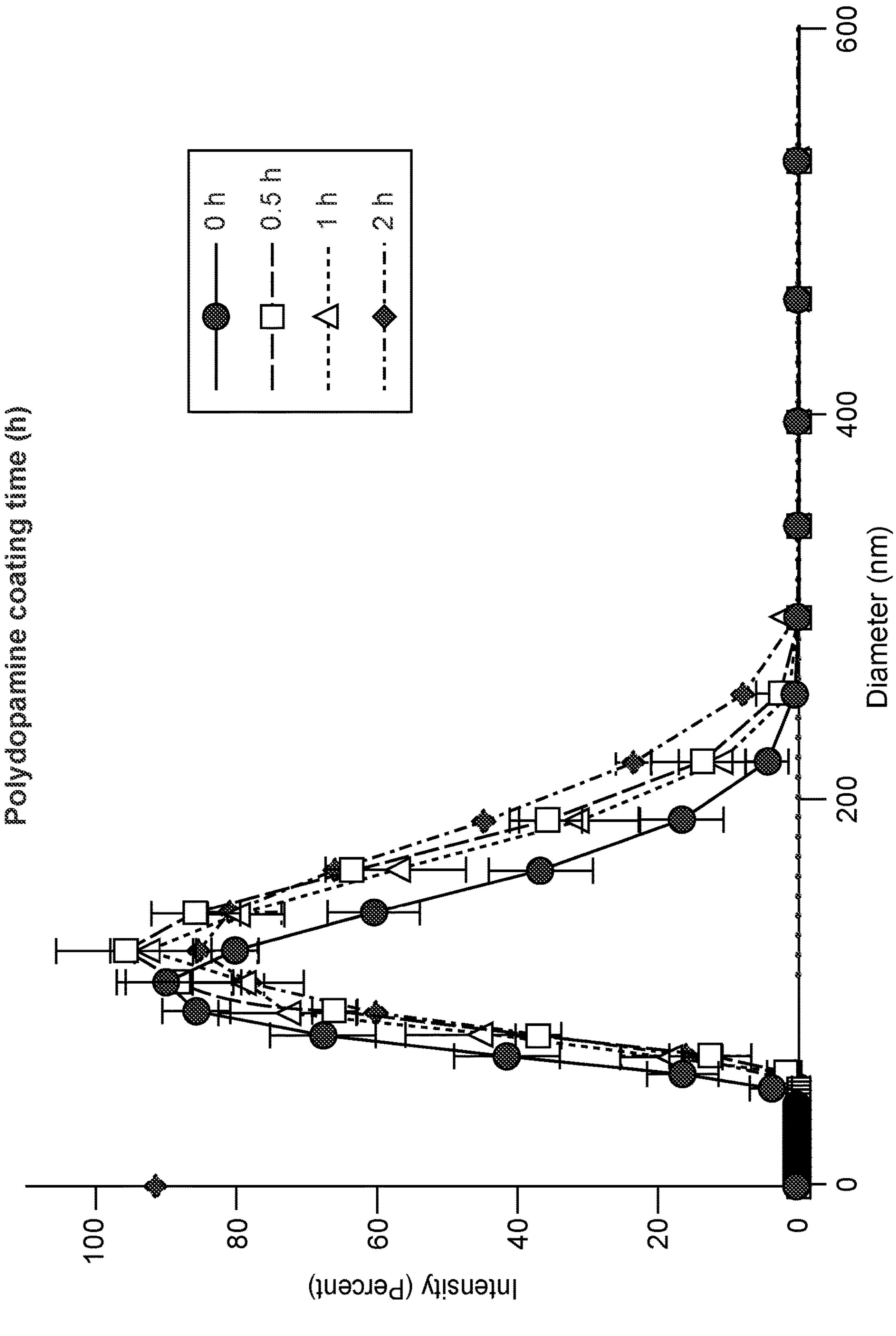
Figure 1J:
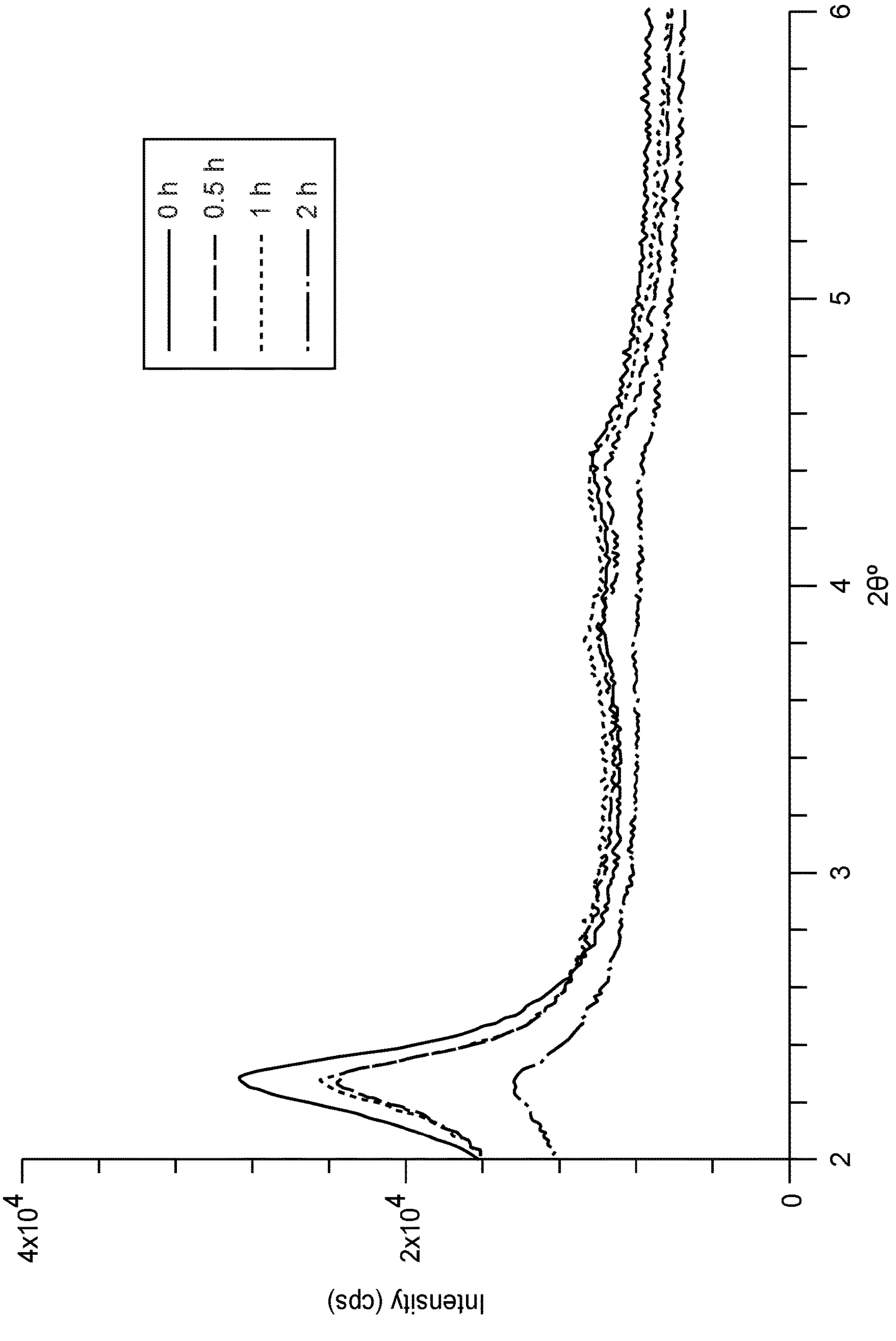
Figure 1K:
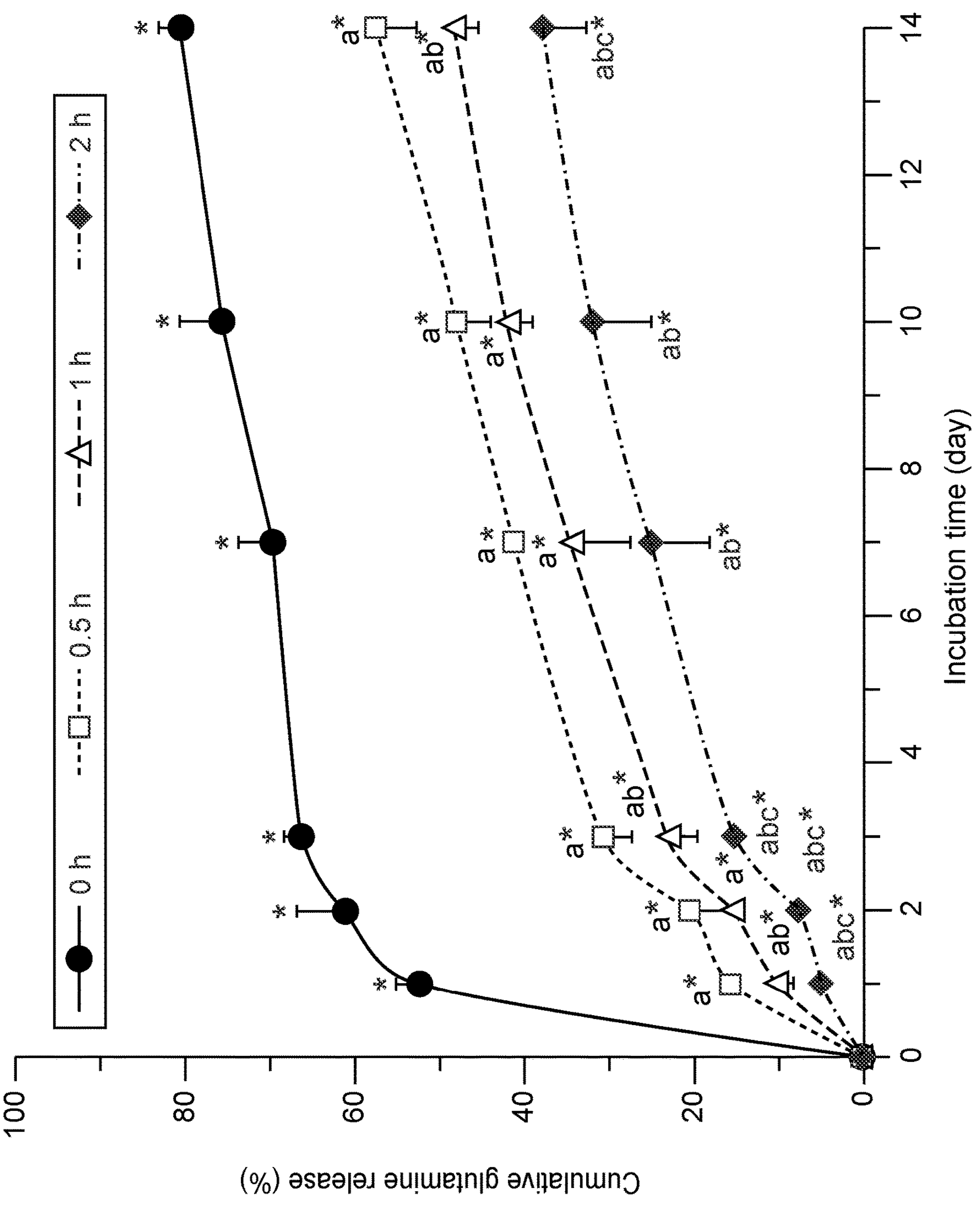
Figure 6A:
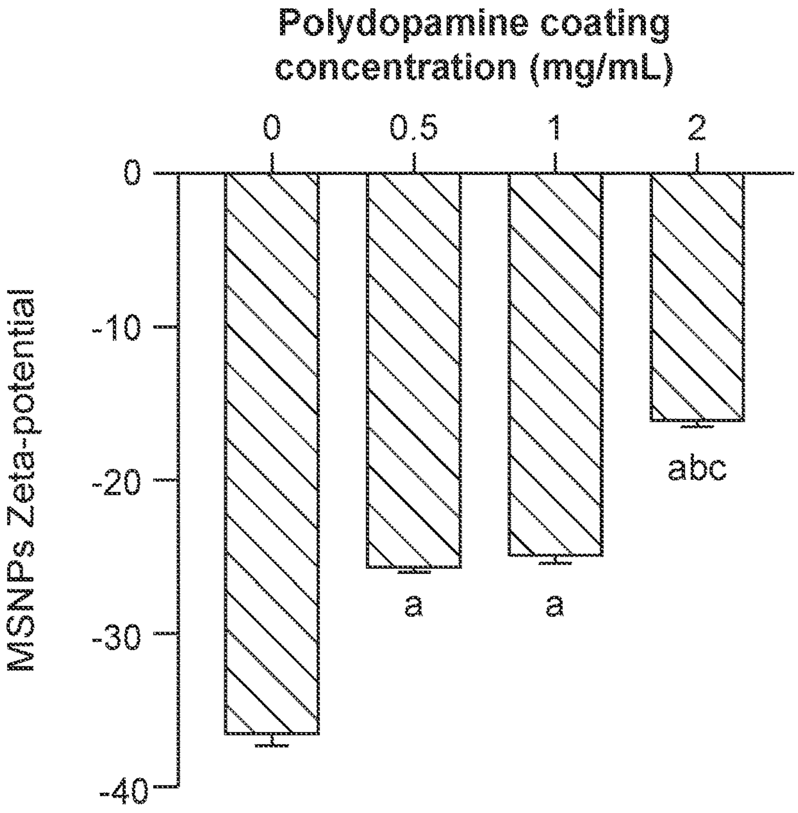
FIGS. 6A-6B. Surface charge of MSNPs.
Figure 6B:
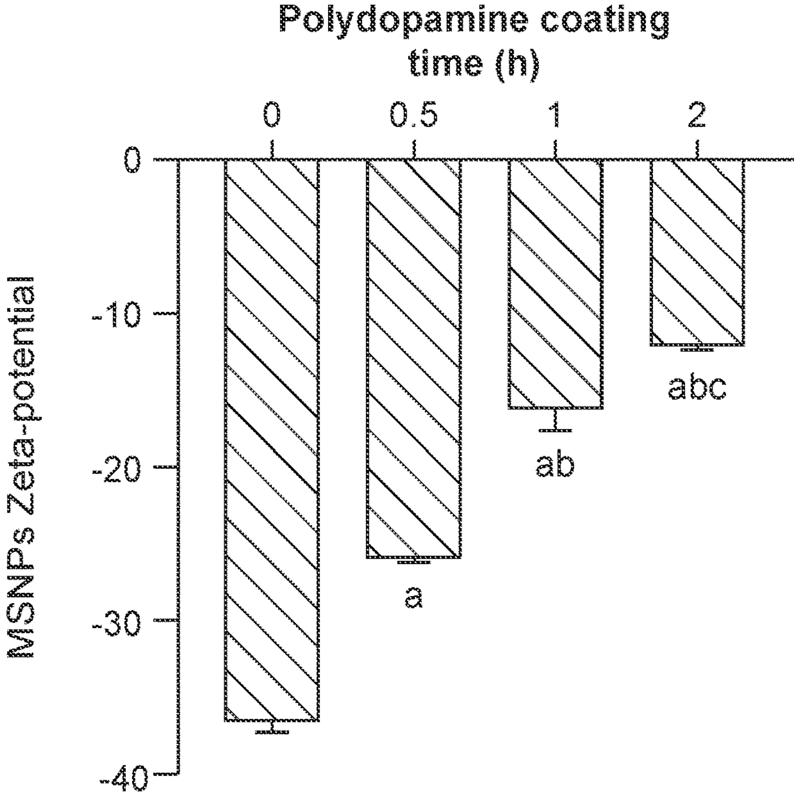
Figure 7:
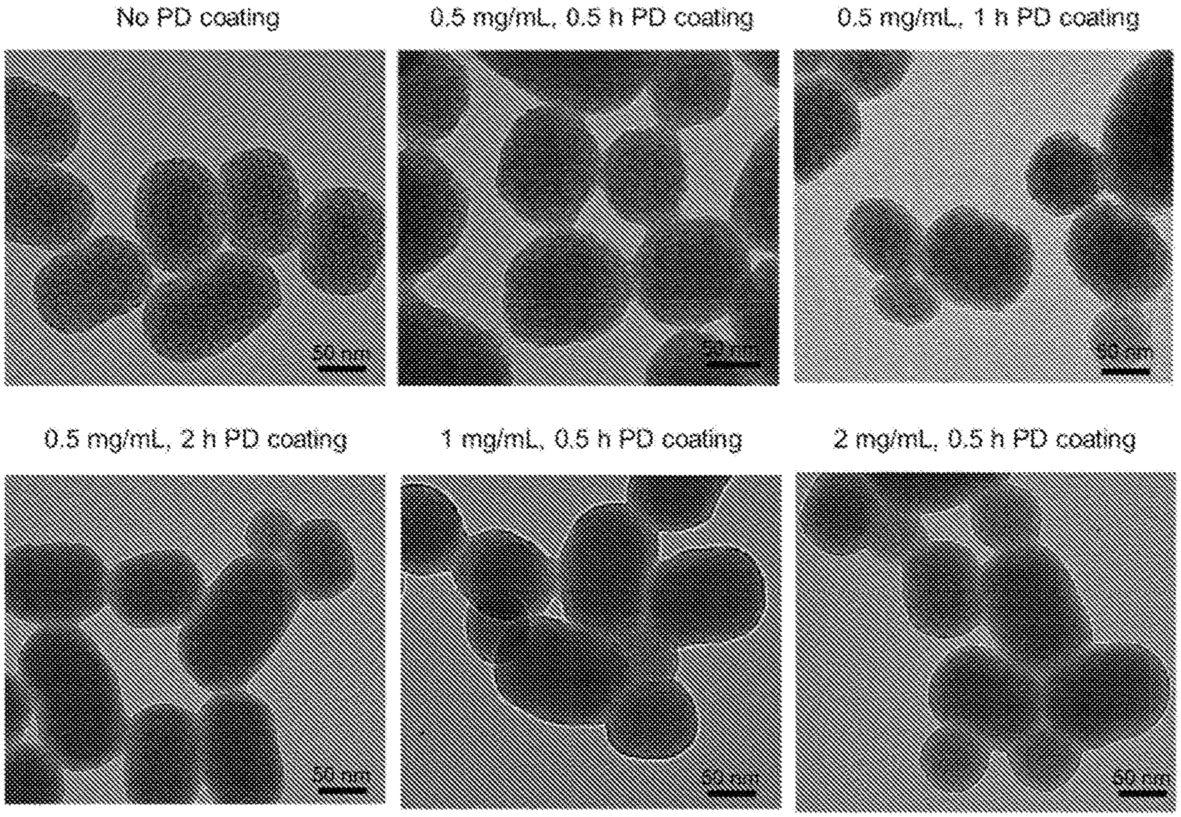
Figure 8:
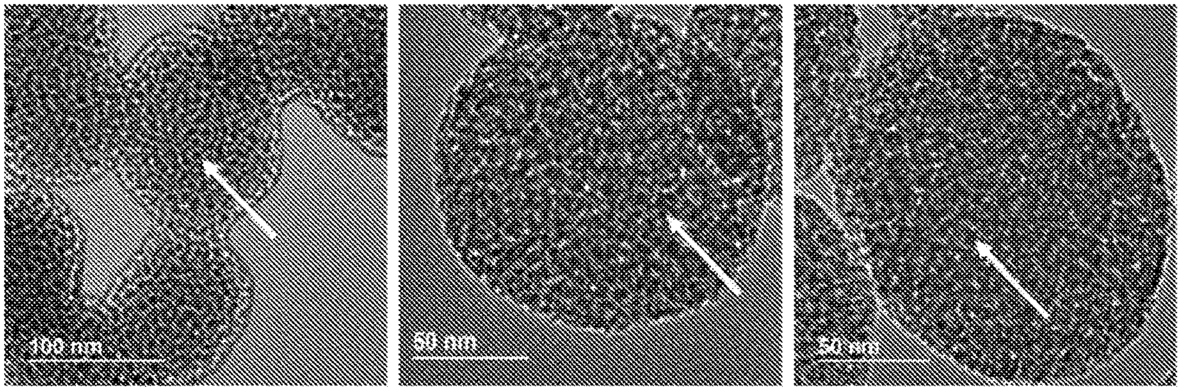
Figure 9A:
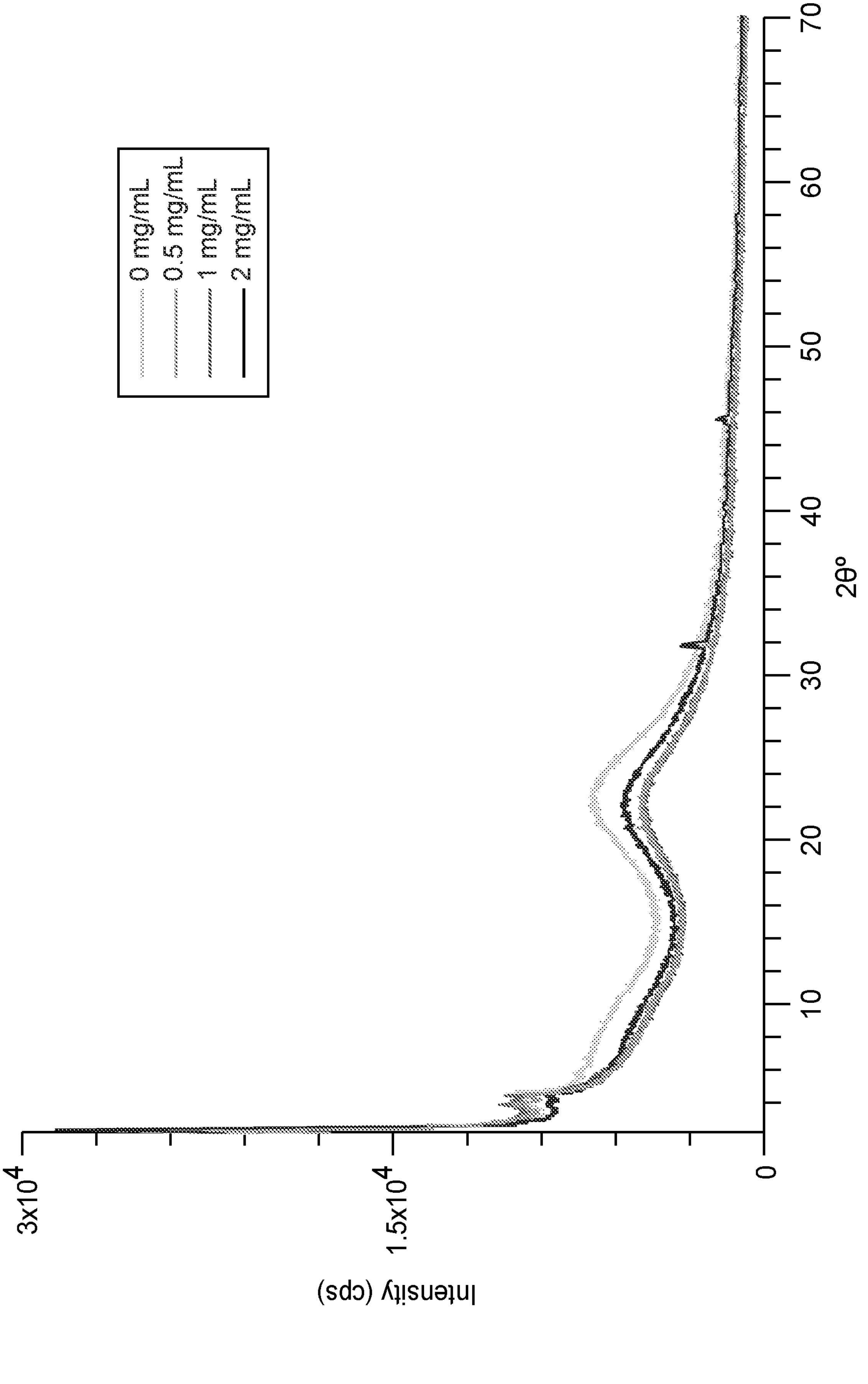
FIGS. 9A-9B. XRD analysis of MSNPs. XRD analysis of uncoated- and polydopamine coated-G-MSNPs obtained using different polydopamine coating concentrations (0, 0.5, 1, 2 mg/mL) over 0.5 h (FIG. 9A) and times (0, 0.5, 1, 2 h) at concentration 0.5 mg/mL (FIG. 9B).
Figure 9B:
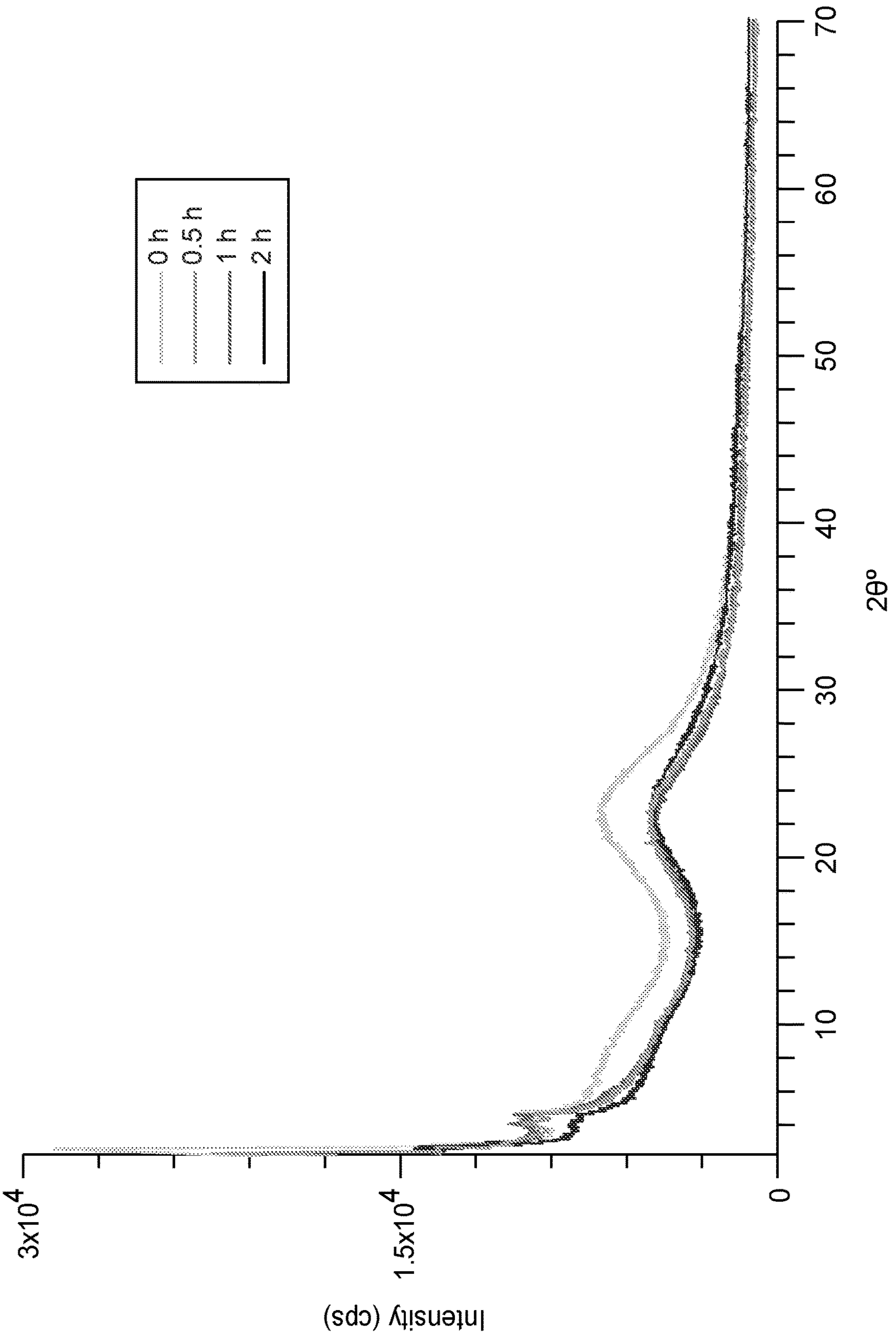
Figures 10A, 10B:
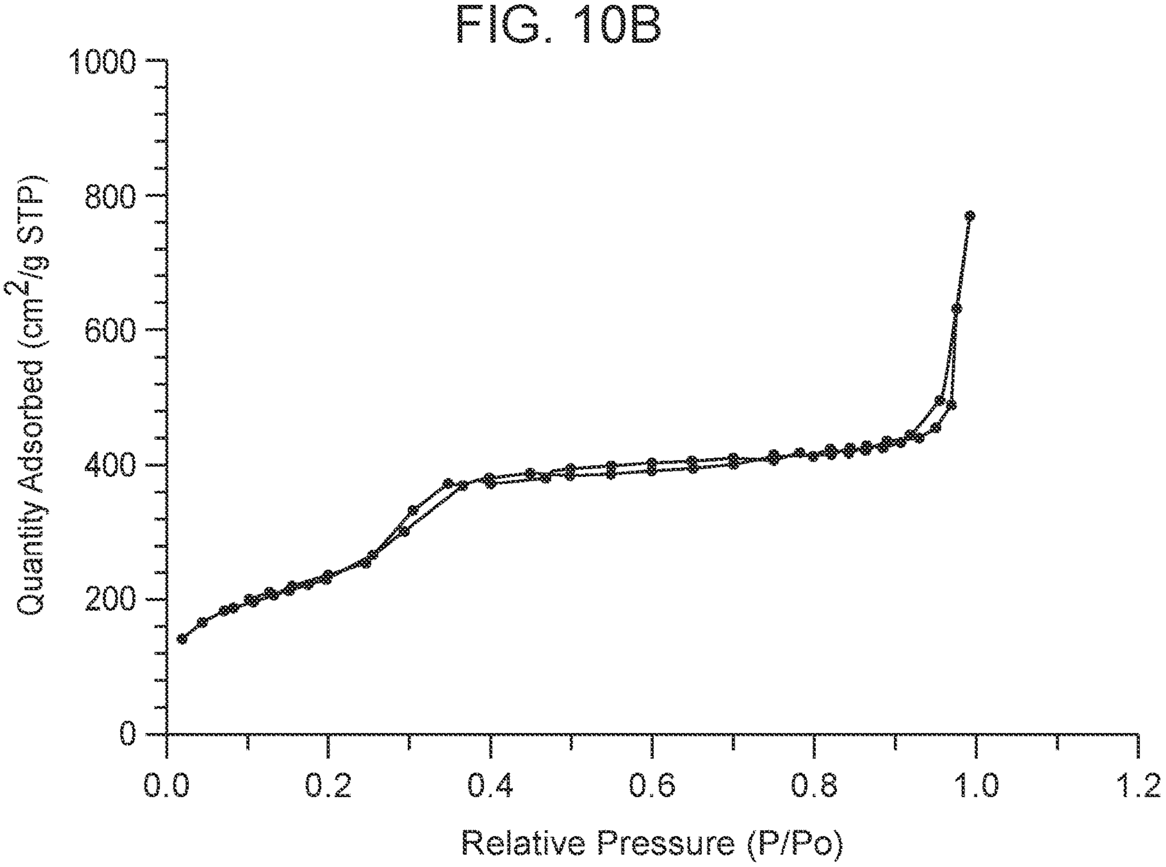
FIGS. 10A-10C. BET analysis of MSNPs.
Figure 10C:
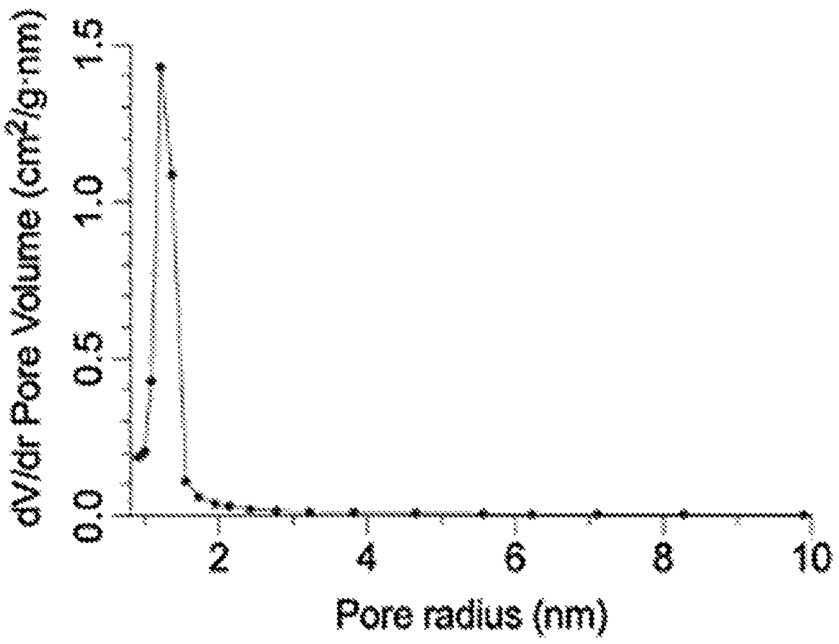
Figures 11A, 11B, 11C:
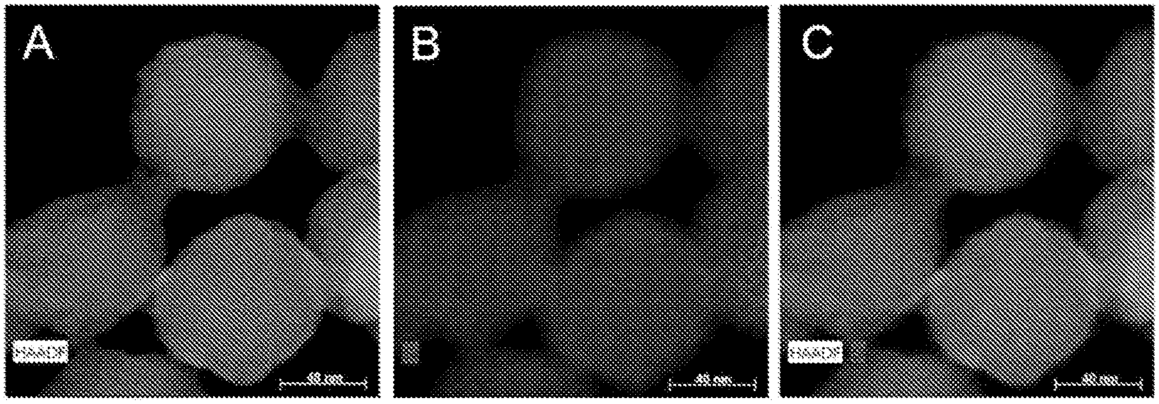
FIGS. 11A-11D. EDS analysis of MSNPs.
Figure 11D:
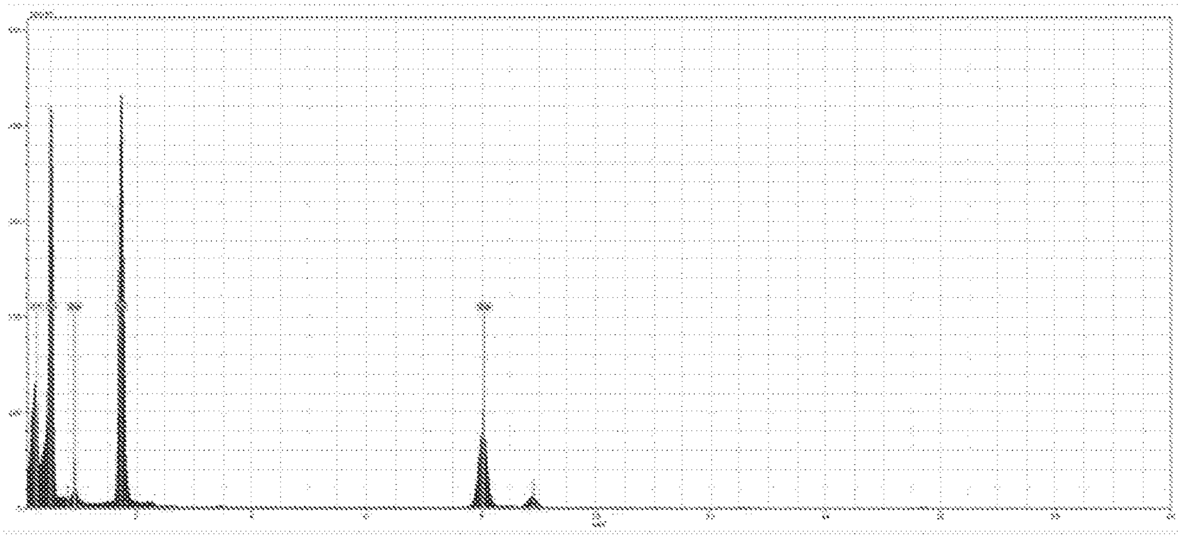
Figure 12A:
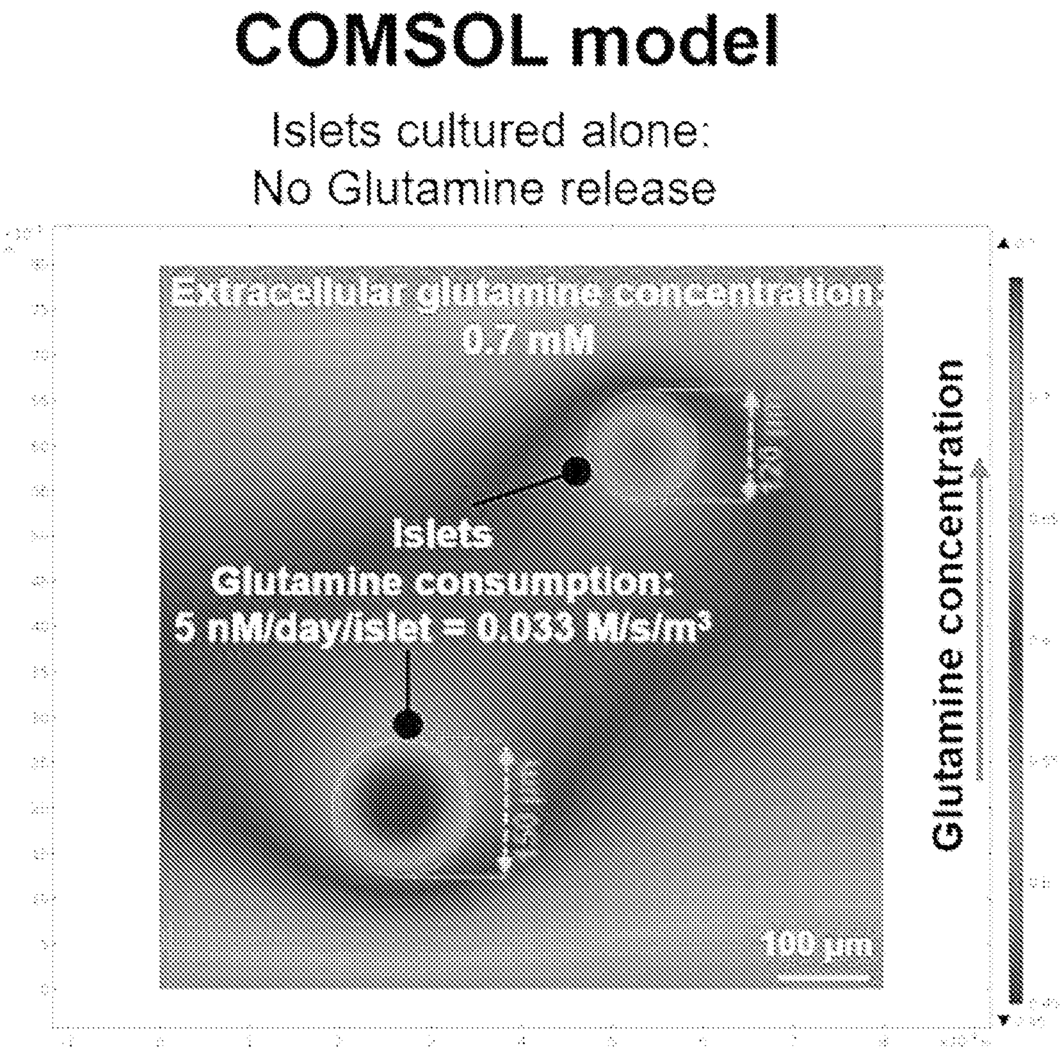
FIGS. 12A-12D. Computational model-calculated glutamine concentrations.
Figure 12B:
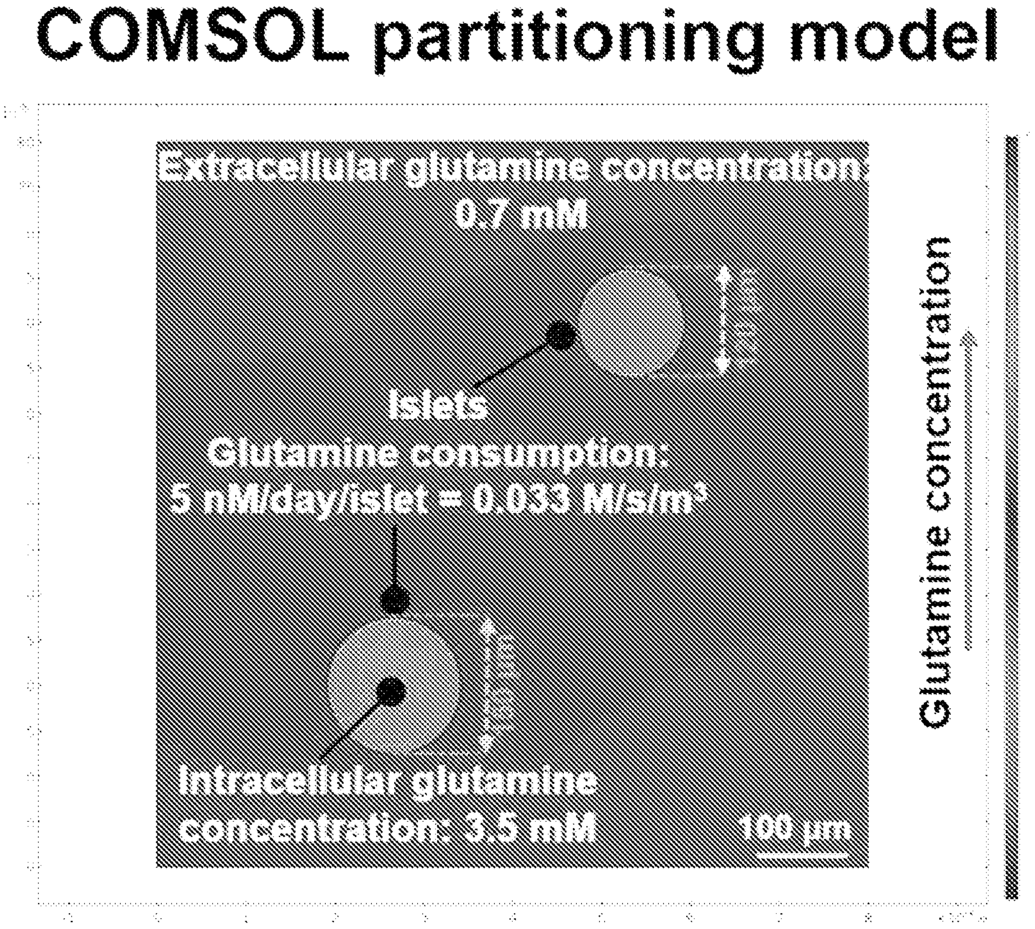
Figure 12C:
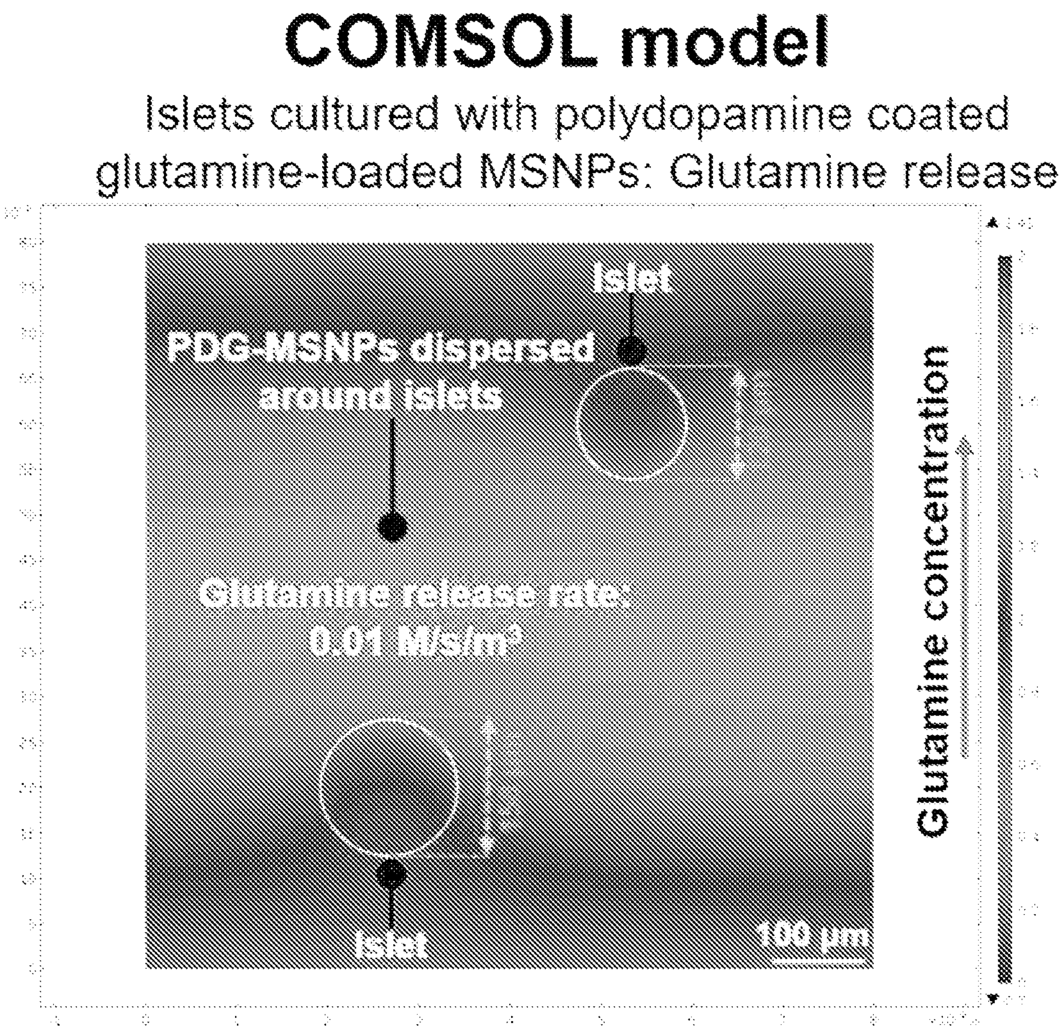
Figure 12D:
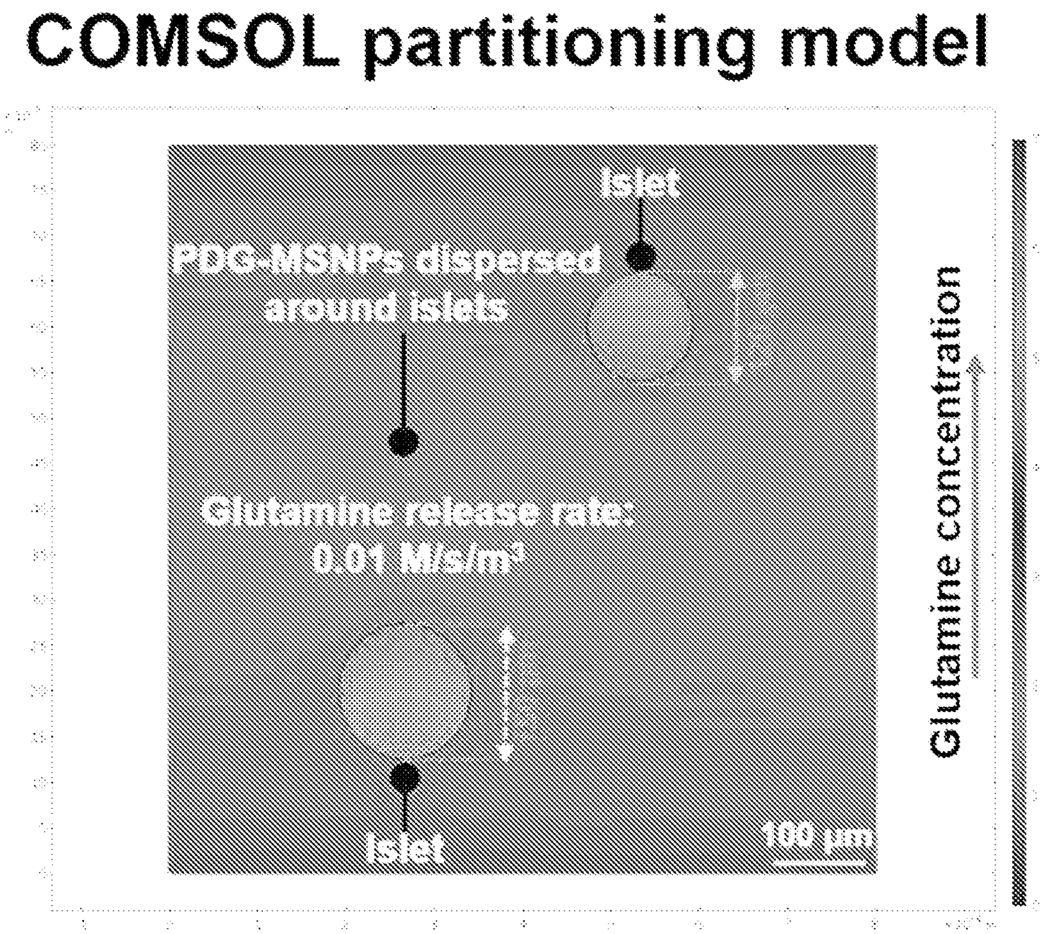
Figure 13A:
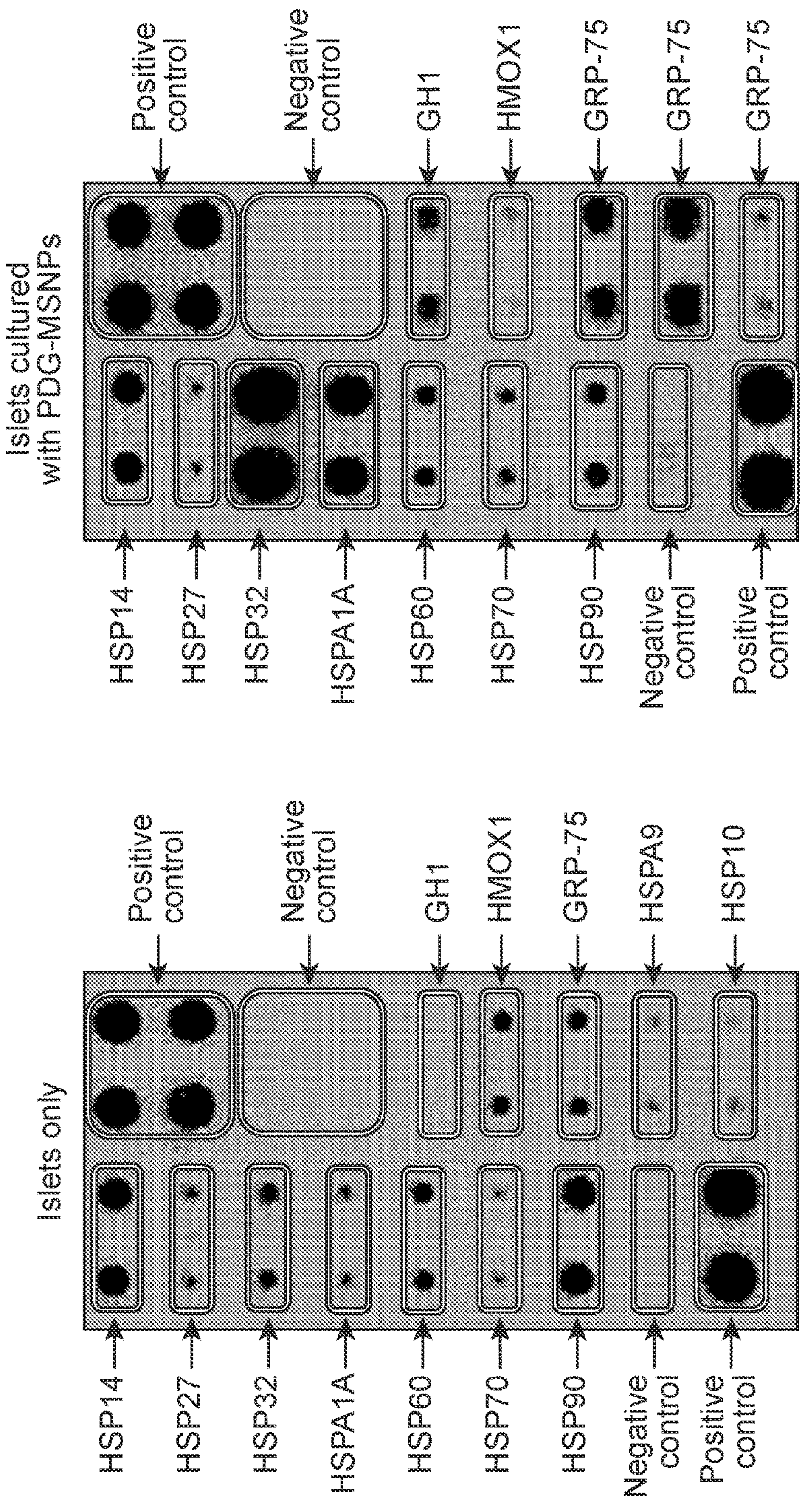
FIGS. 13A-13B. Islet Protein Expression.
Figure 13B:
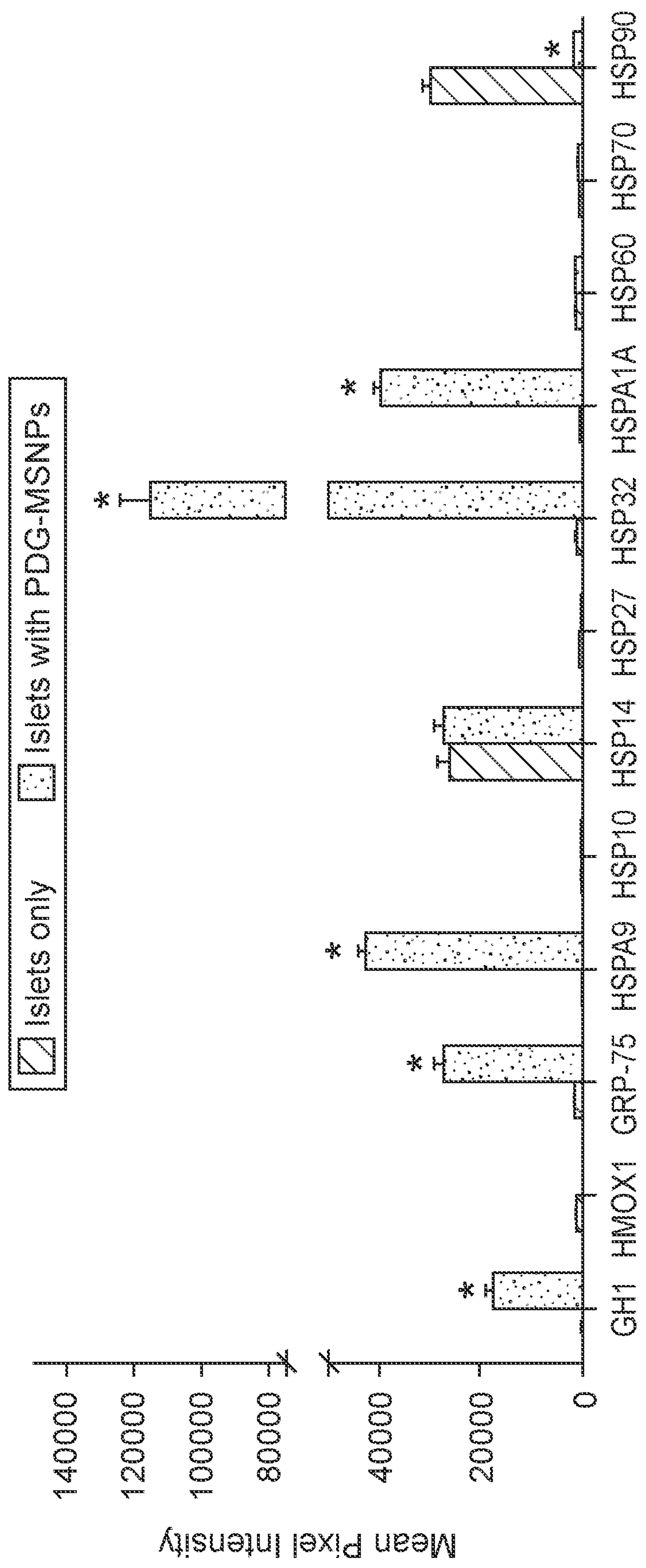

G-MSNPs have been coated with polydopamine using different polydopamine coating concentrations and times. Photographs showed a color change from light to dark brown, which confirmed the polydopamine coating on G-MSNPs, since polydopamine coatings typically exhibit a brownish color. The brown color became increasingly darker as the concentration and time of polydopamine coating increased (FIG. 1C). TEM images showed that uncoated and polydopamine-coated G-MSNPs were oval in shape with an average size of 120 nm (FIGS. 1D and 1E, FIGS. 7 and 8). DLS measurements confirmed the average diameter of uncoated G-MSNPs at 113.9±6.6 nm, a monodisperse population of particles (polydispersity index (PI) of 0.1) and a negative zeta potential (−36.57±1.20). However, PDG-MSNPs obtained with different concentrations (0.5, 1, 2 mg/mL) and times (0.5, 1, 2 h) had a larger size ($p<0.05$) and a more positive surface charge ($p<0.05$) compared to uncoated G-MSNPs (FIGS. 1F, 1I, FIG. 6, Tables 3, 4). The XRD analysis of MSNPs showed diffraction peaks in low 2θ angles due to the MSNPs hexagonal structure. Three peaks at 2θ of 2.2°, 4.8° and 23.2° corresponding to 100, 110, 200 planes, respectively indicated the formation of a well-ordered structure. Following the polydopamine coating, the background XRD peaks increased due to the amorphous polymeric structure of polydopamine (FIGS. 1G, 1L, FIG. 9).[25-27]

In addition, the cumulative release profiles showed that glutamine is released from PDG-MSNPs in a dose- and time-dependent manner. The polydopamine coating of G-MSNPs resulted in a delayed release of glutamine which was dependent on both the polydopamine coating concentration and time (FIGS. 1H, 1M; $p<0.05$). After 1-day incubation, the amount of cumulative glutamine released significantly decreased from 52.3±2.7% for uncoated G-MSNPs to 15.4±0.7, 10.1±1.9, and 4.8±1.2% for PDG-MSNPs with polydopamine coating times of 0.5, 1, and 2 h, respectively ($p<0.05$). Similar behavior was observed using different polydopamine coating concentrations (0.5, 1, 2 mg/mL). This effect was maintained over a period of 14 days (FIGS. 1H, 1M; $P<0.05$).

Figure 2A:
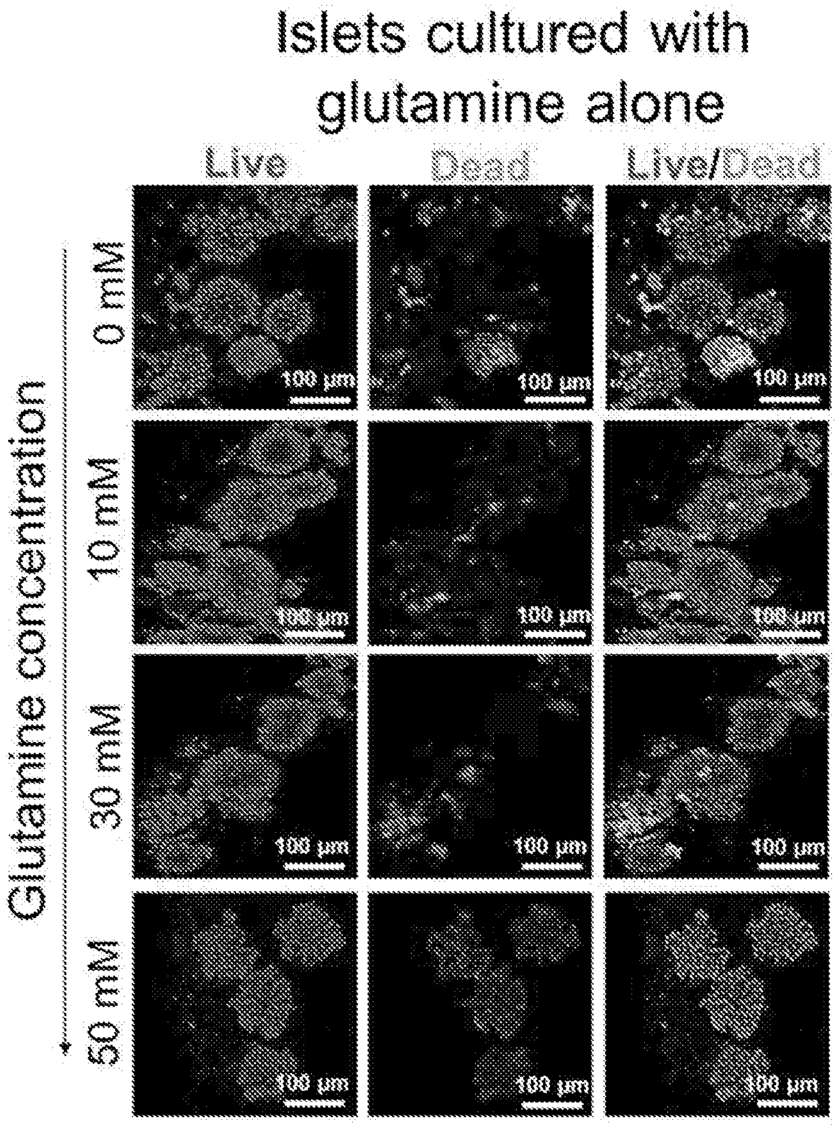
Figure 2B:
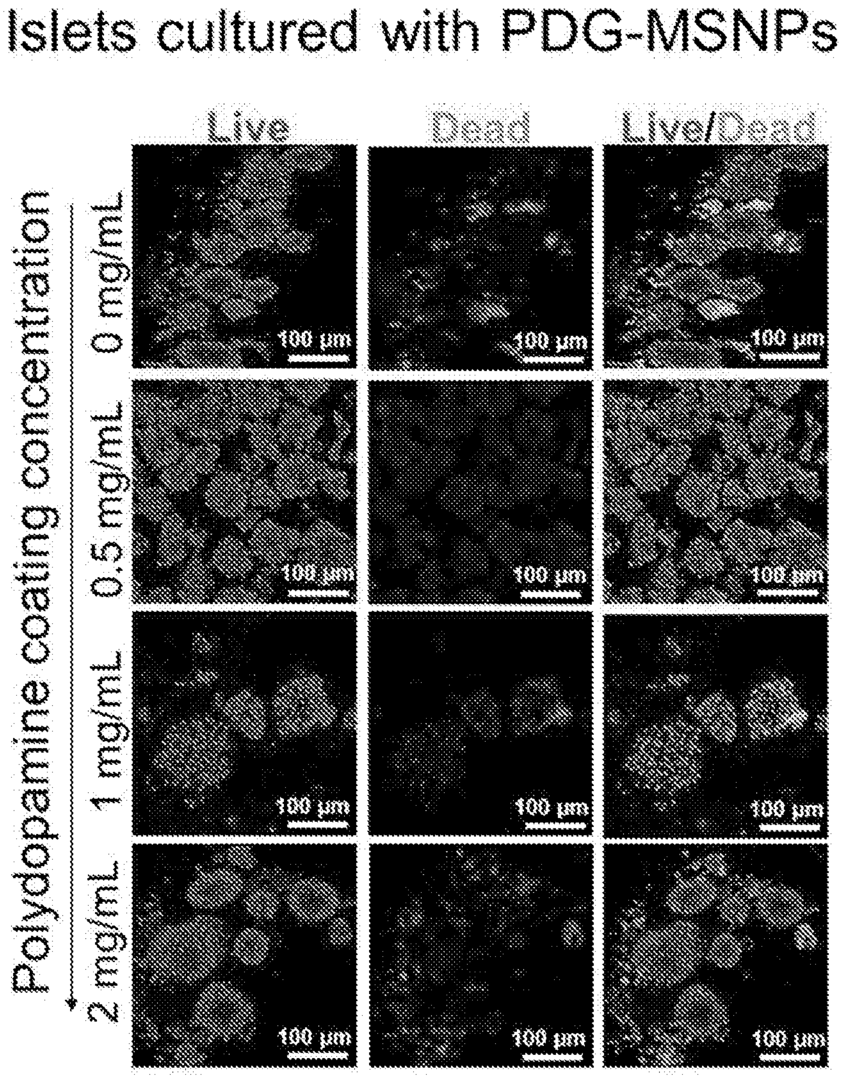
Figure 2C:
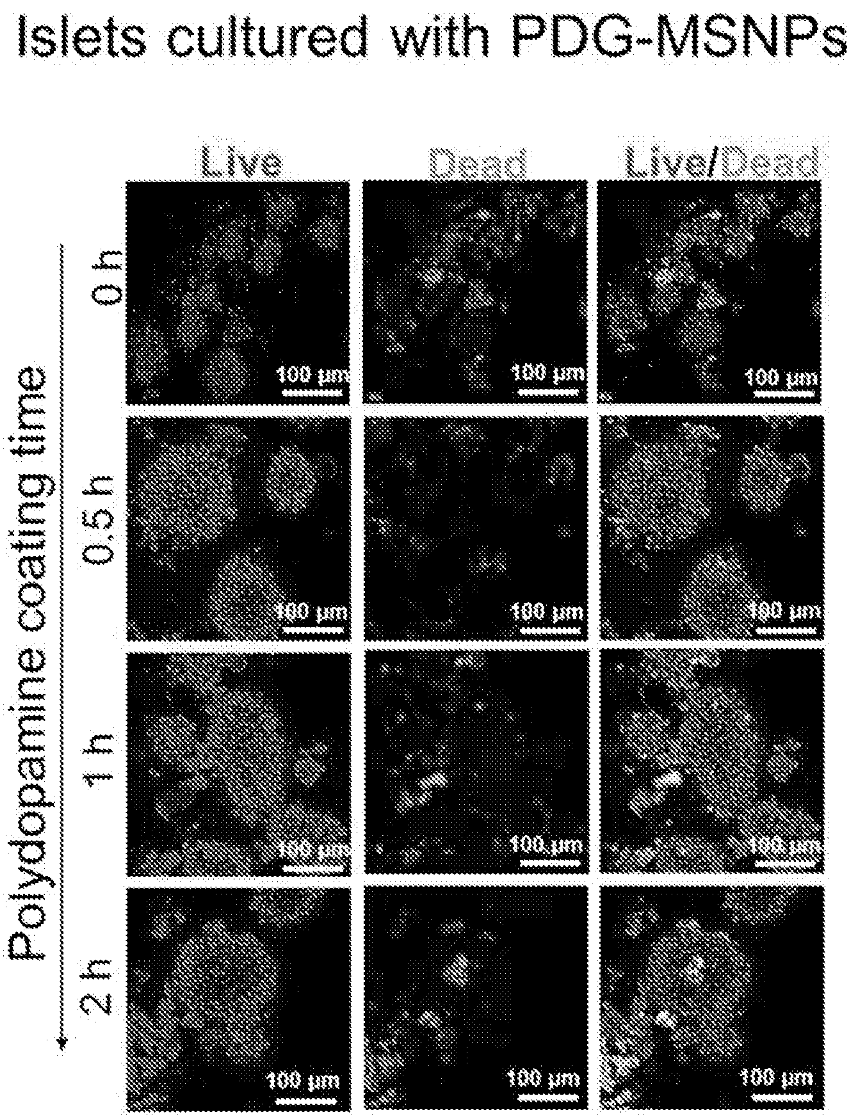
Figure 2J:
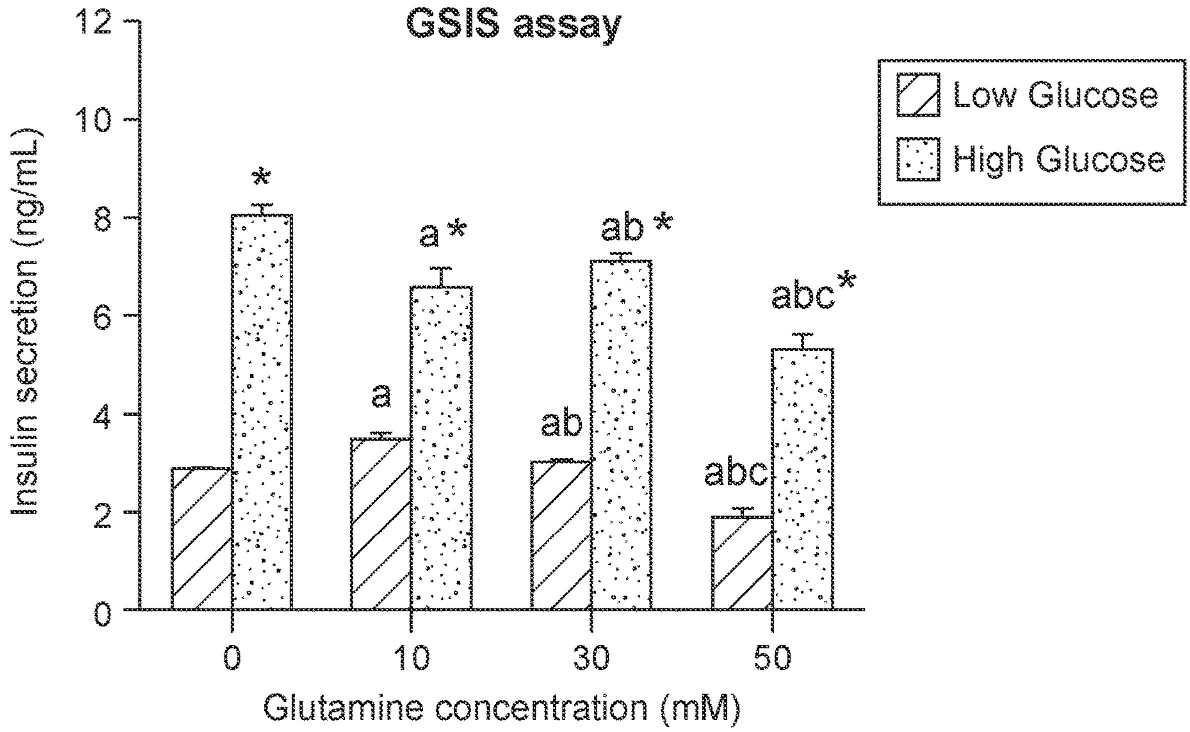
Figure 2K:
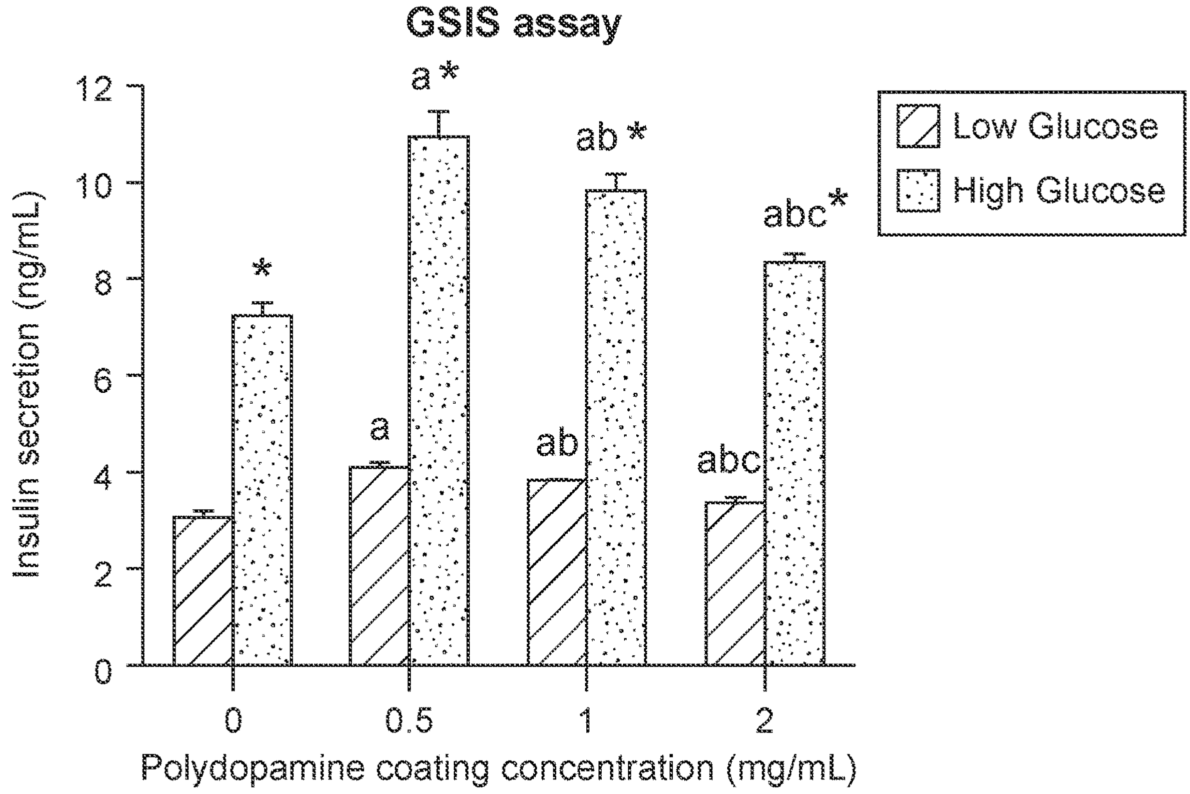
Figure 2L:
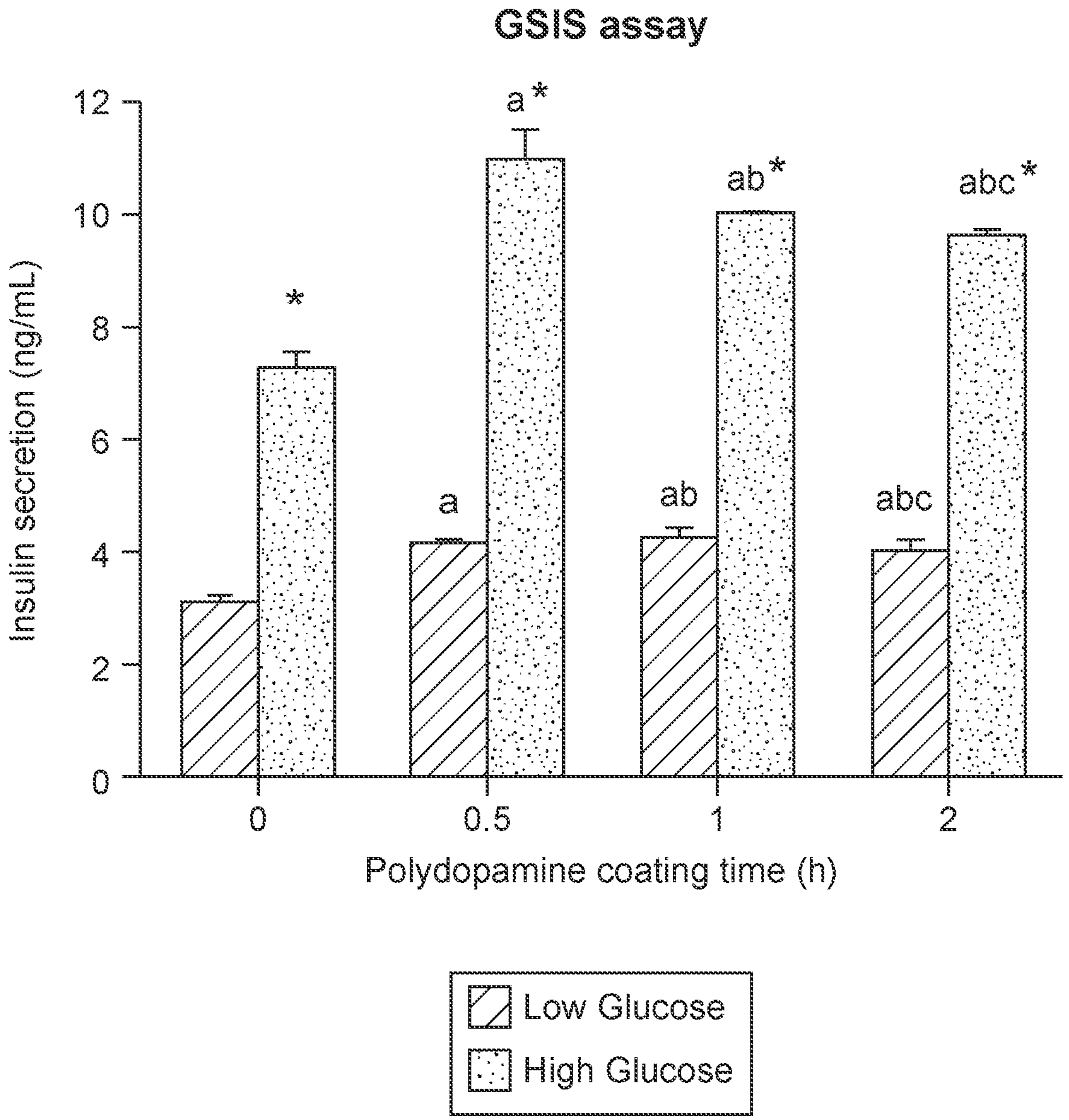

Confocal images showed islets are more viable (green) when seeded with glutamine (10, 30 mM) or PDG-MSNPs at different polydopamine coating concentrations (0.5, 1, 2 mg/mL) and times (0.5, 1. 2 h) compared to islets only. Specifically, Live/Dead analysis showed that islets cultured with glutamine (10, 30 mM) demonstrated a significantly greater viability at day 7 compared to control islets (i.e. islets cultured alone) ($p<0.05$). Among different concentrations of glutamine tested (i.e. 10-50 mM), 10 mM resulted in the highest islet viability compared to control islets (77.1±2.6 vs. 65.3±2.5%, $p<0.05$) (FIGS. 2A, 2D). Furthermore, when PDG-MSNPs were added to islets for 7 days, the viability increased significantly compared to control islets ($p<0.05$). Among the different tested polydopamine coating concentrations (0.5-2 mg/mL) and times (0.5-2 h), 0.5 mg/mL and 0.5 h resulted in the highest islet viability compared to islets only (FIGS. 2E-2F; 90.7±3.2 vs. 65.3±2.5%, $p<0.05$). Similar results were also observed using an MTT viability assay (FIGS. 2G-2I). The insulin secretory capacity of islets in response to the glucose challenges are reported in FIGS. 2L-2N. GSIS data showed that when islets were cultured with 10 mM of glutamine alone, insulin secretion following stimulation with high glucose medium was significantly higher compared to islets cultured without glutamine (FIG. 2L; 8.1±0.3 vs. 6.6±0.6 ng/mL, $p<0.05$). Likewise, islets cultured with PDG-MSNPs, obtained using different polydopamine coating concentrations (0.5-2 mg/mL) and times (0.5-2 h), showed an elevated insulin secretory response compared to islets cultured without PDG-MSNPs ($p<0.05$). Among the different polydopamine coating concentrations and times tested, when polydopamine was added using a concentration of 0.5 mg/mL over 0.5 h, the insulin secretion was significantly higher than control islets (FIGS. 2M-2N; 10.9±0.9 vs. 7.3±0.4 ng/mL, $p<0.05$).

Figure 3A:
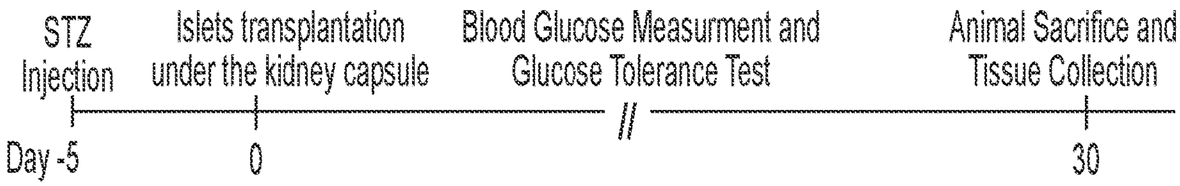
FIGS. 3A-3H. In vivo Interactions of PDG-MSNPs with pancreatic islets.
Figure 3B:
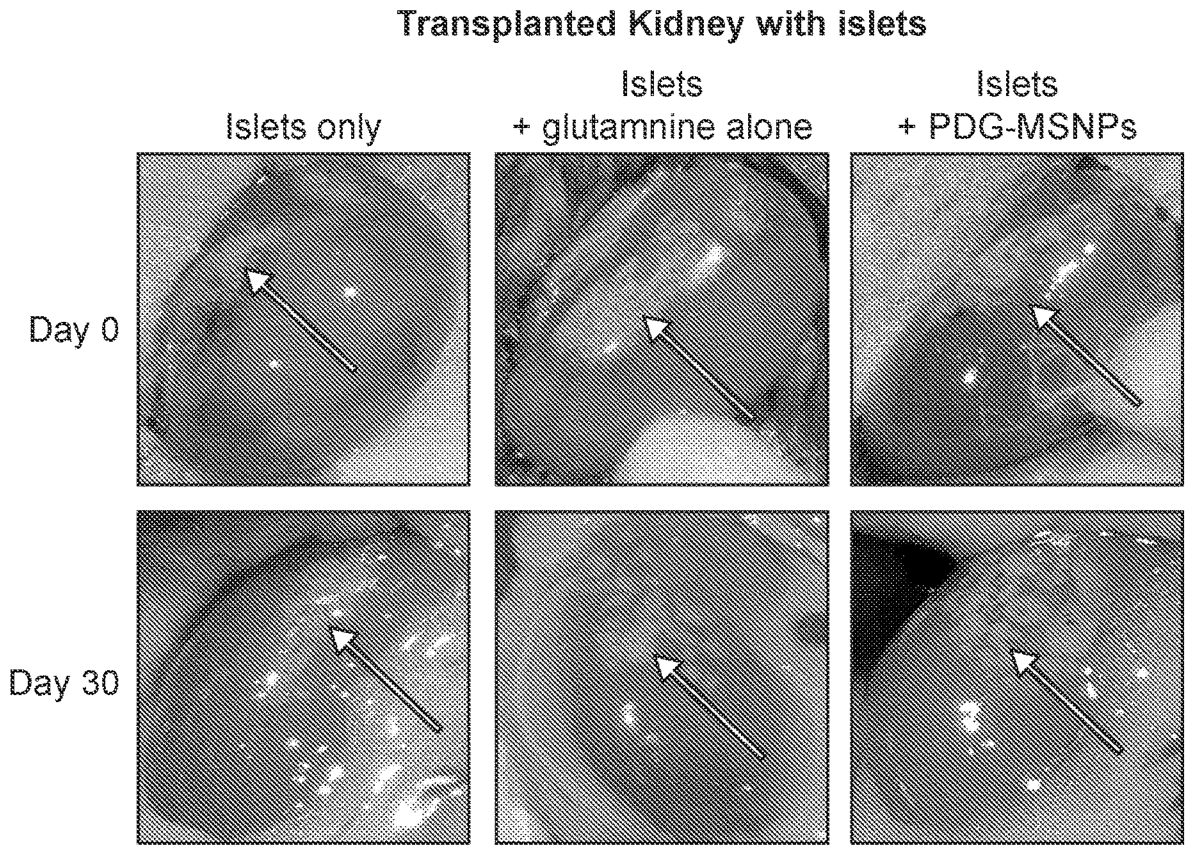
Figure 3C:
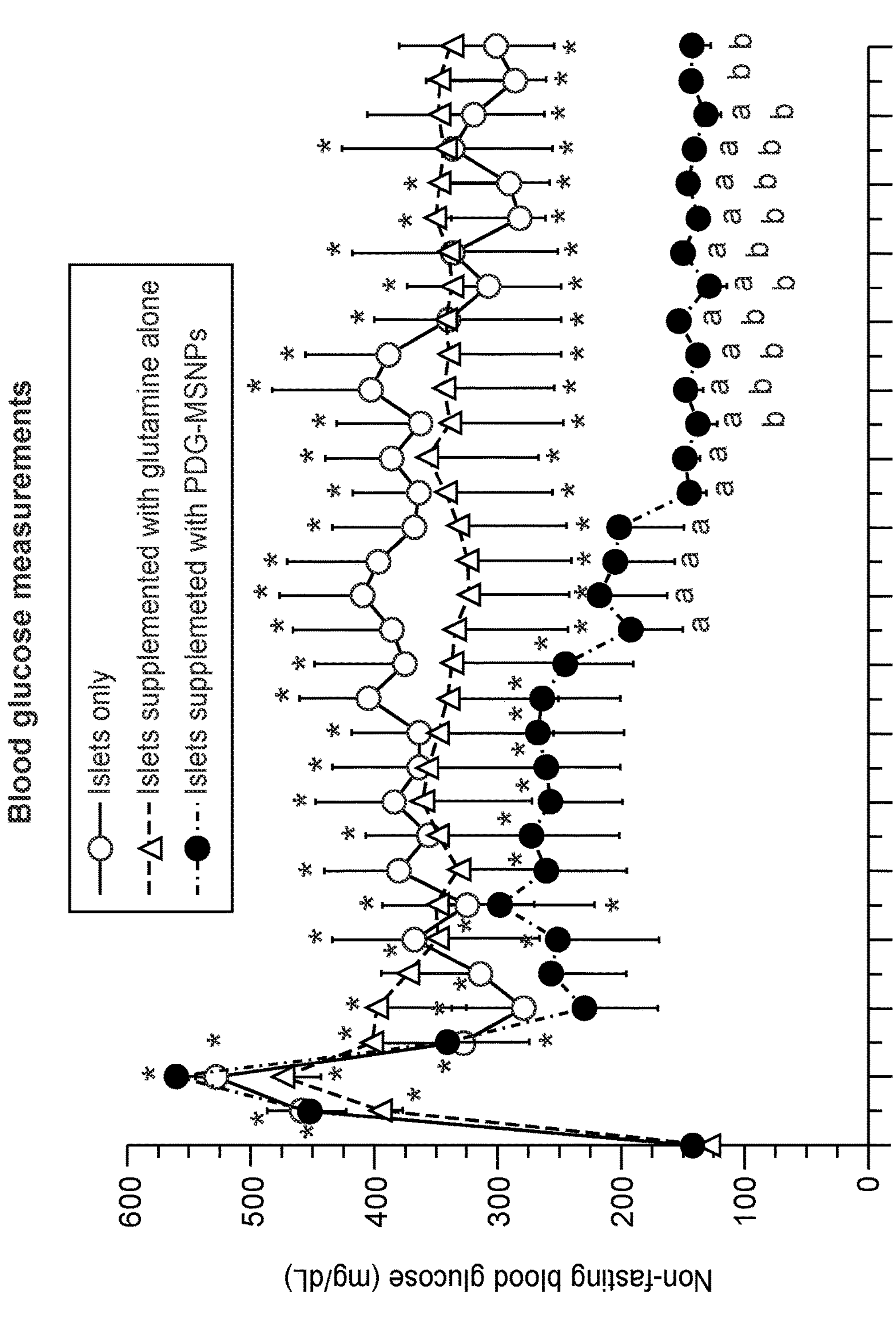
Figure 3D:
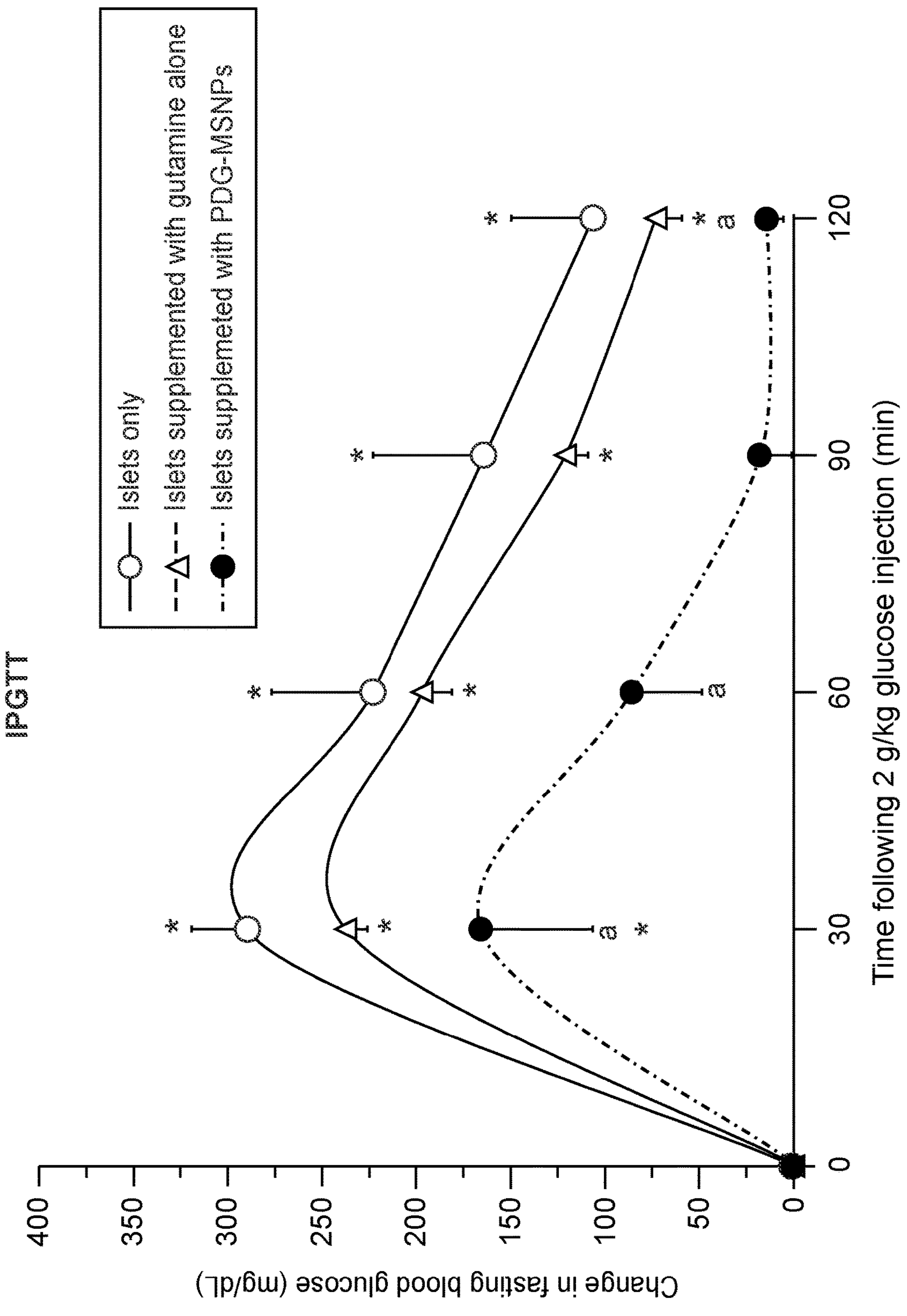
Figure 3E:
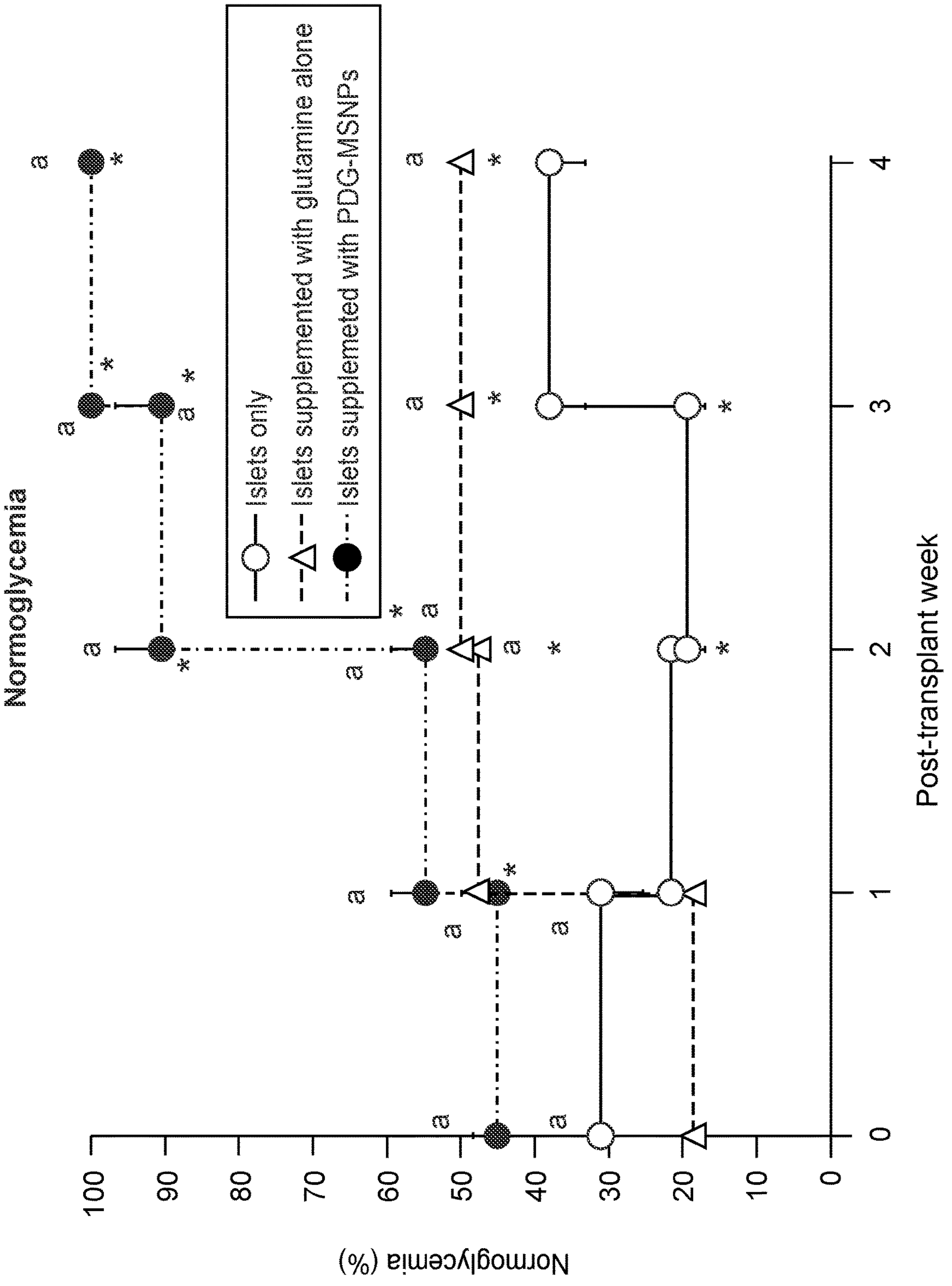
Figure 3F:
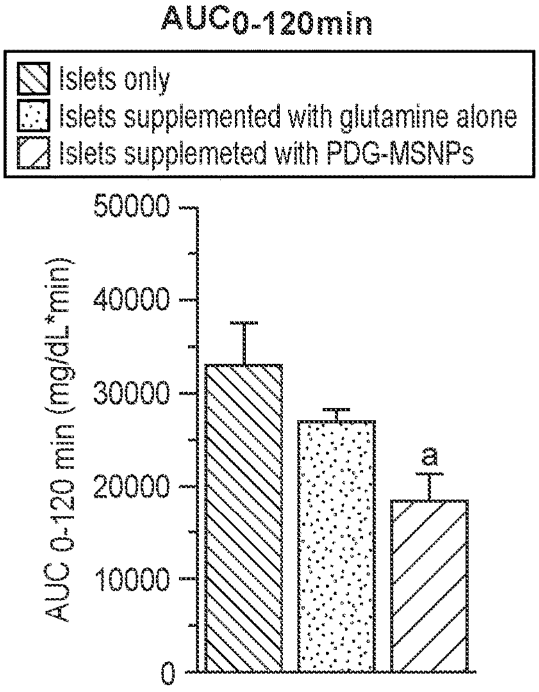
Figure 3G:
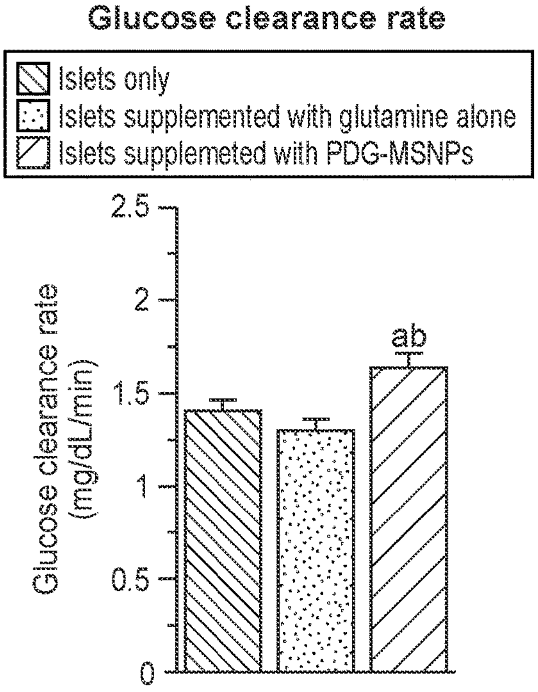
Figure 3H:
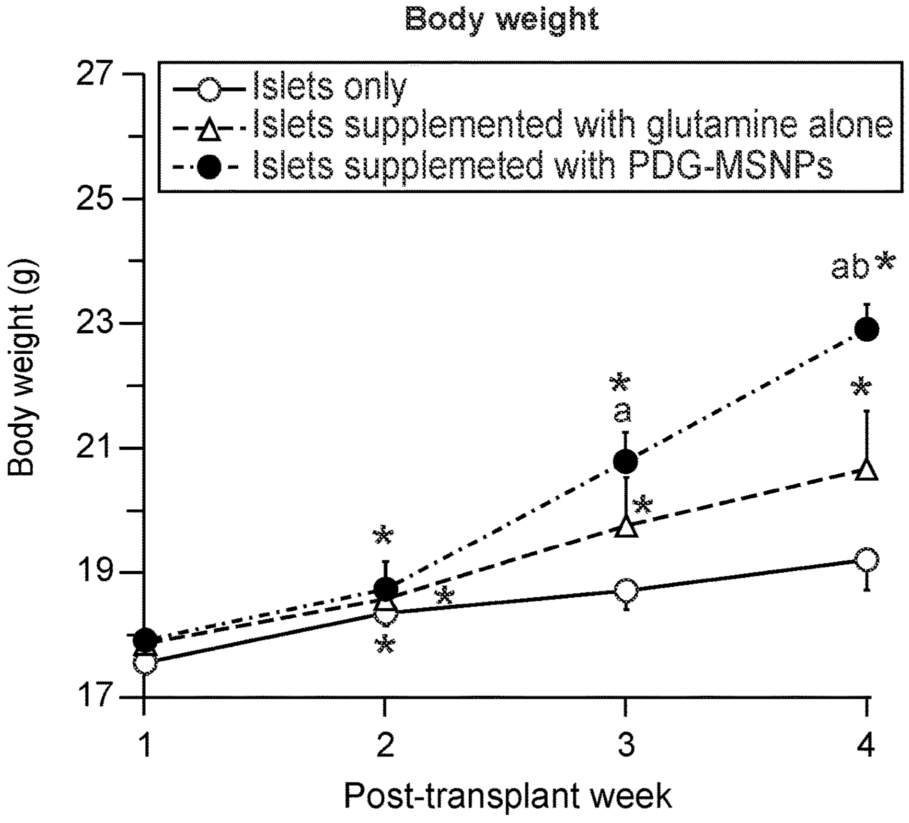

The experimental details of our in vivo transplantation experiments are outlined in FIGS. 3A-3B. Following islet transplantation, all experimental groups showed a significant decrease in their BGLs within the first 48 h. After 48 h, the BGLs began to rise in animals transplanted with islets only or islets supplemented with glutamine alone, and this persisted for the duration of the experimental protocol (day 30: 300±79 or 337±84 mg/dL; respectively). In contrast, animals transplanted with islets supplemented with PDG-MSNPs sustained their reduction in non-fasting BGLs such that from day 17 until the end of the experimental protocol, all animals were normoglycemic and had thus re-established glycemic control (day 30: 141±15 mg/dL; FIG. 3C). Indeed, 45±3% animals transplanted with islets supplemented with PDG-MSNPs became normoglycemic in the first week post-transplantation, and this increased to 100±0% in the $4^{th}$ week post-transplantation (FIG. 3E). Moreover, mice transplanted with islets and PDG-MSNPs progressively increased their body weight from 17.9±0.1 g (week 1) to 22.9±0.5 g (week 4) ($p<0.05$), which was significantly higher compared animals transplanted with islets only and islets supplemented with glutamine alone (19.2±0.3 g and 20.7±0.9 g at week 4 ($p<0.05$), respectively) (FIG. 3H). As shown in FIG. 3D, BGLs significantly increased in all experimental groups after intraperitoneal glucose administration, with a peak-value seen at 30 min ($p<0.05$). However, in animals which received PDG-MSNPs, the peak incremental value following glucose injection was significantly lower (165±58 vs. 290±30 or 238±12 mg/dL for mice transplanted with islets alone or islets supplemented with glutamine alone, respectively; $p<0.05$, FIG. 3D) and these animals also restored their glucose values back to baseline levels by 120 min, unlike those animals which received transplantation of islets only or islets supplemented with glutamine alone. Accordingly, the $AUC_{0\text{-}20\ min}$ (18326±2932 vs. 32945±4481 or 26935±1347 mg/dL*min; $p<0.05$, FIG. 3F) was significantly lower and the glucose clearance rate (1.6±0.1 vs. 1.4±0.1 or 1.3±0.1 mg/dL/min; $p<0.05$, FIG. 3G) was significantly faster in animals which had received islets supplemented with PDG-MSNPs compared to those animals which received an islet transplantation alone or islets supplemented with glutamine alone.

Figure 4A:
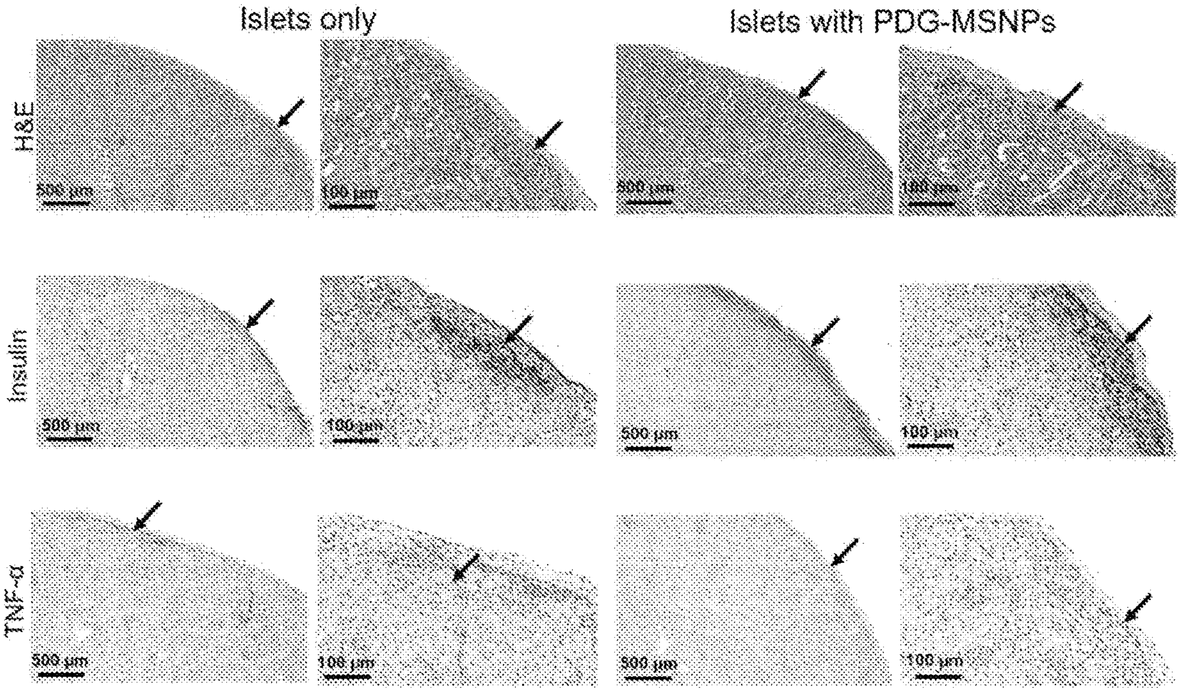
FIGS. 4A-4G. Histological and molecular analyses of kidney tissue and serum after mice sacrifice.
Figure 4B:
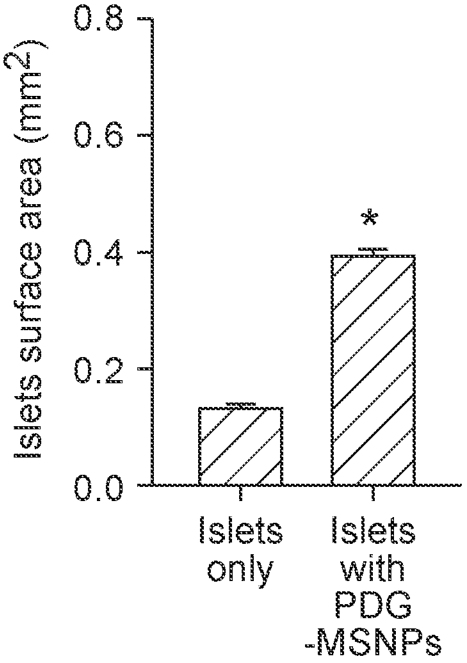
Figure 4C:
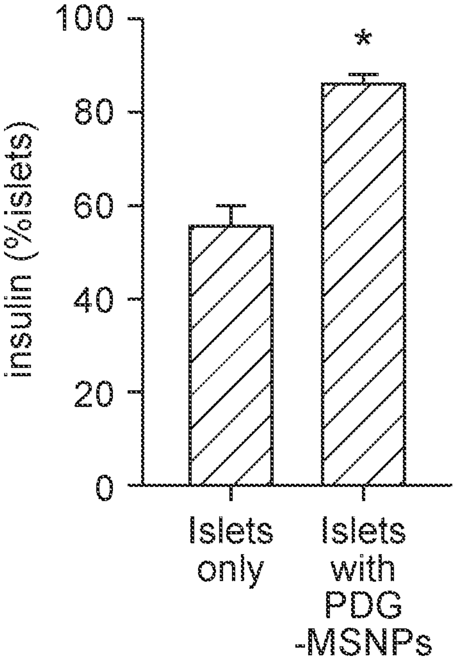
Figure 4D:
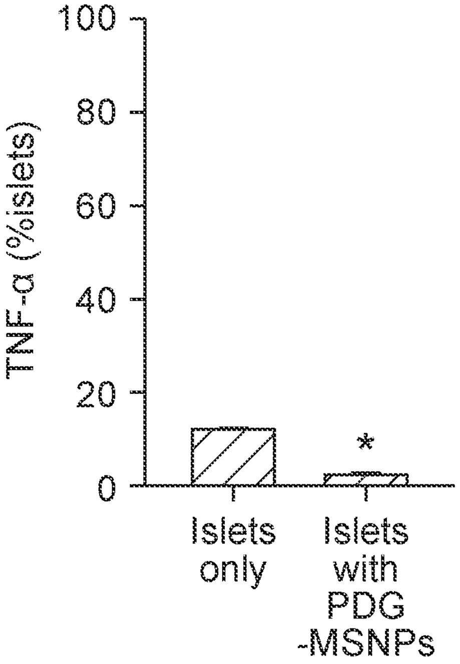
Figure 4E:
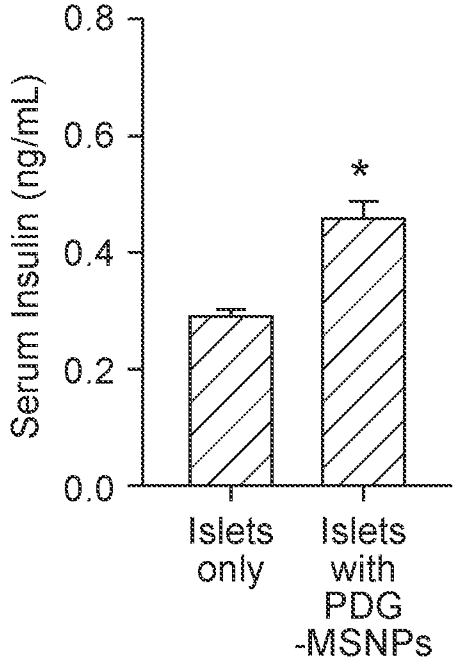
Figure 4G:
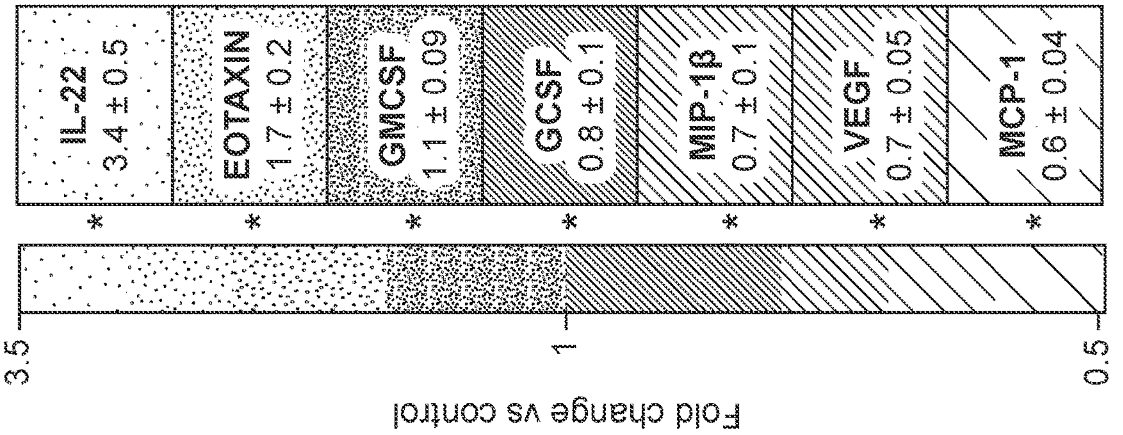
Figure 4F:
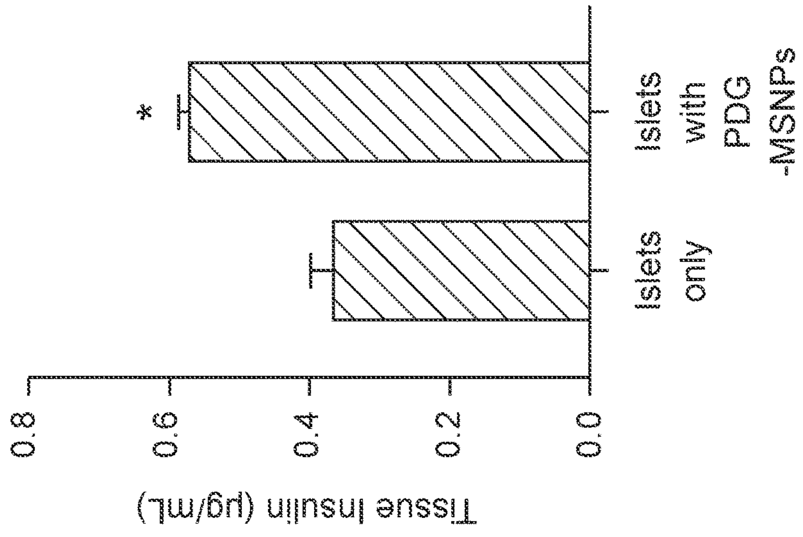
Figure 5A:
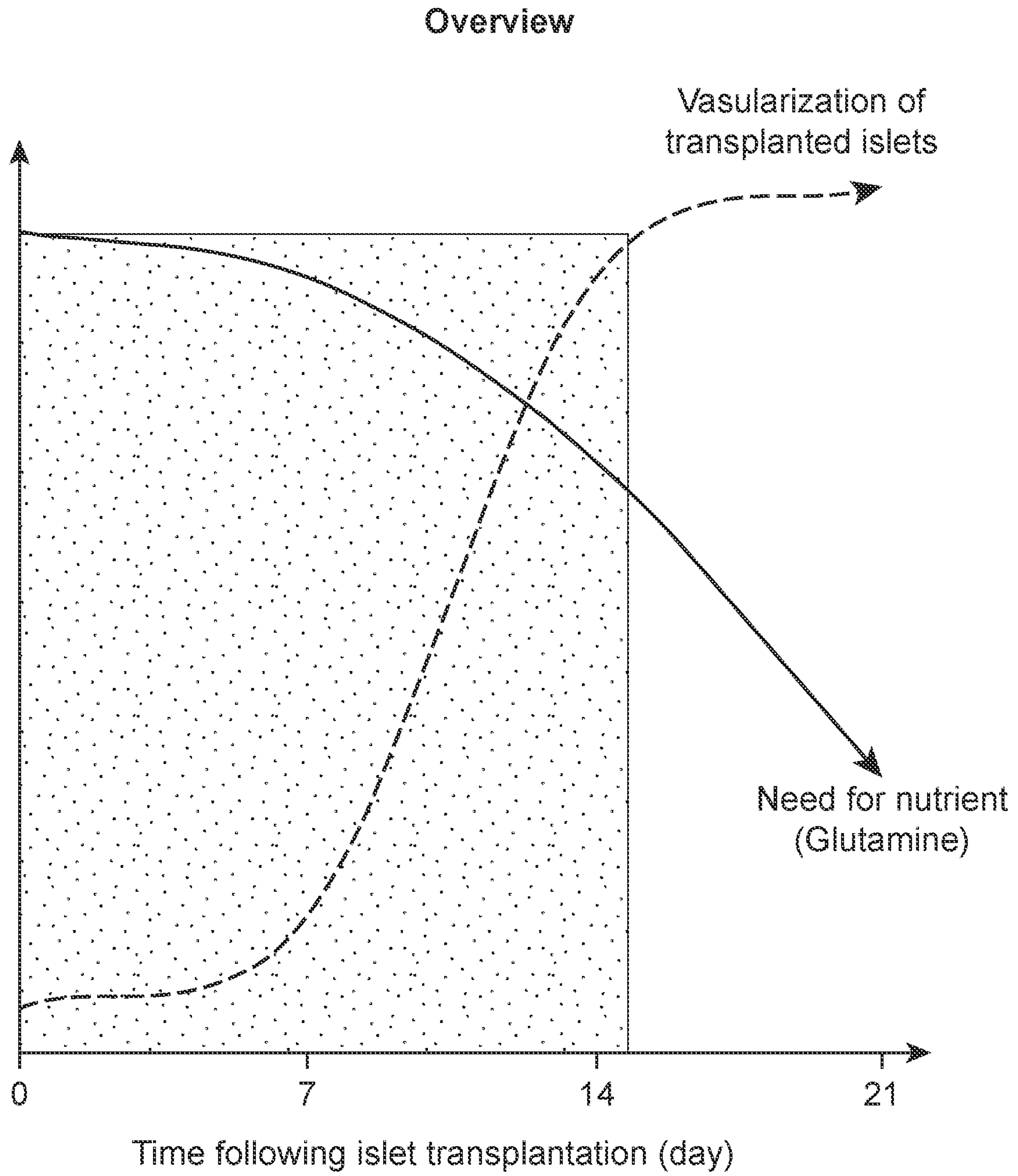
FIGS. 5A-5B. Role of glutamine and PDG-MSNPs in islets transplantation.
Figure 5B:
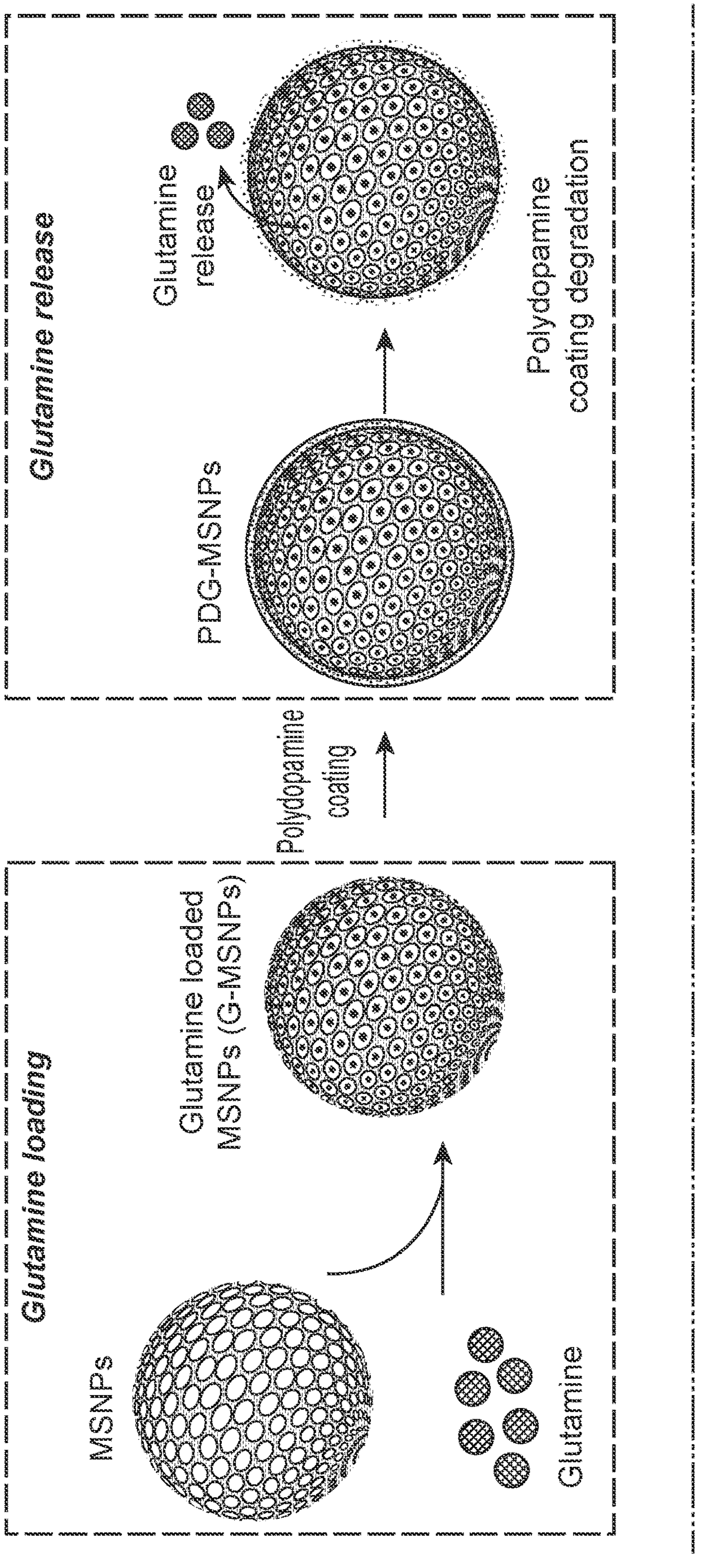
Figure 5B:
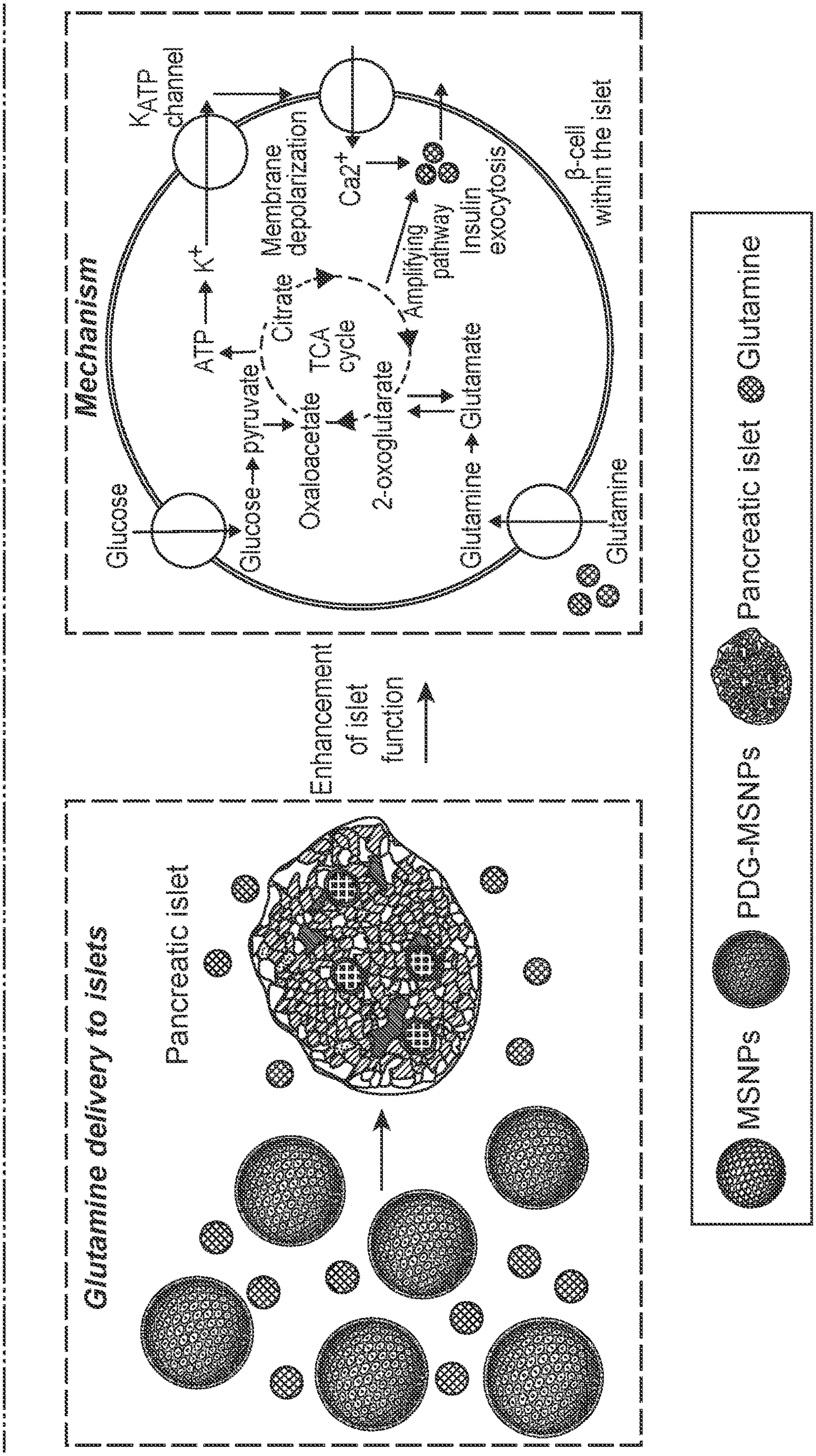

Histological analysis performed on tissue (i.e. kidneys) explanted 30 days post-transplantation showed that islets transplanted with PDG-MSNPs retained their native size, spherical morphology and intrinsic architecture; findings which were not consistently seen in islets transplanted alone (FIG. 4A). Moreover, animals transplanted with islets and PDG-MSNPs had a significantly greater number of viable transplanted islets compared to animals which did not receive any nanoparticles (i.e. islets only). Results were confirmed by quantifying the total islet area, which was higher for mice transplanted with islets supplemented with PDG-MSNPs compared to animals transplanted with islets only (total islet area: 0.4±0.02 vs. 0.1±0.02 $mm^2$, respectively $p<0.05$; FIG. 4B). When transplanted islets are healthier, they are normally intact and have a spherical structure.[28-30] However, when islets start to die, they lose their shape due to a loss in plasma membrane integrity and cell death.[31] Here, our results support the cytoprotective effect provided by PDG-MSNP, given that islet survival and function was improved when PDG-MSNP were transplanted with islets; accordingly, islets had a more spherical and organized structure when compared to transplanted islets alone. There was also a greater number of β cells (insulin staining: 86.9±4.5 vs. 55.7±12.4%; $p<0.05$; FIG. 4C) in addition to a reduction in surrounding inflammation (TNF-α staining: 2.9±0.4 vs. 12.5±0.7%; $p<0.05$; FIG. 4D) in mice transplanted with PDG-MSNPs compared to those transplanted with islets only. Furthermore, the analysis of serum and explanted kidneys demonstrated a significantly higher amount of insulin in animals transplanted with islets and PDG-MSNPs compared to those transplanted with islets only (for serum: 0.5±0.08 vs. 0.3±0.03 ng/mL; for kidney tissue: 0.6±0.04 vs. 0.4±0.08 μg/mL, respectively, $p<0.05$; FIGS. 4E-4F). Cytokine quantification was also performed in explanted kidneys to further investigate the immunological and inflammatory responses to transplanted islets alone vs transplanted islets supplemented with PDG-MSNPs. Our results showed an up-regulation of: monocyte chemoattractant protein-1 (MCP-1: 0.6±0.04 fold increase), vascular endothelial growth factor (VEGF: 0.7±0.05), macrophage inflammatory protein 1-beta (MIP-1β: 0.7±0.1 fold increase), granulocyte colony-stimulating factor (GCSF: 0.8±0.1 fold increase), granulocyte-macrophage colony-stimulating factor (GMCSF: 1.1±0.1 fold increase), EOTAXIN (1.7±0.2 fold increase), and Interleukin-22 (IL-22: 3.4±0.5 fold increase) in the kidneys which contained transplanted islets supplemented with PDG-MSNPs when compared to those containing transplanted islets only (FIG. 4G; $p<0.05$).

MSNPs have been used for different biomedical applications including delivery of proteins,[32] chemotherapeutic drugs,[33] cytokines[34] as well as cellular imaging.[35] To control the rate of release of these therapeutic agents to achieve effective local concentrations, great efforts have been made to test various parameters that can be modulated/controlled (i.e. temperature,[36] redox,[37] pH,[38] light,[39] and enzymes[40]) in order to create a responsive MSNP-based system. In addition, MSNPs can be coated with various polymers including poly(ethylene glycol) (PEG),[41] PEGylated lipid bilayer,[42] poly(N-isopropylacrylamide) (PNIPAAm) coating,[43] poly (L-lysine)[44] alginate,[45] and Poly(acrylic acid) (PAA).[46] Although promising, these approaches require a multi-step, complex, and often time-consuming chemistry with the use of toxic solvents to synthesize a coating layer on surface of MSNPs. An external (e.g. light[39]) or internal (e.g. pH[38]) stimulation is also then required to degrade the formed coating layer for the release of any encapsulated therapeutic agents. We used MSNPs for nutrient (glutamine) delivery to pancreatic islets, however, to prevent the immediate unloading of glutamine, and sustain its release over a period of 14 days (i.e. the approximate time it takes for islets to establish their own microcirculation following transplantation),[14] we used a simple (one-step synthesis), quick (<2 h), inexpensive (<$10 per $10^6$ MSNPs), and eco-friendly (no toxic solvents) method using polydopamine to coat our glutamine-loaded MSNPs (G-MSNPs). Our results showed that changing the polydopamine coating concentration (0.5-2 mg/mL) and time (0.5-2 h) allow us to control the release of glutamine from MSNPs over 1-14 days. PDG-MSNPs made using polydopamine at 0.5 mg/mL over 0.5 h, demonstrated significant increase in islet viability and function compared to islets supplemented with either glutamine alone (at the same concentration) or uncoated G-MSNPs. We attributed this to the sustained and controlled release of glutamine from MSNPs over time, instead of it being provided in a "burst phenomenon" to islets. Our in silico and in vitro results demonstrate that when islets are cultured with glutamine alone, their survival and function improves compared to when islets are cultured alone without glutamine; this is in keeping with previous work examining the role of glutamine on islet survival.[9] These results can be due to the fact that glutamine protects islets from nutrient deprivation by sustaining mitochondria oxidation via anaplerosis[9] and/or activating protein synthesis via mammalian target of rapamycin (mTOR), which is normally inhibited under nutrient-limiting conditions.[47]

When islets were transplanted with PDG-MSNPs, diabetic animals were able to re-establish glycemic control for 30 days post-transplantation with mice demonstrating a faster dynamic response to glucose challenges. Histological examination of the islet graft 30 days post-transplantation also confirmed that islets transplanted with PDG-MSNPs had better morphology, and reduced inflammation (decrease in TNF-α staining) compared to islets transplanted alone. In support of the ability of islets supplemented with PDG-MSNPs to facilitate islet revascularization, we also measured cytokine expression in the islet graft and found an upregulation of pro-angiogenic factors including VEGF. Indeed, VEGF has been shown to be key for islet revascularization following transplantation[48] and β-cells themselves have been shown to secrete large amounts of VEGF.[49] This is important given that a delay or insufficient revascularization in transplanted islets will affect their overall survival and function.[50] We also found that transplanted islets supplemented with PDG-MSNPs had a significantly higher expression of the anti-inflammatory cytokine IL-22[51], compared to transplanted islets alone. These results confirm the ability of glutamine in being able to reduce inflammation within the microenvironment of transplanted islets. However, a previous study did show that when glutamine alone is supplemented to stem cell derived β cells, although there was an improvement early after transplantation, this protective effect was not persistent.[9] Similarly, our in vitro (GSIS assay) and in vivo (metabolic analysis) data show that islets supplemented with glutamine alone were not as responsive compared to when islets were supplemented with PDG-MSNPs. One possible explanation for this could be due to the gradual and sustained delivery of glutamine to islets provided by PDG-MSNPs, compared to a one-time supplementation when glutamine alone is added to islets. Indeed, with high levels of glutamine provided in a burst supply, β cells may get overworked which over time may adversely affect both their survival and function.

The anatomical site that is currently being explored for islets to be transplanted with novel platforms such as bioscaffolds or nanoparticles is the omentum given that it has the ability to accommodate novel 3D platforms (i.e. nanoparticles and bioscaffolds[52-54]). Indeed, human clinical trials are already underway examining the feasibility of the omentum as a site for polydimethylsiloxane (PDMS) based bioscaffolds for islet transplantation.[55] In small animals, the epididymal fat pad (EFP) is often used as a surrogate site for the omentum in humans.[55-57] Hence, in our biocompatibility study we examined both the EFP and the subcutaneous space with our PDG-MSNPs given that these sites both have the potential to be widely adopted in human patients. Since our current data support that PDG-MSNPs can augment islet survival and function with excellent biocompatibility, future research will now aim to examine islet transplantation with PDG-MSNPs, over the short and long term, at these other sites either alone or in combination with 3D bioscaffolds. In the latter case, bioscaffolds can be easily scaled to 100 $cm^3$ to accommodate the required number of islets for human islet transplantation (i.e. a typical islet transplant requires 5,000 islets per kg which, on average, translates to approximately 350,000-450,000 islets[58]). Given that islets housed in these bioscaffolds will require nutrients until they are revascularized, combining our PDG-MSNPs with bioscaffolds can address this issue to ensure islets have the optimal microenvironment following their transplantation. Finally, our PDG-MSNP is composed of two components: MSNP and PD. In general, silica is recognized as "safe" by the FDA,[59] and is often used in tablet-form in drug formulations as an excipient, and frequently also taken as a dietary supplement for nourishing skin and nails[59]. Recently, silica nanoparticles in the form of 'C-dots' (Cornell dots)[60] were FDA approved for a phase I human clinical trial.[61] While we,[62,63] and others,[64-66] have shown PD is a biocompatible material, to our knowledge there are currently no clinical trials which have used PD. Taken together, PDG-MSNPs should therefore be well placed to be assessed in human clinical trials following their optimization for use in islet transplantation.

Conclusion

In summary, our results show the potential of PDG-MSNPs to be used as a translatable platform for the controlled and sustained delivery of nutrients in the short term (i.e. over 14 days), which is especially important in the context of islet transplantation. The present in vitro and in vivo data show that PDG-MSNPs not only protect islets, but they also promote their survival and function.

TABLE 1

Summary of amino acids reported in the literature that can affect islet survival and function

| Nutrients (amino acids) | Enhanced islet survival | Enhanced islet function | Cyto-protective effects on islets | Islet high demand | Decreased inflammation |
|---|---|---|---|---|---|
| Glutamine | Yes | Yes | Yes | Yes | Yes |
| Alanine | Yes | Yes | No | Yes | No |
| Cysteine | No | No | Yes | No | No |
| Tryptophan | Yes | Yes | No | No | No |
| Leucine | No | Yes | Yes | No | No |
| Methionine | No | No | No | No | No |
| Isoleucine | No | Yes | No | No | No |
| Arginine | No | Yes | No | No | No |
| Lysine | No | Yes | No | No | No |
| Proline | No | Yes | No | No | No |
| Homocysteine | No | No | No | No | No |

| Nutrients (amino acids) | Maintained function of various organs | Precursor of proteins, and amino sugars | Most abundant in the blood | References |
|---|---|---|---|---|
| Glutamine | Yes | Yes | Yes | 6,8,18-20 |
| Alanine | No | No | Yes | 6,8,18,19 |
| Cysteine | No | No | No | 18 |
| Tryptophan | No | No | No | 18,21 |
| Leucine | No | No | No | 18,19 |
| Methionine | No | No | No | 18 |
| Isoleucine | No | No | No | 9 |
| Arginine | No | No | No | 9,22 |
| Lysine | No | No | No | 19 |
| Proline | No | No | No | 19 |
| Homocysteine | No | No | No | 19 |

Table 2. Long-term biocompatibility of optimized PDG-MSNPs. Blood metabolic, chemistry, and liver panels from mice that have been implanted with optimized PDG-MSNPs (obtained using a PD coating of 0.5 mg/mL for 0.5 h) for 24 weeks. The normal range for each parameter analyzed is listed in the table. Results are expressed as the average±SEM (n=6). We tested the biocompatibility of our nanoparticles in both the epididymal fat pad (a common site for bioscaffold implantation in small animal models which is representative of the omentum in humans)[31,32] as well as the subcutaneous tissue (a site which can be easily accessed in patients and has the potential to be widely adopted as a space for bioscaffold implantation with minimal intervention).[33-34] The blood analysis performed 24 weeks post-implantation confirmed that PDG-MSNPs did not affect the metabolic, chemistry, and liver panels of the mice that have been implanted with particles for 24 weeks. All the values remained within their respective normal range.[35,36] These results show that PDG-MSNPs are biocompatible and cause a minimal change in blood biochemical makers at 6 months following implantation at either site. These findings are in keeping with their ability to be used in vivo and hence their potential to be clinically translated.

| Test | Mice implanted with PDG-MSNPs | Normal Range |
|---|---|---|
| METABOLIC PANEL | | |
| Sodium | 150 ± 2 | 146-151 mmol/L |
| Chloride | 112 ± 1 | 107-111 mmol/L |
| Carbon Dioxide | 21 ± 2 | 20-29 mmol/L |

-continued

| Test | Mice implanted with PDG-MSNPs | Normal Range |
|---|---|---|
| Potassium | 4.5 ± 0.5 | 3.0-9.6 mmol/L |
| Blood Urea Nitrogen | 20 ± 3 | 20.3-24.7 mg/dL |
| Creatinine | 0.14 ± 0.03 | 0.1-1.1 mg/dL |
| CHEMISTRY PANEL | | |
| Calcium | 9.2 ± 0.2 | 8.9-9.7 mg/dL |
| Phosphorus | 7.2 ± 0.5 | 4.2-8.5 mg/dL |
| T. Protein | 4.7 ± 0 | 4.5-6.5 g/dL |
| Albumin | 2.5 ± 0.1 | 2.5-2.8 g/dL |
| LIVER PANEL | | |
| Alkaline Phosphatase* | 57 ± 5 | 44-147 IU/L |
| Aspartate Aminotransferase (AST) | 71 ± 41 | 10-45 U/L |
| Alanine Aminotransferase (ALT) | 70 ± 51 | 10-35 U/L |
| Total Bilirubin | 0.1 ± 0.05 | 0-1.0 mg/dL |

Table 3. Statistical analysis for DLS analysis of uncoated- and polydopamine coated-G-MSNPs obtained using different polydopamine coating concentrations (0, 0.5, 1, 2 mg/mL). The p values of <0.05 (*), <0.01 (), <0.001 (*) and <0.0001 (****) were considered to be statistically significant, while ns was not statistically significant.

| Diameter size (nm) | 0 mg/mL vs 0.5 mg/mL | 0 mg/mL vs 1 mg/mL | 0 mg/mL vs 2 mg/mL | 0.5 mg/mL vs 1 mg/mL | 0.5 mg/ml vs 2 mg/mL | 1 mg/mL vs 2 mg/mL |
|---|---|---|---|---|---|---|
| 0.40-50.70 | ns | ns | ns | ns | ns | ns |
| 58.8 | **** | **** | **** | ns | ns | ns |
| 68.1 | **** | **** | **** | ns | ns | ns |
| 78.8 | **** | **** | **** | *** | * | **** |
| 91.3 | **** | **** | **** | ns | ns | * |
| 106 | ns | **** | ns | *** | ns | * |
| 122 | **** | ns | ** | **** | ns | ns |
| 142 | **** | **** | **** | ** | * | ns |
| 164 | **** | **** | **** | ns | ns | ns |
| 190 | **** | **** | **** | ns | ns | ns |
| 220 | ** | **** | **** | ** | ns | * |
| 255 | ns | **** | ns | *** | ns | ** |
| 295 | ns | ns | ns | ns | ns | ns |
| 342-531 | ns | ns | ns | ns | ns | ns |

Table 4. Statistical analysis for DLS analysis of uncoated- and polydopamine coated-G-MSNPs obtained using different polydopamine coating times (0, 0.5, 1, 2 h). The p values of <0.05 (*), <0.01 (), <0.001 (*) and <0.0001 (****) were considered to be statistically significant, while ns was not statistically significant.

| Diameter size (nm) | 0 h vs 0.5 h | 0 h vs 1 h | 0 h vs 2 h | 0.5 h vs 1 h | 0.5 h vs 2 h | 1 h vs 2 h |
|---|---|---|---|---|---|---|
| 040-50.70 | ns | ns | ns | ns | ns | ns |
| 58.8 | **** | **** | **** | ns | ns | ns |
| 68.1 | **** | **** | **** | ns | ns | ns |
| 78.8 | **** | **** | **** | *** | ns | ** |
| 91.3 | **** | **** | **** | * | * | **** |
| 106 | ns | ns | **** | ns | **** | **** |
| 122 | **** | **** | ns | ns | **** | ** |
| 142 | **** | **** | **** | * | ns | ns |
| 164 | **** | **** | **** | * | ns | 3 |
| 190 | **** | **** | **** | ns | *** | **** |
| 220 | *** | ** | **** | ns | **** | **** |
| 255 | ns | ns | ** | ns | ns | * |
| 295 | ns | ns | ns | ns | ns | ns |
| 342-531 | ns | ns | ns | ns | ns | ns |

REFERENCES (1) Biarnes, M.; Montolio, M.; Nacher, V.; Raurell, M.; Soler, J.; Montanya, E. B-Cell Death and Mass in Syngeneically Transplanted Islets Exposed To Short- and Long-Term Hyperglycemia. *Diabetes* 2002, 51(1), 66-72.

(2) Nilsson, B.; Ekdahl, K. N.; Korsgren, O. Control of Instant Blood-Mediated Inflammatory Reaction to Improve Islets of Langerhans Engraftment. *Current Opinion in Organ Transplantation.* 2011, pp 620-626.

(3) Pepper, A. R.; Gala-Lopez, B.; Ziff, O.; Shapiro, A. M. J. Revascularization of Transplanted Pancreatic Islets and Role of the Transplantation Site. *Clin. Dev. Immunol.* 2013, 2013, 1-13.

(4) Carlsson, P. O.; Palm, F.; Andersson, A.; Liss, P. Markedly Decreased Oxygen Tension in Transplanted Rat Pancreatic Islets Irrespective of the Implantation Site. *Diabetes* 2001, 50 (3), 489-495.

(5) Komatsu, H.; Cook, C.; Wang, C. H.; Medrano, L.; Lin, H.; Kandeel, F.; Tai, Y. C.; Mullen, Y. Oxygen Environment and Islet Size Are the Primary Limiting Factors of Isolated Pancreatic Islet Survival. *PLoS One* 2017, 12 (8).

(6) Komatsu, H.; Kang, D.; Medrano, L.; Barriga, A.; Mendez, D.; Rawson, J.; Omori, K.; Ferreri, K.; Tai, Y. C.; Kandeel, F.; et al. Isolated Human Islets Require Hyperoxia to Maintain Islet Mass, Metabolism, and Function. *Biochem. Biophys. Res. Commun.* 2016, 470 (3), 534-538.

(7) Dixon, G.; Nolan, J.; McClenaghan, N.; Flatt, P. R.; Newsholme, P. A Comparative Study of Amino Acid Consumption by Rat Islet Cells and the Clonal Beta-Cell Line BRIN-BD11—The Functional Significance of L-Alanine. *J. Endocrinol.* 2003, 179 (3), 447-454.

(8) Newsholme, P.; Brennan, L.; Bender, K. Amino Acid Metabolism, β-Cell Function, and Diabetes. *Diabetes* 2006, 55 (SUPPL. 2).

(9) Faleo, G.; Russ, H. A.; Wisel, S.; Parent, A. V.; Nguyen, V.; Nair, G. G.; Freise, J. E.; Villanueva, K. E.; Szot, G. L.; Hebrok, M.; et al. Mitigating Ischemic Injury of Stem Cell-Derived Insulin-Producing Cells after Transplant. *Stem Cell Reports* 2017, 9 (3), 807-819.

(10) Liu, Z.; Jeppesen, P. B.; Gregersen, S.; Chen, X.; Hermansen, K. Dose- and Glucose-Dependent Effects of Amino Acids on Insulin Secretion from Isolated Mouse Islets and Clonal INS-1E Beta-Cells. *Rev. Diabet. Stud.* 2008, 5 (4), 232-244.

(11) Jang, H. J.; Kwak, J. H.; Cho, E. Y.; We, Y. M.; Lee, Y. H.; Kim, S. C.; Han, D. J. Glutamine Induces Heat-Shock Protein-70 and Glutathione Expression and Attenuates Ischemic Damage in Rat Islets. *Transplant. Proc.* 2008, 40 (8), 2581-2584.

(12) Lindström, P.; Sehlin, J. Aromatic Amino Acids and Pancreatic Islet Function: A Comparison of I-Tryptophan and I-5-Hydroxytryptophan. *Mol. Cell. Endocrinol.* 1986, 48 (2-3), 121-126.

(13) Neuman, J. C.; Truchan, N. A.; Joseph, J. W.; Kimple, M. E. A Method for Mouse Pancreatic Islet Isolation and Intracellular CAMP Determination. *J. Vis. Exp.* 2014, No. 88, e50374.

(14) Mullooly, N.; Vernon, W.; Smith, D. M.; Newsholme, P. Elevated Levels of Branched-Chain Amino Acids Have Little Effect on Pancreatic Islet Cells, but I-Arginine Impairs Function through Activation of the Endoplasmic Reticulum Stress Response. *Exp. Physiol.* 2014.

(15) Cunningham, G. A.; Mcclenaghan, N. H.; Flatt, P. R.; Newsholme, P. L-Alanine Induces Changes in Metabolic and Signal Transduction Gene Expression in a Clonal Rat Pancreatic β-Cell Line and Protects from pro-Inflammatory Cytokine-Induced Apoptosis. *Clin. Sci.* 2005, 109 (5), 447-455.

(16) Curi, R.; Lagranha, C. J.; Doi, S. Q.; Sellitti, D. F.; Procopio, J.; Pithon-Curi, T. C.; Corless, M.; Newsholme, P. Molecular Mechanisms of Glutamine Action. *Journal of Cellular Physiology.* 2005, pp 392-401.

(17) Smith, R. J.; Wilmore, D. W. Glutamine Nutrition and Requirements. *J. Parenter. Enter. Nutr.* 2009, 14 (4_suppl), 94S-99S.

(18) Moreno-Villaécija, M. Á.; Sedó-Vegara, J.; Guisasola, E.; Baeza, A.; Regi, M. V.; Nador, F.; Ruiz-Molina, D. Polydopamine-like Coatings as Payload Gatekeepers for Mesoporous Silica Nanoparticles. *ACS Appl. Mater. Interfaces* 2018, 10 (9), 7661-7669.

(19) Baeza, A.; Colilla, M.; Vallet-Regi, M. Advances in Mesoporous Silica Nanoparticles for Targeted Stimuli-Responsive Drug Delivery. *Expert Opin. Drug Deliv.* 2014, 12 (2), 319-337.

(20) Liu, R.; Guo, Y.; Odusote, G.; Qu, F.; Priestley, R. D. Core-Shell Fe3O4 Polydopamine Nanoparticles Serve Multipurpose as Drug Carrier, Catalyst Support and Carbon Adsorbent. *ACS Appl. Mater. Interfaces* 2013, 5 (18), 9167-9171.

(21) Hwang, J. H.; Noh, Y. W.; Choi, J. H.; Noh, J. R.; Kim, Y. H.; Gang, G. T.; Kim, K. S.; Park, H. S.; Lim, Y. T.; Moon, H.; et al. In Vivo Imaging of Islet Transplantation Using PLGA Nanoparticles Containing Iron Oxide and Indocyanine Green. *Magn. Reson. Med.* 2014, 71 (3), 1054-1063.

(22) Wang, P.; Yoo, B.; Yang, J.; Zhang, X.; Ross, A.; Pantazopoulos, P.; Dai, G.; Moore, A. GLP-1R-Targeting Magnetic Nanoparticles for Pancreatic Islet Imaging. *Diabetes* 2014, 63 (5), 1465-1474.

(23) Pham, T. T.; Nguyen, T. T.; Pathak, S.; Regmi, S.; Nguyen, H. T.; Tran, T. H.; Yong, C. S.; Kim, J. O.; Park, P. H.; Park, M. H.; et al. Tissue Adhesive FK506-Loaded Polymeric Nanoparticles for Multi-Layered Nano-Shielding of Pancreatic Islets to Enhance Xenograft Survival in a Diabetic Mouse Model. *Biomaterials* 2018, 154, 182-196.

(24) Morini, S.; Brown, M. L.; Cicalese, L.; Elias, G.; Carotti, S.; Gaudio, E.; Rastellini, C. Revascularization and Remodelling of Pancreatic Islets Grafted under the Kidney Capsule. *J. Anat.* 2007, 210 (5), 565-577.

(25) Soares, D. C. F.; De Sousa Andrada, A.; Ramaldes, G. A. Silica Nanoparticles Containing Gadolinium Complex as Potential Alternative to Anticancer Radiotherapy. *Part. Sci. Technol.* 2015, 33 (4), 331-338.

(26) Yin, N. Q.; Wu, P.; Yang, T. H.; Wang, M. Preparation and Study of a Mesoporous Silica-Coated Fe3O4 Photothermal Nanoprobe. *RSC Adv.* 2017, 7 (15), 9123-9129.

(27) Santha Moorthy, M.; Subramanian, B.; Panchanathan, M.; Mondal, S.; Kim, H.; Lee, K. D.; Oh, J. Fucoidan-Coated Core-Shell Magnetic Mesoporous Silica Nanoparticles for Chemotherapy and Magnetic Hyperthermia-Based Thermal Therapy Applications. *New J. Chem.* 2017, 41 (24), 15334-15346.

(28) lonescu-Tirgoviste, C.; Gagniuc, P. A.; Gubceac, E.; Mardare, L.; Popescu, I.; Dima, S.; Militaru, M. A 3D Map of the Islet Routes throughout the Healthy Human Pancreas. *Sci. Rep.* 2015, 5.

(29) Huang, H. H.; Harrington, S.; Stehno-Bittel, L. The Flaws and Future of Islet Volume Measurements. *Cell Transplantation.* 2018, pp 1017-1026.

(30) Rackham, C. L.; Jones, P. M.; King, A. J. F. Maintenance of Islet Morphology Is Beneficial for Transplantation Outcome in Diabetic Mice. *PLoS One* 2013, 8 (2).

(31) Kaviani, M.; Keshtkar, S.; Azarpira, N.; Aghdaei, M. H.; Geramizadeh, B.; Karimi, M. H.; Shamsaeefar, A.; Motazedian, N.; Nikeghbalian, S.; Al-Abdullah, I. H.; et al. Cytoprotective Effects of Olesoxime on Isolated Human Pancreatic Islets in Order to Attenuate Apoptotic Pathway. *Biomed. Pharmacother.* 2019, 112.

(32) Liu, B.; Ejaz, W.; Gong, S.; Kurbanov, M.; Canakci, M.; Anson, F.; Thayumanavan, S. Engineered Interactions with Mesoporous Silica Facilitate Intracellular Delivery of Proteins and Gene Editing. *Nano Lett.* 2020, 20 (5), 4014-4021.

(33) Llopis-Lorente, A.; Garciá-Fernández, A.; Murillo-Cremaes, N.; Hortelaõ, A. C.; Patinõ, T.; Villalonga, R.; Sancenón, F.; Martinez-Máñez, R.; Sánchez, S. Enzyme-Powered Gated Mesoporous Silica Nanomotors for on-Command Intracellular Payload Delivery. *ACS Nano* 2019, 13(10), 12171-12183.

(34) Kwon, D.; Cha, B. G.; Cho, Y.; Min, J.; Park, E. B.; Kang, S. J.; Kim, J. Extra-Large Pore Mesoporous Silica Nanoparticles for Directing in Vivo M2 Macrophage Polarization by Delivering IL-4. *Nano Lett.* 2017, 17 (5), 2747-2756.

(35) Sun, Q.; You, Q.; Wang, J.; Liu, L.; Wang, Y.; Song, Y.; Cheng, Y.; Wang, S.; Tan, F.; Li, N. Theranostic Nanoplatform: Triple-Modal Imaging-Guided Synergistic Cancer Therapy Based on Liposome-Conjugated Mesoporous Silica Nanoparticles. *ACS Appl. Mater. Interfaces* 2018, 10(2), 1963-1975.

(36) You, Y. Z.; Kalebaila, K. K.; Brock, S. L.; Oupický, D. Temperature-Controlled Uptake and Release in PNIPAM-Modified Porous Silica Nanoparticles. *Chem. Mater.* 2008, 20 (10), 3354-3359.

(37) Sauer, A. M.; Schlossbauer, A.; Ruthardt, N.; Cauda, V.; Bein, T.; Bräuchle, C. Role of Endosomal Escape for Disulfide-Based Drug Delivery from Colloidal Mesoporous Silica Evaluated by Live-Cell Imaging. *Nano Lett.* 2010, 10 (9), 3684-3691.

(38) Park, C.; Oh, K.; Lee, S. C.; Kim, C. Controlled Release of Guest Molecules from Mesoporous Silica Particles Based on a PH-Responsive Polypseudorotaxane Motif. *Angew. Chemie—Int. Ed.* 2007, 46 (9), 1455-1457.

(39) Lu, J.; Choi, E.; Tamanoi, F.; Zink, J. I. Light-Activated Nanoimpeller-Controlled Drug Release in Cancer Cells. *Small* 2008, 4 (4), 421-426. https://doi.org/10.1002/smll.200700903.

(40) Schlossbauer, A.; Kecht, J.; Bein, T. Biotin-Avidin as a Protease-Responsive Cap System for Controlled Guest Release from Colloidal Mesoporous Silica. *Angew. Chemie—Int. Ed.* 2009, 48 (17), 3092-3095.

(41) Mu, S.; Liu, Y.; Wang, T.; Zhang, J.; Jiang, D.; Yu, X.; Zhang, N. Unsaturated Nitrogen-Rich Polymer Poly(L-Histidine) Gated Reversibly Switchable Mesoporous Silica Nanoparticles Using "Graft to" Strategy for Drug Controlled Release. *Acta Biomater.* 2017, 63, 150-162.

(42) Lin, J.; Cai, Q.; Tang, Y.; Xu, Y.; Wang, Q.; Li, T.; Xu, H.; Wang, S.; Fan, K.; Liu, Z.; et al. PEGylated Lipid Bilayer Coated Mesoporous Silica Nanoparticles for Co-Delivery of Paclitaxel and Curcumin: Design, Characterization and Its Cytotoxic Effect. *Int. J. Pharm.* 2018, 536 (1), 272-282.

(43) Hegazy, M.; Zhou, P.; Wu, G.; Wang, L.; Rahoui, N.; Taloub, N.; Huang, X.; Huang, Y. Construction of Polymer Coated Core-Shell Magnetic Mesoporous Silica Nanoparticles with Triple Responsive Drug Delivery. *Polym. Chem.* 2017, 8 (38), 5852-5864.

(44) Du, X.; Zhang, T.; Ma, G.; Gu, X.; Wang, G.; Li, J. Glucose-Responsive Mesoporous Silica Nanoparticles to Generation of Hydrogen Peroxide for Synergistic Cancer Starvation and Chemistry Therapy. *Int. J. Nanomedicine* 2019, 14, 2233-2251.

(45) Yuan, N. ning; Li, S. ji; Li, G. qiang. Sodium Alginate Coated Mesoporous Silica for Dual Bio-Responsive Controlled Drug Delivery. *J. Drug Deliv. Sci. Technol.* 2018, 46, 348-353.

(46) Liu, J.; Liang, H.; Li, M.; Luo, Z.; Zhang, J.; Guo, X.; Cai, K. Tumor Acidity Activating Multifunctional Nanoplatform for NIR-Mediated Multiple Enhanced Photodynamic and Photothermal Tumor Therapy. *Biomaterials* 2018, 157, 107-124.

(47) Yu, L.; McPhee, C. K.; Zheng, L.; Mardones, G. A.; Rong, Y.; Peng, J.; Mi, N.; Zhao, Y.; Liu, Z.; Wan, F.; et al. Termination of Autophagy and Reformation of Lysosomes Regulated by MTOR. *Nature* 2010, 465 (7300), 942-946.

(48) Brissova, M.; Shostak, A.; Shiota, M.; Wiebe, P. O.; Poffenberger, G.; Kantz, J.; Chen, Z.; Carr, C.; Jerome, W. G.; Chen, J.; et al. Pancreatic Islet Production of Vascular Endothelial Growth Factor-A Is Essential for Islet Vascularization, Revascularization, and Function. Diabetes 2006, 55 (11), 2974-2985.

(49) Peiris, H.; Bonder, C. S.; Coates, P. T. H.; Keating, D. J.; Jessup, C. F. The β-Cell/EC Axis: How Do Islet Cells Talk to Each Other? *Diabetes.* 2014, pp 3-11.

(50) Del Toro-Arreola, A.; Robles-Murillo, A. K.; Daneri-Navarro, A.; Rivas-Carrillo, J. D. The Role of Endothelial Cells on Islet Function and Revascularization after Islet Transplantation. *Organogenesis* 2016, 12 (1), 28-32.

(51) Parks, O. B.; Pociask, D. A.; Hodzic, Z.; Kolls, J. K.; Good, M. Interleukin-22 Signaling in the Regulation of Intestinal Health and Disease. *Frontiers in Cell and Developmental Biology.* 2016.

(52) Razavi, M.; Hu, S.; Thakor, A. S. A Collagen Based Cryogel Bioscaffold Coated with Nanostructured Polydopamine as a Platform for Mesenchymal Stem Cell Therapy. *J. Biomed. Mater. Res.—Part A* 2018, 106 (8), 2213-2228.

(53) Razavi, M.; Primavera, R.; Kevadiya, B. D.; Wang, J.; Buchwald, P.; Thakor, A. S. A Collagen Based Cryogel Bioscaffold That Generates Oxygen for Islet Transplantation. *Adv. Funct. Mater.* 2020, 30 (15).

(54) Razavi, M.; Thakor, A. S. An Oxygen Plasma Treated Poly(Dimethylsiloxane) Bioscaffold Coated with Polydopamine for Stem Cell Therapy. *J. Mater. Sci. Mater. Med.* 2018, 29 (5).

(55) Schmidt, C. Pancreatic Islets Find a New Transplant Home in the Omentum. *Nat. Biotechnol.* 2017, 35 (1), 8-8.

(56) Berman, D. M.; Molano, R. D.; Fotino, C.; Ulissi, U.; Gimeno, J.; Mendez, A. J.; Kenyon, N. M.; Kenyon, N. S.; Andrews, D. M.; Ricordi, C.; et al. Bioengineering the Endocrine Pancreas: Intraomental Islet Transplantation within a Biologic Resorbable Scaffold. *Diabetes* 2016, 65 (5), 1350-1361.

(57) Gibly, R. F.; Zhang, X.; Lowe, W. L.; Shea, L. D. Porous Scaffolds Support Extrahepatic Human Islet Transplantation, Engraftment, and Function in Mice. *Cell Transplant.* 2013, 22 (5), 811-819.

(58) McCall, M.; James Shapiro, A. M. Update on Islet Transplantation. *Cold Spring Harb. Perspect. Med.* 2012, 2 (7).

(59) Rosenholm, J. M.; Mamaeva, V.; Sahlgren, C.; Linden, M. Nanoparticles in Targeted Cancer Therapy: Mesoporous Silica Nanoparticles Entering Preclinical Development Stage. *Nanomedicine.* 2012, pp 111-120.
(60) Ow, H.; Larson, D. R.; Srivastava, M.; Baird, B. A.; Webb, W. W.; Wiesnert, U. Bright and Stable Core-Shell Fluorescent Silica Nanoparticles. *Nano Lett.* 2005, 5 (1), 113-117.
(61) Benezra, M.; Penate-Medina, O.; Zanzonico, P. B.; Schaer, D.; Ow, H.; Burns, A.; DeStanchina, E.; Longo, V.; Herz, E.; Iyer, S.; et al. Multimodal Silica Nanoparticles Are Effective Cancer-Targeted Probes in a Model of Human Melanoma. *J. Clin. Invest.* 2011, 121 (7), 2768-2780.
(62) Razavi, M.; Hu, S.; Thakor, A. S. A Collagen Based Cryogel Bioscaffold Coated with Nanostructured Polydopamine as a Platform for Mesenchymal Stem Cell Therapy. *J. Biomed. Mater. Res.—Part A* 2018, 106 (8), 2213-2228.
(63) Razavi, M.; Thakor, A. S. An Oxygen Plasma Treated Poly(Dimethylsiloxane) Bioscaffold Coated with Polydopamine for Stem Cell Therapy. *J. Mater. Sci. Mater. Med.* 2018, 29 (5).
(64) Liu, X.; Cao, J.; Li, H.; Li, J.; Jin, Q.; Ren, K.; Ji, J. Mussel-Inspired Polydopamine: A Biocompatible and Ultrastable Coating for Nanoparticles in Vivo. *ACS Nano* 2013, 7 (10), 9384-9395.
(65) Lee, D. J.; Lee, Y. T.; Zou, R.; Daniel, R.; Ko, C. C. Polydopamine-Laced Biomimetic Material Stimulation of Bone Marrow Derived Mesenchymal Stem Cells to Promote Osteogenic Effects. *Sci. Rep.* 2017, 7 (1), 12984.
(66) Jun, D. R.; Moon, S. K.; Choi, S. W. Uniform Polydimethylsiloxane Beads Coated with Polydopamine and Their Potential Biomedical Applications. *Colloids Surfaces B Biointerfaces* 2014, 121, 395-399.

Example 2

Materials and Methods

1. PDG-MSNPs Synthesis

MSNPs were synthesized employing a modified Stöber method using tetraethyl orthosilicate (TEOS) in the presence of cetyl trimethylammonium bromide (CTAB) as structure directing agent.[1] In brief, CTAB (1 g; Fischer Scientific, USA), milliQ $H_2O$ (480 mL) and sodium hydroxide (2 M, 3.5 mL; Fischer Scientific, USA) were stirred and heated to 80° C. Next, TEOS (5 mL; 98%, Fischer Scientific, USA) was added dropwise at 0.25 mL/min to create a white suspension. The obtained white suspension was then magnetically stirred (600 rpm) for further 2 h at 95° C. The reaction mixture was collected by centrifugation (10,000 g for 15 min at 4° C.) and washed 3 times in water and ethanol 95% v/v. The surfactant, CTAB, was removed by ionic exchange using a solution of ammonium nitrate (10 mg/mL, Fischer Scientific, USA) in ethanol 95% v/v under magnetic stirring (250 rpm) for 24 h at room temperature. The nanoparticles were collected by centrifugation (10,000 g for 15 min at 4° C.), and washed 3 times with ethanol 95% v/v. Next, glutamine was loaded into the synthesized MSNPs. Specifically, 500 mg of MSNPs were added into 10 mL of glutamine solution (10, 30 and 50 mM in water) and mixed at room temperature for 48 h (see paragraph 5.3). Following, the surface of glutamine-loaded MSNPs (G-MSNPs) was coated using dopamine solution in Tris buffer (10 mM, pH=8.5).[2] Briefly, 500 mg of G-MSNPs were added into 10 mL of dopamine solutions at different concentrations (0.5, 1, and 2 mg/mL) for 0.5 h or at concentration 0.5 mg/mL for different incubation times (0.5, 1, and 2 h). G-MSNPs were mixed with polydopamine solutions (at the concentrations and times previously discussed) in an orbital shaker in the dark. The resultant polydopamine coated glutamine-loaded MSNPs (PDG-MSNPs) were collected by centrifugation (10,000 g for 15 min at 4° C.), washed 3 times in phosphate buffered saline (PBS; Gibco, USA) and dried at room temperature overnight. To avoid any reaction of polydopamine with PBS, and G release, during the washing process, we minimized the process of mixing PDG-MSNPs with PBS (<15 s).

2. PDG-MSNPs Characterization

The average size and size distribution of MSNPs, G-MSNPs and PDG-MSPs have been analyzed using dynamic light scattering. Samples were diluted with milliQ water (1:50 v/v) to avoid multiscattering phenomena and analyzed at 25° C. with a Zetasizer Nano ZS90 (Malvern, UK), equipped with a 4.5 mW laser diode and operating at 670 nm as a light source, and the scattered photons were detected at 173°. A third order cumulative fitting autocorrelation function is applied to measure the average size and the size distribution. The analysis was performed according to the following instrumental setup: (i) a real refractive index of 1.59; (ii) an imaginary refractive index of 0.0; (iii) a medium refractive index of 1.330; (iv) a medium viscosity of 1.0 mPa s; and (v) a medium dielectric constant of 80.4.

X-ray diffraction (XRD) analysis was carried out in 2θ range of 2-80° using a PANalytical Empyrean diffractometer (PANalytical Inc., Westborough, MA, USA) with Cu-Kα radiation (1.5418 Å) at 40 kV, 45 mA setting. A mask of 20 mm and a divergence slit of ⅛° were used on the incident beam path. The powder samples were spread on a low background silicon sample holder and the diffraction data was collected in steps of 0.013° by continuously scanning the source and the solid state PIXcel3D detector with a scan rate of 0.01°/s. Ni-foil Kβ filter was introduced in front of the detector to remove possible spurious peaks originating from Cu-Kβ radiation.

Size of nanoparticles and polydopamine coating were also confirmed using Transmission Electron Microscopy (TEM) (Hitachi H7500 TEM) by adding 2 μL of nanoparticle solution on a copper grid (FCF-400-CU, Electron Microscopy Sciences-EMS, Hatfield, PA, USA). A Zetasizer Nano ZS90 (Malvern, UK) was used to measure the surface charge (zeta-potential, mV) of uncoated and polydopamine-coated G-MSNPs obtained using different PD coating concentrations (0.5-2 mg/mL) and times (0.5-2 h). Samples were diluted with milliQ water (1:50 v/v) to avoid multiscattering phenomena and analyzed at 25° C. The measurement was performed by using a Smoluchowski constant F (Ka) of 1.5 as a function of the electrophoretic mobility. Measurements represented the average of three batches (10 runs per measurements).

The pore diameter within the nanoparticles was evaluated using a standard nitrogen absorption Brunauer, Emmett and Teller test. Samples were degassed for 48 h at 350° C. before measuring the nitrogen adsorption by using a Micromeritics ASAP 2460 Accelerated Surface Area and Porosimetry System with a smart VacPrep system for degassing. The scan parameters were as follow: p/p0=0.02-0.2 Steps 0.02 (9 pts), p/p0=0.25-0.8 Steps 0.5 (12 pts) and p/p0=0.825-0.995 steps 0.25 (9 pts) followed by returning to p/p0=0.08.

3. Determination of Glutamine Loading and Release from PDG-MSNPs

Glutamine solutions were created at concentrations of 10, 30, and 50 mM by dissolving glutamine powder in deionized water. MSNPs (500 mg) were then added into the glutamine solutions (10 mL) and stirred at room temperature for 48 h. At 1, 4, 24, and 48 h following the addition of MSNPs (500 mg) into glutamine solution, the loading efficiency was calculated by measuring the concentration of glutamine remaining in solution using a Bradford assay,[3] according to Equation 1:

$$\text{Glutamine Loading (\%)} = 100 - \left[\left(\frac{\text{mass of glutamine unloaded in } MSNPs}{tot \text{ mass of glutamine}}\right)\right] \times 100 \quad \text{(Equation 1)}$$

While, to determine in vitro glutamine release from nanoparticles, PDG-MSNPs (500 mg) were dispersed in PBS solution (10 mL, pH=7.4), under magnetic stirrer at 37° C. At predetermined time points (day 1, 2, 3, 7, 10, and 14), the amount of glutamine released in PBS solution was measured using a Bradford assay.[3]

4. Computational Modeling of Glutamine Delivery to Pancreatic Islets from PDG-MSNPs To estimate the effects that glutamine released form our PDG-MSNPs can have on the survival and function of islets, we performed computational modeling analysis using an updated version of a previously developed and calibrated quantitative model for avascular pancreatic islets.[4,5] Briefly, the previous model used a total of four concentrations for convective and diffusive mass transport modeling with their corresponding equations (application modes) [glucose, oxygen, and local and released insulin ($c_{glucose}$, $c_{oxygen}$, $c_{local\ insulin}$, and $c_{released\ insulin}$)]. Now, we have added an additional module for the modeling of the mass transport of glutamine ($c_{glutamine}$). As before, diffusion of all species was assumed to be governed by the generic diffusion equation in its non-conservative formulation (incompressible fluid):

$$\frac{\partial c}{\partial t} + \nabla \cdot (-D\nabla c) = R - u \cdot \nabla c \quad \text{(Equation 2)}$$

where c denotes the concentration [$mol \cdot m^{-3}$], D the diffusion coefficient [$m^2 \cdot s^{-1}$], R the reaction rate [$mol \cdot m^{-3} \cdot s^{-1}$], u the velocity field [$m \cdot s^{-1}$], and V the standard del (nabla) operator $$(\nabla \equiv i\frac{\partial}{\partial x} + j\frac{\partial}{\partial y} + k\frac{\partial}{\partial z}).$$

All consumption and release rates were assumed to follow Hill-type dependence on local concentrations:

$$R = f_H(c) = R_{max}\frac{c^n}{c^n + C_{Hf}^n} \quad \text{(Equation 3)}$$

Here, $R_{max}$ denotes the maximum reaction rate [$mol \cdot m^{-3} \cdot s^{-1}$], $C_{Hf}$, the concentration corresponding to half-maximal response [$mol \cdot m^{-3}$], and n, the Hill slope characterizing the shape of the response. Diffusion coefficients and parameter ($R_{max}$, $C_{Hf}$, and n) values used for glucose, oxygen, and insulin are those from the previously developed model,[4] and values for glutamine have been added now. Diffusion coefficients of $D_{glut}$=1.0×$10^{-9}$ and 0.33×$10^{-9}$ $m^2/s$ were used for glutamine in aqueous media and islet, respectively. Islets were assumed to have a glutamine consumption rate of 5 nM/day/islet corresponding to 0.033 $M/s/m^3$ per unit volume.[6] Due to the small size of the nanoparticles compared to those of the islets, they were not modelled individually; instead, glutamine release was assumed to be homogeneous in the media surrounding the islets and proportional with the density of nanoparticles present. The sustained-release nanoparticles were assumed to be homogenously dispersed (1,000 nanoparticles per islets in 1 $mm^3$) with glutamine release rates of 3.6 nM/day/1000 particle resulting in a release rate used in the model of 0.01 $M/m^3/s$ per unit volume (corresponding to release rates measured ~2 weeks after transplantation). As before, the model was implemented in COMSOL Multiphysics (COMSOL Inc., Burlington, MA) and solved as a time-dependent (transient) problem with intermediate time-steps for the solver. The geometry used assumes islets with diameters of 120 and 150 μm cultured with PDG-MSNPs with a ratio of 1:1000 as used in this study. As the model is general and has no size- or geometry related assumptions built into it, it can be used without any additional assumptions. Mesh and boundary conditions used for glucose, oxygen, and insulin, are as described before with symmetry conditions imposed here on the left and right borders (insulin: outflow; oxygen and glucose: fixed concentration on top and bottom). Boundary conditions for glutamine were similar: fixed concentration on top and bottom, symmetry on left and right. The system was assumed to be in an aqueous media at physiological temperature (37° C.), extracellular glutamine concentrations of 0.7 mM,[7,8] and a glucose concentration of 8 mM. In a second set of models, a partition coefficient of 5 was assumed between intra- and extracellular domains, which has been built into the model through a special boundary condition using the stiff-spring method as before, and the islets were modeled as a single large cell.

5. In vitro Interactions of PDG-MSNPs with Pancreatic Islets

For all in vitro experiments, isolated islets were individually counted and manually picked-up under a microscope to achieve a density of 20 islets/well (20 islets in 200 μL of complete medium: RPMI-1640 medium (Gibco, USA) supplemented with 10% fetal bovine serum (FBS; Invitrogen, USA) and 50 U/mL penicillin-50 μg/mL streptomycin (P/S; Invitrogen, USA) were added into 96-well non-adherent tissue culture plates. All the in vitro experiments have been performed in quintuplicate (n=5) using the following experimental groups: Group 1=islets only (control); Group 2=islets cultured with glutamine alone at concentrations of 10 mM (1.5 mg/mL), 30 mM (4.5 mg/mL), and 50 mM (7.5 mg/mL); Group 3=islets cultured with G-MSNPs (50 mM of glutamine); Group 4=islets cultured with PDG-MSNPs (50 mM of glutamine) with polydopamine coating concentrations of 0.5, 1, and 2 mg/mL and coating time of 0.5 h; and Group 5=islets cultured with PDG-MSNPs (50 mM of glutamine) with polydopamine coating times of 0.5, 1, and 2 h and coating concentration of 0.5 mg/mL.

5.1. Mouse Pancreatectomy and Islet Isolation

All mice within this study were treated in accordance with the guidelines approved by the Institutional Animal Care and Use Committee (IACUC) at Stanford University. Animals were housed under conventional conditions having access to food and water ad libitum. Pancreatic islets were isolated from C57BL/6 mice (male, 6-8-week-old, Charles River Laboratories, USA), as previously described.[9] In brief, the common bile duct was cannulated with a 30G needle and the pancreas distended with 3 mL of cold collagenase solution (Fischer Scientific, USA). The pancreas was removed and islets isolated by digesting the pancreas at 37° C. for 10 min. The islets were purified using histopaque-density gradients. Islets were then washed with Hank's balanced salt solution (HBSS, Gibco, USA) supplemented with 0.1% bovine serum albumin (BSA, Gibco, USA) before being cultured in complete medium (RPMI (Gibco, USA) supplemented with 10% fetal bovine serum (FBS; Invitrogen, USA) and 50 U/mL penicillin-50 μg/mL streptomycin) within a humidified incubator at 37° C. and 5% $CO_2$.

5.2. Islet Viability

After 7 days of incubation with PDG-MSNPs, the viability of islets was assessed using Live/Dead and 3-(4,5-Dimethylthiazol-2-yl)-2,5-diphenyltetrazolium bromide (MTT) assays. Islets were labeled using fluorescein diacetate (FDA; for live cells (green fluorescence), Thermo Fisher Scientific, USA) and propidium iodide (PI; for dead cells (red fluorescence), Thermo Fisher Scientific, USA) as the Live/Dead staining solution. The culture medium was removed and the Live/Dead staining solution [FDA (75 μL/well) and PI (75 μL/well)] was added and incubated with islets for 20 min at 37° C./5% $CO_2$. At the end of the incubation time, the staining solution was removed and cells were washed three times with PBS. Finally, the live cell imaging solution (Thermo Fisher Scientific, USA) was added to each well (200 μL/well) before imaging. Images were acquired with a Zeiss LSM710 Confocal Microscope at a magnification of 20× and figures were created with the FIJI software (ImageJ, GNU General Public License). A minimum of 8 islets per experimental group were analyzed using Image-J/FIJI to quantify live and dead fluorescence within islets and the percentage of live islet were presented.

MTT solution (500 μg/mL) was added to each well and incubated at 37° C./5% $CO_2$ for 4 h. MTT is converted to an insoluble formazan crystal. Next, 200 μL of DMSO was added to each well and left at 37° C. for 10 min to dissolve the formazan crystals. Absorbance was then measured at 570 nm (Tecan, Mannedorf, Swiss). The percentage of cell viability was assessed according to the following equation:

$$\text{Cell Viability (\%)} = \frac{Abs_T}{Abs_C} \times 100 \quad \text{(Equation 4)}$$

where $Abs_T$ is the absorbance of cells treated with PDG-MSNPs or glutamine alone and $Abs_C$ is the absorbance of control cells (islets alone).

5.3. Islet Function

Islets supplemented with PDG-MSNPs were cultured in a humidified incubator under normal conditions (37° C./5% $CO_2$/20% $O_2$). After 7 days of incubation with PDG-MSNPs, the ability of islets to secrete insulin was assessed by exposing them to low glucose (i.e. basal conditions) and high glucose (i.e. stimulated conditions) media (200 μL/well). Islets were incubated in Krebs-Ringer Buffer (KRB; Sigma-Aldrich, USA) spiked with 2.8 mM glucose (low) for 2 h followed by 16.7 mM glucose (high) for 2 h at 37° C./5% $CO_2$/20% $O_2$. The supernatants were collected at the end of incubation for both basal and stimulated condition and insulin levels were quantified using a mouse insulin ELISA kit (Mercodia Developing Diagnostics, USA). The total insulin content of islets (i.e. 20 islets) was then normalized to present the amount of insulin secreted per islet.

5.4. Islet Protein Expression

To investigate proteins expressed in the islets, heat shock proteins (HSPs) array (R&D Systems, USA) was performed according to the manufacturer's recommendations with little in house modifications. This test was carried out in two experimental groups. Group 1=islets only (i.e. control) and Group 2=islets cultured with PDG-MSNPs with PD coating concentration and time of 0.5 mg/mL and 0.5 h, respectively.

Briefly, islets were homogenized in PBS using protease inhibitors cocktail (Sigma-Aldrich, USA), and centrifuged at 10,000 g for 8 min at 4° C. The total protein concentrations of samples (300 μg) were then determined using a bicinchoninic acid (BCA) assay kit (Sigma-Aldrich, USA) and samples (200 μL) with identified protein concentration were added to a membrane spotted with antibodies against HSPs-related proteins. After incubation at 4° C. for 24 h, the membranes were treated with streptavidin-horseradish peroxidase (Sigma-Aldrich, USA). Finally, the protein spots were imaged and quantified using an enhanced chemiluminescence detection system (Bio-Rad, USA) with an image analyzer (ChemiDoc, Bio-Rad, USA).

6. In Vivo Interactions of PDG-MSNPs with Pancreatic Islets 6.1. Islet Transplantation All experiments were approved by the Institutional Animal Care and Use Committee (IACUC) at Stanford University. Male C57BL/6 mice, 6-8 weeks old (Charles River Laboratories, USA), were used as both donors and recipients. All animals were maintained on a 12 h of light and 12 h of dark with ad libitum access to food and water. To induce diabetes, each mouse received an intra-peritoneal injection of streptozotocin (STZ) at the dose of 180 mg/kg; this technique is a well-established model for inducing diabetes in rodents and hence for studying islet transplantation[10-13] given that STZ selectively causes destruction of insulin producing β cells within pancreatic islets.[14] Diabetic mice were randomly assigned into 3 experimental groups and each of them have received 175 islets alone or supplemented with glutamine or with PDG-MSNPs under the right kidney capsule. Group 1=mice transplanted with islets only (n=6; control group); Group 2=mice transplanted with islets supplemented with glutamine (n=6); Group 3=mice transplanted with islets supplemented with PDG-MSNPs (50 mM of glutamine) (n=6). Furthermore, for Group 2 was used a dosage of glutamine that matched the amount of glutamine used in the case of PDG-MNPs (Group 3). The volume of transplant graft injected under the kidney capsule was same (V=10 μL) for all tested groups include islets only (V=5 μL islet+5 μL PBS), islets+glutamine alone (V=5 μL islet+5 μL glutamine), and islets+PDG-MSNPs (V=5 μL islet+5 μL PDG-MSNPs).

6.2. Metabolic Analysis

All metabolic analyses were performed in conscious, restrained mice, at the indicated time points for 30 days. A drop of blood was collected from the tail vein of the mice and the blood glucose measurements were done using a handheld glucometer (Bayer Contour Glucose Meter, USA). Mice were considered normoglycemic when non-fasting blood glucose levels were less than 200 mg/dL. Intraperitoneal glucose tolerance tests (IPGTT) were performed 2 weeks post-transplantation. Specifically, mice were fasted overnight and fasted blood glucose levels were determined before a solution of glucose (2 g/kg) was administered by intra-peritoneal injection. Subsequently, the blood glucose levels were measured each 30 minutes for 2 hours after injection allowing us to calculate the area under the curve (AUC) and blood glucose clearance rate between transplantation groups. At day 30 post-transplantation, mice were euthanized and serum and tissue (i.e. the EFP with or without PDG-MSNPs) samples collected to determine insulin levels (insulin ELISA kit; Mercodia). In addition, the EFP tissue was processed for histological (i.e. fixed in 4% paraformaldehyde, dehydrated with graded ethanol solutions, embedded in paraffin and sliced with a microtome) and/or molecular (i.e. tissues stored at −80° C. for subsequent processing to determine levels of cytokines) analyses.

6.3. Histological Analysis

At euthanasia, the kidneys transplanted with islets alone or supplemented with glutamine or with PDG-MSNPs, were harvested, fixed in 4% paraformaldehyde, dehydrated with graded ethanol solutions, embedded in paraffin and sliced with a microtome. The sections were prepared for histological and immunohistochemical (IHC) analyses to determine islet structure and viability (Haemotoxylin and Eosin (H&E) and insulin staining), and evidence of inflammation (H&E and tumor necrosis factor alpha (TNF-α) staining) via standard procedures. The stained sections were then imaged using a NanoZoomer slide scanner 2.0-RS (Hamamatsu, Japan). Results were analyzed with at least 15-20 islets from 5 different sections through the kidney of each animal. In each islet, the percentage surface area occupied by the positive (dark brown) insulin and TNF-α staining (IHC images), and blood vessels (H&E images) were measured using FIJI Image J software, and reported as the percentage of insulin (%/islet), TNF-α (%/islet) and vascularization (%/islet) of islets.[15-17]

6.4. Molecular Analysis

At euthanasia, blood samples were collected to measure serum insulin levels (insulin ELISA kit; Mercodia). The frozen kidney tissue was then homogenized as follow: tissue samples were placed in a homogenization buffer at a ratio of 1 kidney/1 mL buffer; the buffer contained a protease inhibitor combination (Sigma Aldrich, USA) including 4-(2-Aminoethyl)benzenesulfonyl fluoride hydrochloride (AEBSF, 2 mM), Aprotinin (0.3 μM), Bestatin (116 μM), trans-Epoxysuccinyl-L-leucylamido(4-guanidino)butane (E-64, 14 μM), Leupeptin (1 μM) and ethylenediaminetetraacetic acid (EDTA, 1 mM) in tissue protein extraction reagent (ThermoFisher Scientific, USA) containing phenylmethylsulfonyl fluoride (PMSF). All homogenized kidney samples were sonicated 3 times for a total of 8 s (Branson SLPe) mixed for 45 min at 4° C., before then being centrifuged at 15000 rpm (for 15 min at 4° C.). The tissue supernatant was then collected and the insulin content measured (mouse insulin ELISA kit; Mercodia); results were normalized per kidney for each mouse. The level of tissue cytokines was also measured using a mouse multiplex ELISA (eBiosciences/Affymetrix/Fisher). In brief, beads were first added to a 96 well plate and washed (Biotek ELx405). Samples were then added to the plate containing the mixed antibody-linked beads and incubated at room temperature for 1 h followed by overnight incubation at 4° C. on a plate shaker (500 rpm). Biotinylated detection antibody was then added, after which the plates were incubated at room temperature for 75 min on the plate shaker (500 rpm). Next, the samples were washed and streptavidin-PE added followed by incubation of the plate 30 min at room temperature on the plate shaker (500 rpm). The plate was then washed and a reading buffer added to all the wells. Finally, a Luminex Flex 3D instrument was used to read the plates with a lower bound of 50 beads per sample per cytokine. Control assay beads (Radix Biosolutions) were added to all wells.

7. Long-Term Biocompatibility of MSNPs

The long-term biocompatibility of our optimized nanoparticles, PDG-MSNPs obtained using a PD coating concentration of 0.5 mg/mL and a coating time of 0.5 h, was evaluated implanting them in two different locations in C57BL/6 healthy mice: the epidydimal fat pad and within the subcutaneous tissue of the mice. After 24 weeks, mice were sacrificed and the blood was collected for routine analysis (chemistry, liver and metabolic panels).

8. In Vivo Tracking of MSNPs

To fluorescently label our PDG-MSNPs, we first synthesized a fluorescein isothiocyanate (FITC)-silane precursor. FITC (Sigma Aldrich, 100 mg) and 3-aminopropyl triethoxysilane (APTES; sigma Aldrich, 100 μL) were first dissolved in ethanol (100 mL) and kept at 40° C. for 24 h. Separately, CTAB (1000 mg) was dissolved in deionized water (480 ml) contain NaOH (3.5 mL; 2 M). These two solutions were then mixed and heated to 80° C. while stirring at 500 rpm to obtain the FITC-silane precursor. The FITC-silane precursor solution (10 mL) and TEOS (5 mL) were then mixed and dissolved in water (15 mL). Finally, our synthesized PDG-MSNPs were added to the mixture and allowed to react for 24 h at room temperature. Labelled PDG-MSNPs called FITC-PDG-MSNPs were then centrifuged and washed three times with ethanol and water. The in vivo stability of our FITC-PDG-MSNPs were studied in C57/B6 mice by implanting them (85 mg) under the kidney capsule followed by fluorescence imaging using an in vivo imaging system (IVIS, Lago optical imaging system) at 500/550 excitation/emission wavelengths. Before implantation, we ensured that our FITC-PDG-MSNPs preserved their fluorescence stability over time by imaging them after incubation in PBS for 5 days. Mice implanted with FITC-PDG-MSNPs were anesthetized and imaged at 1, 5, 9, and 21 days post-implantation.

9. Statistical Analysis

All experiments were performed in n=5 for in vitro or n=6 for in vivo, and results were expressed as mean±standard error of the mean (SEM). The statistical analysis (Two-way ANOVA post-hoc Tuckey Test or unpaired Student's t-test) is expressed considering any differences statistically significant when $p<0.05$.

REFERENCES (1) Paris, J. L.; Cabanas, M. V.; Manzano, M.; Vallet-Regi, M. Polymer-Grafted Mesoporous Silica Nanoparticles as Ultrasound-Responsive Drug Carriers. *ACS Nano* 2015, 9 (11), 11023-11033.

(2) Razavi, M.; Hu, S.; Thakor, A. S. A Collagen Based Cryogel Bioscaffold Coated with Nanostructured Polydopamine as a Platform for Mesenchymal Stem Cell Therapy. *J. Biomed. Mater. Res.—Part A* 2018, 106 (8), 2213-2228.

(3) Carlsson, N.; Borde, A.; Wölfel, S.; Kerman, B.; Larsson, A. Quantification of Protein Concentration by the Bradford Method in the Presence of Pharmaceutical Polymers. *Anal. Biochem.* 2011, 411 (1), 116-121.

(4) Buchwald, P. A Local Glucose- and Oxygen Concentration-Based Insulin Secretion Model for Pancreatic Islets. *Theor. Biol. Med. Model.* 2011, 8 (1).

(5) Buchwald, P.; Tamayo-Garcia, A.; Manzoli, V.; Tomei, A. A.; Stabler, C. L. Glucose-Stimulated Insulin Release: Parallel Perifusion Studies of Free and Hydrogel Encapsulated Human Pancreatic Islets. *Biotechnol. Bioeng.* 2018, 115 (1), 232-245.

(6) Dixon, G.; Nolan, J.; McClenaghan, N.; Flatt, P. R.; Newsholme, P. A Comparative Study of Amino Acid Consumption by Rat Islet Cells and the Clonal Beta-Cell Line BRIN-BD11—The Functional Significance of L-Alanine. *J. Endocrinol.* 2003, 179 (3), 447-454.

(7) Curi, R.; Lagranha, C. J.; Doi, S. Q.; Sellitti, D. F.; Procopio, J.; Pithon-Curi, T. C.; Corless, M.; Newsholme, P. Molecular Mechanisms of Glutamine Action. *Journal of Cellular Physiology.* 2005, pp 392-401.
(8) Newsholme, P.; Brennan, L.; Bender, K. Amino Acid Metabolism, β-Cell Function, and Diabetes. *Diabetes* 2006, 55 (SUPPL. 2).
(9) Neuman, J. C.; Truchan, N. A.; Joseph, J. W.; Kimple, M. E. A Method for Mouse Pancreatic Islet Isolation and Intracellular CAMP Determination. *J. Vis. Exp.* 2014, No. 88, e50374.
(10) Ren, G.; Rezaee, M.; Razavi, M.; Taysir, A.; Wang, J.; Thakor, A. S. Adipose Tissue-Derived Mesenchymal Stem Cells Rescue the Function of Islets Transplanted in Sub-Therapeutic Numbers via Their Angiogenic Properties. *Cell Tissue Res.* 2019.
(11) Cantarelli, E.; Citro, A.; Marzorati, S.; Melzi, R.; Scavini, M.; Piemonti, L. Murine Animal Models for Preclinical Islet Transplantation: No Model Fits All (Research Purposes). *Islets.* 2013, pp 79-86.
(12) Coronel, M. M.; Geusz, R.; Stabler, C. L. Mitigating Hypoxic Stress on Pancreatic Islets via in Situ Oxygen Generating Biomaterial. *Biomaterials* 2017, 129, 139-151.
(13) Pedraza, E.; Coronel, M. M.; Fraker, C. A.; Ricordi, C.; Stabler, C. L. Preventing Hypoxia-Induced Cell Death in Beta Cells and Islets via Hydrolytically Activated, Oxygen-Generating Biomaterials. *Proc. Natl. Acad. Sci.* 2012, 109 (11), 4245-4250.
(14) Wilson, G. L.; Leiter, E. H. Streptozotocin Interactions with Pancreatic Beta Cells and the Induction of Insulin-Dependent Diabetes. *Curr. Top. Microbiol Immunol.* 1990, 156, 27-54.
(15) Razavi, M.; Zheng, F.; Telichko, A.; Wang, J.; Ren, G.; Dahl, J.; Thakor, A. S. Improving the Function and Engraftment of Transplanted Pancreatic Islets Using Pulsed Focused Ultrasound Therapy. *Sci. Rep.* 2019, 9 (1).
(16) Razavi, M.; Primavera, R.; Kevadiya, B. D.; Wang, J.; Buchwald, P.; Thakor, A. S. A Collagen Based Cryogel Bioscaffold That Generates Oxygen for Islet Transplantation. *Adv. Funct. Mater.* 2020, 30 (15).
(17) Canzano, J. S.; Nasif, L. H.; Butterworth, E. A.; Fu, D. A.; Atkinson, M. A.; Campbell-Thompson, M. Islet Microvasculature Alterations With Loss of Beta-Cells in Patients With Type 1 Diabetes. *J. Histochem. Cytochem.* 2019, 67 (1), 41-52.
(18) Faleo, G.; Russ, H. A.; Wisel, S.; Parent, A. V.; Nguyen, V.; Nair, G. G.; Freise, J. E.; Villanueva, K. E.; Szot, G. L.; Hebrok, M.; et al. Mitigating Ischemic Injury of Stem Cell-Derived Insulin-Producing Cells after Transplant. *Stem Cell Reports* 2017, 9 (3), 807-819.
(19) Liu, Z.; Jeppesen, P. B.; Gregersen, S.; Chen, X.; Hermansen, K. Dose- and Glucose-Dependent Effects of Amino Acids on Insulin Secretion from Isolated Mouse Islets and Clonal INS-1E Beta-Cells. *Rev. Diabet. Stud.* 2008, 5 (4), 232-244.
(20) Jang, H. J.; Kwak, J. H.; Cho, E. Y.; We, Y. M.; Lee, Y. H.; Kim, S. C.; Han, D. J. Glutamine Induces Heat-Shock Protein-70 and Glutathione Expression and Attenuates Ischemic Damage in Rat Islets. *Transplant. Proc.* 2008, 40 (8), 2581-2584.
(21) Lindström, P.; Sehlin, J. Aromatic Amino Acids and Pancreatic Islet Function: A Comparison of I-Tryptophan and I-5-Hydroxytryptophan. *Mol. Cell. Endocrinol.* 1986, 48 (2-3), 121-126.
(22) Mullooly, N.; Vernon, W.; Smith, D. M.; Newsholme, P. Elevated Levels of Branched-Chain Amino Acids Have Little Effect on Pancreatic Islet Cells, but I-Arginine Impairs Function through Activation of the Endoplasmic Reticulum Stress Response. *Exp. Physiol.* 2014.
(23) Millar, D. S.; Lewis, M. D.; Horan, M.; Newsway, V.; Easter, T. E.; Gregory, J. W.; Fryklund, L.; Norin, M.; Crowne, E. C.; Davies, S. J.; et al. Novel Mutations of the Growth Hormone 1 (GH1) Gene Disclosed by Modulation of the Clinical Selection Criteria for Individuals with Short Stature. *Hum. Mutat.* 2003, 21 (4), 424-440.
(24) Starenki, D.; Hong, S. K.; Lloyd, R. V.; Park, J. I. Mortalin (GRP75/HSPA9) Upregulation Promotes Survival and Proliferation of Medullary Thyroid Carcinoma Cells. *Oncogene* 2015, 34 (35), 4624-4634.
(25) Mizzen, L. A.; Chang, C.; Garrels, J. I.; Welch, W. J. Identification, Characterization, and Purification of Two Mammalian Stres Proteins Present in Mitochondria, Grp 75, a Member of the Hsp 70 Family and Hsp 58, a Homolog of the Bacterial GroEL Protein. *J. Biol. Chem.* 1989, 264 (34), 20664-20675.
(26) Kondo, R.; Gleixner, K. V.; Mayerhofer, M.; Vales, A.; Gruze, A.; Samorapoompichit, P.; Greish, K.; Krauth, M. T.; Aichberger, K. J.; Pickl, W. F.; et al. Identification of Heat Shock Protein 32 (Hsp32) as a Novel Survival Factor and Therapeutic Target in Neoplastic Mast Cells. *Blood* 2007.
(27) Galea-Lauri, J.; Richardson, A. J.; Latchman, D. S.; Katz, D. R. Increased Heat Shock Protein 90 (Hsp90) Expression Leads to Increased Apoptosis in the Monoblastoid Cell Line U937 Following Induction with TNF-Alpha and Cycloheximide: A Possible Role for Immunopathology. *J. Immunol.* 1996, 157, 4109-4118.
(28) Thomas, G. P.; Welch, W. J.; Mathews, M. B.; Feramisco, J. R. Molecular and Cellular Effects of Heat-Shock and Related Treatments of Mammalian Tissue-Culture Cells. *Cold Spring Harb. Symp. Quant. Biol.* 1982, 46 (2), 985-996.
(29) Dulak, J.; Deshane, J.; Jozkowicz, A.; Agarwal, A. Heme Oxygenase-1 and Carbon Monoxide in Vascular Pathobiology: Focus on Angiogenesis. *Circulation.* 2008, pp 231-241.
(30) Deshane, J.; Chen, S.; Caballero, S.; Grochot-Przeczek, A.; Was, H.; Li Calzi, S.; Lach, R.; Hock, T. D.; Chen, B.; Hill-Kapturczak, N.; et al. Stromal Cell-Derived Factor 1 Promotes Angiogenesis via a Heme Oxygenase 1-Dependent Mechanism. *J. Exp. Med.* 2007, 204 (3), 605-618.
(31) Wang, K.; Wang, X.; Han, C.; Chen, L.; Luo, Y. Scaffold-Supported Transplantation of Islets in the Epididymal Fat Pad of Diabetic Mice. *J. Vis. Exp.* 2017, No. 125.
(32) Gibly, R. F.; Zhang, X.; Lowe, W. L.; Shea, L. D. Porous Scaffolds Support Extrahepatic Human Islet Transplantation, Engraftment, and Function in Mice. *Cell Transplant.* 2013, 22 (5), 811-819.
(33) Lacy, P. E.; Hegre, O. D.; Gerasimidi-Vazeou, A.; Gentile, F. T.; Dionne, K. E. Maintenance of Normoglycemia in Diabetic Mice by Subcutaneous Xenografts of Encapsulated Islets. *Science* (80-.). 1991, 254 (5039), 1782-1784.
(34) Smink, A. M.; Li, S.; Swart, D. H.; Hertsig, D. T.; de Haan, B. J.; Kamps, J. A. A. M.; Schwab, L.; van Apeldoorn, A. A.; de Koning, E.; Faas, M. M.; et al. Stimulation of Vascularization of a Subcutaneous Scaffold Applicable for Pancreatic Islet-Transplantation Enhances Immediate Post-Transplant Islet Graft Function but Not Long-Term Normoglycemia. *J. Biomed. Mater. Res.—Part A* 2017, 105 (9), 2533-2542.

(35) Otto, G. P.; Rathkolb, B.; Oestereicher, M. A.; Lengger, C. J.; Moerth, C.; Micklich, K.; Fuchs, H.; Gailus-Durner, V.; Wolf, E.; Hrabe de Angelis, M. Clinical Chemistry Reference Intervals for C57BL/6J, C57BL/6N, and C3HeB/FeJ Mice (*Mus Musculus*). *J. Am. Assoc. Lab. Anim. Sci.* 2016, 55 (4), 375-386.

(36) Boehm, O.; Zur, B.; Koch, A.; Tran, N.; Freyenhagen, R.; Hartmann, M.; Zacharowski, K. Clinical Chemistry Reference Database for Wistar Rats and C57/BL6 Mice. *Biol. Chem.* 2007, 388 (5), 547-554.

What is claimed is:

1. A nanoparticle for supplying a therapeutic agent to transplanted cells, the nanoparticle comprising:

a) a mesoporous silica core comprising a plurality of pores, wherein the pores have a pore diameter ranging from about 2 nm to about 20 nm;

b) one or more therapeutic agents, wherein the plurality of pores contains the therapeutic agents; and c) a layer comprising polydopamine encapsulating the mesoporous silica core, wherein the layer comprising polydopamine has a thickness sufficient to allow sustained release of effective amounts of the one or more therapeutic agents from the nanoparticle at least until the transplanted cells develop a functional microcirculation.

2. The nanoparticle of claim 1, wherein the thickness of the layer comprising polydopamine ranges from about 2 nm to about 10 nm.

3. The nanoparticle of claim 1, wherein the thickness of the layer is sufficient to allow sustained release of the one or more therapeutic agents from the nanoparticle for at least 14 days.

4. The nanoparticle of claim 1, wherein the nanoparticle has a diameter ranging from about 50 nm to about 250 nm and a surface area of at least 900 $m^2/g$.

5. The nanoparticle of claim 1, wherein the mesoporous silica core has a porosity of at least 85%.

6. The nanoparticle of claim 1, wherein the therapeutic agents are selected from the group consisting of nutrients, drugs, exosomes, antioxidants, and vitamins, wherein (i) the nutrient is an amino acid, a protein, a peptide, a carbohydrate, and/or a lipid;

(ii) the drug is an anti-inflammatory, an immunosuppressant, or an anti-cancer drug;

(iii) the antioxidant is a thiol, ascorbic acid, a carotene, a tocotrienol, lipolic acid, uric acid, or ubiquinone; and/or (iv) the vitamin is vitamin A, vitamin B1, vitamin B2, vitamin B3, vitamin B5, vitamin B6, vitamin B7, vitamin B9, vitamin B12, vitamin C, vitamin D, vitamin E, and/or vitamin K.

7. The nanoparticle of claim 6, wherein the protein is a hormone, a growth factor, a transcription factor, an enzyme, a receptor, an antibody, or a combination thereof.

8. The nanoparticle of claim 6, wherein the amino acids are selected from the group consisting of glutamine, alanine, cysteine, tryptophan, leucine, methionine, isoleucine, arginine, lysine, proline, and homocysteine.

9. The nanoparticle of claim 8, wherein the one or more therapeutic agents comprise at least glutamine.

10. A composition comprising the nanoparticle of claim 1 and a pharmaceutically acceptable excipient.

11. The composition of claim 10, further comprising therapeutic cells.

12. A method of supplying one or more therapeutic agents to transplanted cells in a subject, the method comprising implanting the nanoparticle of claim 1 in proximity to the transplanted cells, wherein the nanoparticle releases the one or more therapeutic agents from the plurality of pores to allow uptake of the one or more therapeutic agents by the transplanted cells.

13. The method of claim 12, wherein the transplanted cells are genetically modified cells.

14. The method of claim 12, wherein the transplanted cells are insulin-secreting cells.

15. The method of claim 14, wherein the insulin-secreting cells are pancreatic beta cells, islets obtained from a donor, or insulin-secreting cells derived from stem cells or pancreatic progenitor cells.

16. The method of claim 12, wherein the one or more therapeutic agents are selected from the group consisting of nutrients, small molecules, drugs, exosomes, antioxidants, and vitamins.

17. The method of claim 16, wherein the nutrients are selected from the group consisting of amino acids, glucose, fatty acids, and cholesterol.

18. The method of claim 17, wherein said one or more therapeutic agents comprise at least one amino acid selected from the group consisting of glutamine, alanine, cysteine, tryptophan, leucine, methionine, isoleucine, arginine, lysine, proline, and homocysteine.

19. The method of claim 18, wherein said at least one amino acid is glutamine.

20. The composition of claim 10, further comprising insulin-secreting cells and glutamine.

21. The composition of claim 20, wherein the insulin-secreting cells are pancreatic beta cells, islets obtained from a donor, or insulin-secreting cells derived from stem cells or pancreatic progenitor cells.

22. A method of regulating blood glucose levels in a subject who has hyperglycemia or type 1 diabetes, the method comprising transplanting a therapeutically effective amount of insulin-secreting cells at a transplantation site in the subject in combination with administering a therapeutically effective amount of the nanoparticle of claim 9 locally at the transplantation site.

23. The method of claim 22, wherein the insulin-secreting cells are autologous, allogeneic, or xenogeneic pancreatic beta cells or islets, or insulin-secreting cells derived from stem cells or pancreatic progenitor cells.

24. The method of claim 22, wherein the transplantation site is in a kidney, liver, omentum, peritoneum, abdomen, submuscular tissue, or subcutaneous tissue of the subject.

25. The nanoparticle of claim 6, wherein the carbohydrate is a monosaccharide, a disaccharide, an oligosaccharide, or a polysaccharide.

26. The nanoparticle of claim 6, wherein the monosaccharide is glucose.

27. The nanoparticle of claim 6, wherein the lipid is a fatty acid, a triglyceride, a phospholipid, or a sterol.

28. The nanoparticle of claim 27, wherein the sterol is a steroid, a cholesterol, or a cholesterol ester.

29. The nanoparticle of claim 6, wherein the drug is an anti-cancer drug.

30. The nanoparticle of claim 29, wherein the anti-cancer drug is aliteretinoin, altretamine, anastrozole, azathioprine, bicalutarnide, busulfan, capecitabine, carboplatin, cisplatin, cyclophosphamide, cytarabine, doxorubicin, epirubicin, etoposide, exemestane, methotrexate, taxol, vincristine, or vinorelbine.

31. The nanoparticle of claim 6, wherein the thiol is glutathione, dithiothreitol, or β-mercaptoethanol.

32. The nanoparticle of claim 6, wherein the carotene is β-carotene or retinol.

33. The nanoparticle of claim 6, wherein the tocopherol is α-tocopherol.

* * * * *